US008658603B2

(12) United States Patent
Holoshitz et al.

(10) Patent No.: US 8,658,603 B2
(45) Date of Patent: Feb. 25, 2014

(54) COMPOSITIONS AND METHODS FOR INDUCING AN IMMUNE RESPONSE

(75) Inventors: Joseph Holoshitz, Ann Arbor, MI (US); Song Ling, Ypsilanti, MI (US); Xiujun Pi, Ann Arbor, MI (US); Denise de Almeida, Dearborn, MI (US); Chaim Gilon, Jerusalem (IL); Amnon Hoffman, Jerusalem (IL)

(73) Assignee: The Regents of the University of Michigan, Ann Arbor, MI (US)

( * ) Notice: Subject to any disclaimer, the term of this patent is extended or adjusted under 35 U.S.C. 154(b) by 70 days.

(21) Appl. No.: 13/331,354

(22) Filed: Dec. 20, 2011

(65) Prior Publication Data

US 2012/0141516 A1 Jun. 7, 2012

Related U.S. Application Data

(63) Continuation-in-part of application No. 13/162,382, filed on Jun. 16, 2011.

(60) Provisional application No. 61/355,413, filed on Jun. 16, 2010.

(51) Int. Cl.
*A61K 38/12* (2006.01)
(52) U.S. Cl.
USPC .......................................... 514/21.1
(58) Field of Classification Search
None
See application file for complete search history.

(56) References Cited

U.S. PATENT DOCUMENTS

| 3,854,480 | A | 12/1974 | Zaffaroni |
| 4,235,877 | A | 11/1980 | Fullerton |
| 4,452,775 | A | 6/1984 | Kent |
| 4,596,556 | A | 6/1986 | Covey et al. |
| 4,675,189 | A | 6/1987 | Kent et al. |
| 5,057,540 | A | 10/1991 | Kensil et al. |
| 5,075,109 | A | 12/1991 | Eldridge et al. |
| 5,133,974 | A | 7/1992 | Garegnani et al. |
| 5,284,656 | A | 2/1994 | Pitt et al. |
| 5,407,686 | A | 4/1995 | Bhalani et al. |
| 5,451,569 | A | 9/1995 | Tam et al. |
| 5,736,152 | A | 4/1998 | Dunn |
| 5,993,412 | A | 11/1999 | Bonicatto et al. |
| 6,005,099 | A | 12/1999 | Bauer et al. |
| 6,651,655 | B1 | 11/2003 | Licalsi et al. |
| 2005/0215529 | A1 | 9/2005 | Holoshitz |
| 2005/0238660 | A1 | 10/2005 | Babiuk |
| 2005/0281843 | A1 | 12/2005 | Singh |

FOREIGN PATENT DOCUMENTS

| EP | 0468520 | 8/1991 |
| EP | 0517565 | 12/1992 |
| EP | 0549074 | 6/1993 |
| GB | 2122204 | 1/1984 |
| WO | 88/09336 | 1/1988 |
| WO | 92/19265 | 11/1992 |
| WO | 93/13202 | 7/1993 |
| WO | 94/00153 | 1/1994 |
| WO | 94/21292 | 9/1994 |
| WO | 95/14026 | 5/1995 |
| WO | 95/17210 | 6/1995 |
| WO | 96/02555 | 2/1996 |
| WO | 96/11711 | 4/1996 |
| WO | 96/33739 | 10/1996 |
| WO | 97/48440 | 12/1997 |
| WO | 98/16247 | 4/1998 |
| WO | 98/20734 | 5/1998 |
| WO | 98/28037 | 7/1998 |
| WO | 98/56414 | 12/1998 |
| WO | 99/10008 | 3/1999 |
| WO | 99/11241 | 3/1999 |
| WO | 99/12565 | 3/1999 |
| WO | 99/27961 | 6/1999 |

OTHER PUBLICATIONS

Ito et al. (J. Exp. Med., 1997, 183: 2635-2644).*
Ling et al. (Arthritis Research & Therapy, 2007, 9:R5, pp. 1-12).*
Holoshitz et al. (Annals N.Y. Acad. Sci., 2007, 1110: 73-83).*
Hucke et al. (Infection and Immunity, 2004, 72: 2723-2730).*
Munn et al. (J. Clin. Investigation, 2007, 117: 1147-1154).*
Adjei, et al., Bioavailability of leuprolide following intratracheal administration to beagle dogs, Int. J. Pharmaceutics 1990; 63:135-144.
Adjei et al., Pulmonary delivery of peptide drugs: effect of particle size on bioavailability of leuprolide acetate in healthy male volunteers, Pharm Res. Jun. 1990;7(6):565-9.
Alberati-Giani et al., Differential regulation of indoleamine 2,3-dioxygenase expression by nitric oxide and inflammatory mediators in IFN-gamma-activated murine macrophages and microglial cells, J Immunol. Jul. 1, 1997;159(1):419-26.
Baban et al., IDO activates regulatory T cells and blocks their conversion into Th17-like T cells, J Immunol. Aug. 15, 2009;183(4):2475-83. doi: 10.4049/jimmunol.0900986. Epub Jul. 27, 2009.
Braquet et al., Effect of endothelin-1 on blood pressure and bronchopulmonary system of the guinea pig, J Cardiovasc Pharmacol. 1989;13 Suppl 5:S143-6; discussion S150.
Brazolot-Millan et al., CpG DNA can induce strong Th1 humoral and cell-mediated immune responses against hepatitis B surface antigen in young mice, Proc Natl Acad Sci U S A. Dec. 22, 1998;95(26):15553-8.
Chan and White, Fmoc Solid Phase Peptide Synthesis; Oxford: Oxford University Press, 2000.
Crisma et al., Peptide models for beta-turns. A circular dichroism study, Int J Pept Protein Res. Apr. 1984;23(4):411-9.

(Continued)

*Primary Examiner* — Ilia Ouspenski
(74) *Attorney, Agent, or Firm* — Tyler J. Sisk; Casimir Jones S.C.

(57) ABSTRACT

The present invention provides compositions and methods for inducing an immune response in a subject. In particular, the present invention provides compositions comprising immunostimulatory ligands (ISL) and methods of inducing an immune response in a subject therewith. Compositions and methods of the present invention find use in, among other things, clinical (e.g. therapeutic and preventative medicine (e.g., vaccination)) and research applications.

11 Claims, 20 Drawing Sheets

(56) References Cited

OTHER PUBLICATIONS

Davis et al., CpG DNA is a potent enhancer of specific immunity in mice immunized with recombinant hepatitis B surface antigen, J Immunol. Jan. 15, 1998;160(2):870-6.

Day et al., Ex vivo analysis of human memory CD4 T cells specific for hepatitis C virus using MHC class II tetramers, J Clin Invest. Sep. 2003;112(6):831-42.

Debs, et al., Lung-specific delivery of cytokines induces sustained pulmonary and systemic immunomodulation in rats, J Immunol. May 15, 1998;140(10):3482-8.

Fallarino et al., Functional expression of indoleamine 2,3-dioxygenase by murine CD8 alpha(+) dendritic cells, Int Immunol. Jan. 2002;14(1):65-8.

Gill and von Hippel, Calculation of protein extinction coefficients from amino acid sequence data, Anal Biochem. Nov. 1, 1989;182(2):319-26.

Gilon et al., Backbone cyclization: A new method for conferring conformational constraint on peptides, Biopolymers. May 1991;31(6):745-50.

Grohmann et al., IL-12 acts directly on DC to promote nuclear localization of NF-kappaB and primes DC for IL-12 production, Immunity. Sep. 1998;9(3):315-23.

Guinn et al., Recent advances and current challenges in tumor immunology and immunotherapy, Mol Ther. Jun. 2007;15(6):1065-71. Epub Mar. 20, 2007.

Happel et al., Pulmonary interleukin-23 gene delivery increases local T-cell immunity and controls growth of *Mycobacterium tuberculosis* in the lungs, Infect Immun. Sep. 2005;73(9):5782-8.

Levin et al., Peptides that bind the HIV-1 integrase and modulate its enzymatic activity—kinetic studies and mode of action, FEBS J. Jan. 2011;278(2):316-30 Article first published online: Dec. 13, 2010.

Hilgers et al., Synergistic effects of synthetic adjuvants on the humoral immune response, Int Arch Allergy Appl Immunol. 1986;79(4):392-6.

Hilgers et al., Synthetic sulpholipopolysaccharides: novel adjuvants for humoral immune responses, Immunology. Jan. 1987;60(1):141-6.

Holoshitz & Ling, Nitric oxide signaling triggered by the rheumatoid arthritis shared epitope: a new paradigm for MHC disease association?, Ann N Y Acad Sci. Sep. 2007;1110:73-83.

Hubbard, et al., Anti-neutrophil-elastase defenses of the lower respiratory tract in alpha 1-antitrypsin deficiency directly augmented with an aerosol of alpha 1-antitrypsin, Ann Intern Med. Aug. 1, 1989;111(3):206-12.

Hucke et al., Nitric oxide-mediated regulation of gamma interferon-induced bacteriostasis: inhibition and degradation of human indoleamine 2,3-dioxygenase, Infect Immun. May 2004;72(5):2723-30.

Hurevich et al., Novel method for the synthesis of urea backbone cyclic peptides using new Alloc-protected glycine building units, J Pept Sci. Apr. 2010;16(4):178-85.

Illum et al., Hyaluronic acid ester microspheres as a nasal delivery system for insulin, J. Controlled Rel., 1994, 29:133-141.

Ivanov et al., Transcriptional regulation of Th17 cell differentiation, Semin Immunol. Dec. 2007;19(6):409-17.

Iwanami et al., Altered peptide ligands inhibit arthritis induced by glucose-6-phosphate isomerase peptide, Arthritis Res Ther. 2009;11(6):R167.

Jin et al., The inflammatory Th 17 subset in immunity against self and non-self antigens, Autoimmunity. Mar. 2008;41 (2):154-62.

Johnson, Secondary structure of proteins through circular dichroism spectroscopy, Annu Rev Biophys Biophys Chem. 1988;17:145-66.

Kensil et al., Separation and characterization of saponins with adjuvant activity from *Quillaja saponaria* Molina cortex, J Immunol. Jan. 15, 1991;146(2):431-7.

Kensil, Saponins as vaccine adjuvants, Crit Rev Ther Drug Carrier Syst. 1996;13(1-2):1-55.

Khader & Cooper, IL-23 and IL-17 in tuberculosis, Cytokine. Feb. 2008;41(2):79-83.

Kolls & Lindén, Interleukin-17 family members and inflammation, Immunity. Oct. 2004;21(4):467-76.

Korn et al., IL-21 initiates an alternative pathway to induce proinflammatory T(H)17 cells, Nature. Jul. 26, 2007;448 (7152):484-7.

Lacaille-Dubois and Wagner, A review of the biological and pharmacological activities of saponins, Phytomedicine. Mar. 1996;2(4):363-86.

Ling & Holoshitz, The rheumatoid arthritis shared epitope triggers innate immune signaling via cell surface calreticulin, J Immunol. Nov. 1, 2007;179(9):6359-67.

Ling et al., The rheumatoid arthritis shared epitope increases cellular susceptibility to oxidative stress by antagonizing an adenosine-mediated anti-oxidative pathway, Arthritis Res Ther. 2007;9(1):R5.

Ling et al., Activation of nitric oxide signaling by the rheumatoid arthritis shared epitope, Arthritis Rheum. Nov. 2006;54 (11):3423-32.

Ling et al., Genoprotective pathways. II. Attenuation of oxidative DNA damage by isopentenyl diphosphate, Mutat Res. Oct. 4, 2004;554(1-2):33-43.

McCluskie and Davis, CpG DNA is a potent enhancer of systemic and mucosal immune responses against hepatitis B surface antigen with intranasal administration to mice, J Immunol. Nov. 1, 1998;161(9):4463-6.

Moellering et al., Direct inhibition of the NOTCH transcription factor complex, Nature. Nov. 12, 2009;462(7270):182-8.

Munn & Mellor, Indoleamine 2,3-dioxygenase and tumor-induced tolerance, J Clin Invest. May 2007;117(5):1147-54.

Notley et al., Blockade of tumor necrosis factor in collagen-induced arthritis reveals a novel immunoregulatory pathway for Th1 and Th17 cells, J Exp Med. Oct. 27, 2008;205(11):2491-7.

Olson et al., Acidic residues in the DR beta chain third hypervariable region are required for stimulation of a DR(alpha, beta 1*0402)-restricted T-cell clone, Hum Immunol. Nov. 1994;41(3):193-200.

Orme, The search for new vaccines against tuberculosis, J Leukoc Biol. Jul. 2001;70(1):1-10.

Oswein, et al. "Aerosolization of Proteins", 1990; Proceedings of Symposium on Respiratory Drug Delivery II Keystone, Colorado.

Pakkala et al., Activity and stability of human kallikrein-2-specific linear and cyclic peptide inhibitors, J Pept Sci. May 2007;13(5):348-53.

Popov & Schultze, IDO-expressing regulatory dendritic cells in cancer and chronic infection, J Mol Med (Berl). Feb. 2008;86(2):145-60.

Puan et al., Preferential recognition of a microbial metabolite by human Vgamma2Vdelta2 T cells, Int Immunol. May 2007;19(5):657-73.

Quinn et al., Accelerating the secondary immune response by inactivating CD4(+)CD25(+) T regulatory cells prior to BCG vaccination does not enhance protection against tuberculosis, Eur J Immunol. Mar. 2008;38(3):695-705.

Rouse & Suvas, Regulatory cells and infectious agents: detentes cordiale and contraire, J Immunol. Aug. 15, 2004;173 (4):2211-5.

Schabowsky et al., Targeting CD4+CD25+FoxP3+ regulatory T-cells for the augmentation of cancer immunotherapy, Curr Opin Investig Drugs. Dec. 2007;8(12):1002-8.

Sharma et al., Plasmacytoid dendritic cells from mouse tumor-draining lymph nodes directly activate mature Tregs via indoleamine 2,3-dioxygenase, J Clin Invest Sep. 2007;117(9):2570-82.

Sharma et al., Indoleamine 2,3-dioxygenase controls conversion of Foxp3+ Tregs to TH17-like cells in tumor-draining lymph nodes, Blood. Jun. 11, 2009;113(24):6102-11.

Smith et al., Pulmonary Deposition and Clearance of Aerosolized Alpha-1-Proteinase Inhibitor Administered to Dogs and to Sheep, J Clin Invest. 1989; 84(4):1145-1154.

Stewart et al., The MCL-1 BH3 helix is an exclusive MCL-1 inhibitor and apoptosis sensitizer, Nat Chem Biol. Aug. 2010;6(8):595-601.

Takikawa et al., Mechanism of interferon-gamma action. Characterization of indoleamine 2,3-dioxygenase in cultured human cells induced by interferon-gamma and evaluation of the enzyme-mediated tryptophan degradation in its anticellular activity, J Biol Chem. Feb. 5, 1988;263(4):2041-8.

(56) References Cited

OTHER PUBLICATIONS

Tal-Gan et al., Synthesis and structure-activity relationship studies of peptidomimetic PKB/Akt inhibitors: the significance of backbone interactions, Bioorg Med Chem. Apr. 15, 2010;18(8):2976-85.

Thomas et al., Nitric oxide inhibits indoleamine 2,3-dioxygenase activity in interferon-gamma primed mononuclear phagocytes, J Biol Chem. May 20, 1994;269(20):14457-64.

Walensky et al., Activation of apoptosis in vivo by a hydrocarbon-stapled BH3 helix, Science. Sep. 3, 2004;305 (5689):1466-70.

Wilczynski et al., The role of T-regulatory cells in pregnancy and cancer, Front Biosci. Jan. 1, 2008;13:2275-89.

Wozniak et al., Plasmid interleukin-23 (IL-23), but not plasmid IL-27, enhances the protective efficacy of a DNA vaccine against *Mycobacterium tuberculosis* infection, Infect Immun. Jan. 2006;74(1):557-65.

Wu et al., Genoprotective pathways. Part I. Extracellular signaling through G(s) protein-coupled adenosine receptors prevents oxidative DNA damage, Mutat Res. Feb. 26, 2004;546(1-2):93-102.

Zou, Immunosuppressive networks in the tumour environment and their therapeutic relevance, Nat Rev Cancer. Apr. 2005;5(4):263-74.

* cited by examiner

SEQUENCE LISTING

```
<160> NUMBER OF SEQ ID NOS: 14

<210> SEQ ID NO 1
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Gln or Lys
<220> FEATURE:
<221> NAME/KEY: MISC_FEATURE
<222> LOCATION: (2)..(2)
<223> OTHER INFORMATION: Xaa is Lys or Arg

<400> SEQUENCE: 1

Xaa Xaa Arg Ala Ala
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Gln Lys Arg Ala Ala
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic
```

```
<400> SEQUENCE: 3

Gln Arg Arg Ala Ala
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic

<400> SEQUENCE: 4

Lys Lys Arg Ala Ala
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic

<400> SEQUENCE: 5

Lys Arg Arg Ala Ala
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Gln or Arg
<220> FEATURE:
<221> NAME/KEY: MISC_FEATURE
<222> LOCATION: (2)..(2)
<223> OTHER INFORMATION: Xaa is Lys or Arg

<400> SEQUENCE: 6

Xaa Xaa Arg Ala Ala
1               5

<210> SEQ ID NO 7
<211> LENGTH: 15
<212> TYPE: PRT
<213> ORGANISM: Artificial Sequence
<220> FEATURE:
<223> OTHER INFORMATION: Synthetic

<400> SEQUENCE: 7

Lys Asp Leu Leu Glu Gln Lys Arg Ala Ala Val Asp Thr Tyr Cys
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic

<400> SEQUENCE: 8

Lys Asp Leu Leu Glu Gln Arg Arg Ala Ala Val Asp Thr Tyr Cys
1               5                   10                  15

<210> SEQ ID NO 9
```

```
<211> LENGTH: 15
<212> TYPE: PRT
<213> ORGANISM: Artificial Sequence
<220> FEATURE:
<223> OTHER INFORMATION: Synthetic

<400> SEQUENCE: 9

Lys Asp Ile Leu Glu Asp Glu Arg Ala Ala Val Asp Thr Tyr Cys
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic

<400> SEQUENCE: 10

Lys Asp Leu Leu Glu Gln Arg Arg Ala Glu Val Asp Thr Tyr Cys
1               5                   10                  15

<210> SEQ ID NO 11
<211> LENGTH: 5
<212> TYPE: PRT
<213> ORGANISM: Artificial Sequence
<220> FEATURE:
<223> OTHER INFORMATION: Synthetic

<400> SEQUENCE: 11

Asp Glu Arg Ala Ala
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic

<400> SEQUENCE: 12

Gln Arg Arg Ala Glu
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic

<400> SEQUENCE: 13

Arg Lys Arg Ala Ala
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic

<400> SEQUENCE: 14

Arg Arg Arg Ala Ala
1               5
```

COMPOSITIONS AND METHODS FOR INDUCING AN IMMUNE RESPONSE This application is a continuation-in-part of U.S. patent application Ser. No. 13/162,382 filed Jun. 16, 2011, which claims priority to U.S. Provisional Patent Application Ser. No. 61/355,413 filed Jun. 16, 2010, each of which is hereby incorporated by reference in its entirety.

STATEMENT REGARDING FEDERALLY SPONSORED RESEARCH OR DEVELOPMENT

This invention was made with government support under AI047331, AR055170 and AR056786 awarded by the National Institutes of Health. The government has certain rights in the invention.

FIELD OF THE INVENTION

The present invention provides compositions and methods for inducing an immune response in a subject. In particular, the present invention provides compositions comprising immunostimulatory ligands (ISL) and methods of inducing an immune response in a subject therewith. Compositions and methods of the present invention find use in, among other things, clinical (e.g. therapeutic and preventative medicine (e.g., vaccination)) and research applications.

BACKGROUND

Recent evidence indicates that two newly identified subsets of T lymphocytes, regulatory T (Treg) cells and IL-17-producing T helper (Th17), are playing reciprocal roles in immune responses. Treg cells act as suppressors of the immune response against tumors and infectious pathogens (Wilczynski et al. Front Biosci. 2008 Jan. 1; 13:2275-89; Rouse & Suvas. J. Immunol. 2004 Aug. 15; 173(4):2211-5; herein incorporated by reference in their entireties). Among various molecular mechanisms involved in Treg expansion, is the tolerogenic enzyme indoleamine 2,3 dioxygenase (IDO). This key enzyme has been shown to be involved in both tumor- and pathogen associated tolerance (Munn & Mellor. J Clin Invest. 2007 May; 117(5):1147-54; Popov & Schultze. J Mol Med. 2008 February; 86(2):145-60); herein incorporated by reference in their entireties). The role of Th17 cells in cancer has been less well characterized, however cytokine, IL-17, has been shown to increase recruitment of macrophages to tumor sites and stimulate generation of cytotoxic T cells, indicating that Th17 cells play an anti-tumor role (Kolls & Lindén. Immunity. 2004 October; 21(4):467-76; herein incorporated by reference in its entirety). The evidence for the involvement of Th17 cells in anti-infection immune responses is abundant. There are strong indications that Th17 cells, their key cytokine, IL-17, as well as the Th17-expanding cytokine, IL-23, all play important roles in protection against pathogens (Jin et al. Autoimmunity. 2008 March; 41(2):154-62; herein incorporated by reference in its entirety).

Attempts have been made in the past to inhibit Treg cells to improve immune response. Because Treg cells express high affinity IL-2 receptors (CD25), experiments using anti-CD25 antibodies, or IL-2 conjugated with toxins have been carried out in various experimental tumor models and in human trials with mixed results (Schabowsky et al. Curr Opin Investig Drugs. 2007 December; 8(12):1002-8; herein incorporated by reference in its entirety). Similarly, depleting Treg cells by anti-CD25 antibodies failed to improve protective immunity against BCG in mice (Quinn et al. Eur J. Immunol. 2008 March; 38(3):695-705; herein incorporated by reference in its entirety). Other immune stimulating approaches, using antibodies against CTLA-4 or GITR have been unsuccessful (Schabowsky et al. Curr Opin Investig Drugs. 2007 December; 8(12):1002-8; herein incorporated by reference in its entirety). Thus, taken together, current strategies to inhibit Treg suffer from significant pitfalls.

Immunotherapy is an appealing anti-cancer treatment strategy. However, despite the fact that tumor cells express many immunogenic antigens, the immune system often fails to recognize or respond to them. This occurs because cancer cells utilize mechanisms that render the immune system tolerant, thereby evading immune recognition and/or eradication (Zou. Nat. Rev Cancer. 2005 April; 5(4):263-74; herein incorporated by reference in its entirety). Similarly, many pathogens have evolved sophisticated strategies to manipulate and evade their host immune system (Rouse. J. Immunol. 2004 Aug. 15; 173(4):2211-5; herein incorporated by reference in its entirety). Consequently, attempts to establish preventive or therapeutic immunity using conventional immunization protocols have often met with disappointing results (Orme. J Leukoc Biol. 2001 July; 70(1):1-10; Guinn et al. Mol. Ther. 2007 June; 15(6):1065-71; herein incorporated by reference in their entireties).

There have been no meaningful attempts to investigate the therapeutic utility of Th17 stimulation against tumors. In infectious diseases, on the other hand, there has been progress. The growing realization that the IL-23/Th17 axis is critical in both primary protective response and vaccination (Khader & Cooper. Cytokine. 2008 February; 41(2):79-83; herein incorporated by reference in its entirety), has prompted IL-23 gene transfer experiments in mice (Happel et al. Infect Immun. 2005 September; 73(9):5782-8; Wozniak et al. Infect Immun. 2006 January; 74(1):557-65; herein incorporated by reference in their entireties). The results have indeed confirmed that the IL-23 gene product can act as an adjuvant during BCG vaccination; however, while these findings are encouraging, the feasibility of mass administration of genes or their recombinant products is questionable, given the cost involved, the possibility of triggering neutralizing antibodies or allergic responses and lingering concerns about the safety of gene delivery.

SUMMARY OF THE INVENTION

The present invention provides compositions and methods for inducing an immune response in a subject. In particular, the present invention provides compositions comprising immunostimulatory ligands (ISL) and methods of inducing an immune response in a subject therewith. Compositions and methods of the present invention find use in, among other things, clinical (e.g. therapeutic and preventative medicine (e.g., vaccination)) and research applications.

Accordingly, in some embodiments, the invention provides a composition (e.g., immunogenic composition) comprising one or more immunostimulatory ligands (ISLs) alone or in the context of another molecule (e.g., a peptide, protein, polysaccharide, oligosaccharide, carbohydrate, and/or carbohydrate-containing molecule). In preferred embodiments, an ISL comprises the motif Q/K-K/R-R-A-A (SEQ ID NO.: 1) (e.g., QKRAA (SEQ ID NO.:2), QRRAA (SEQ ID NO.:3), KKRAA (SEQ ID NO.:4) or KRRAA (SEQ ID NO.:5)) or Q/R-K/R-R-A-A (SEQ ID NO.:6) (e.g., RKRAA (SEQ ID NO.: 13) and RRRAA (SEQ ID NO.: 14)). The present invention is not limited by a particular formulation of a composition (e.g., immunogenic composition) comprising an ISL or by a specific type of ISL. In some embodiments, ISL and/or protein or peptide comprising an ISL is a soluble ISL and/or soluble protein or peptide comprising an ISL. In some embodiments, ISL and/or protein or peptide comprising an ISL is in the form of a human leukocyte antigen (HLA) tetramer. In some embodiments, ISL and/or protein or peptide comprising an ISL is in the form of a cell bound surface protein and/or peptide (e.g., a cell surface marker protein and/or peptide). In some embodiments, ISL and/or protein or peptide comprising an ISL is in the form of a cell surface antigen. In a preferred embodiment, the ISL is a recombinant peptide and/or protein. In a further preferred embodiment, the ISL is a cyclic peptide or protein comprising a sequence selected from SEQ ID NOS. 1-6, 13 and 14. The invention is not limited by the method or procedure utilized to generate a cyclic ISL peptide and/or protein. Indeed, a variety of methods may be utilized including, but not limited to, a urea backbone cyclic protocol (See, e.g., Hurevich et al., Journal of Peptide Science 2010, 16, 178), an amide backbone-to-side chain cyclic peptides synthesis scheme (e.g., using microwave heating synthesis (See, e.g., Hayouka et al. 2011)), other known cyclization methods (e.g., disclosed in Gilon et al. Biopolymers 1991, 31: 745-50), or a combination thereof. In some embodiments, the ISL is present in a biologically active protein or peptide (e.g., a protein or peptide displaying antigenic or immunogenic properties (e.g., capable of inducing an immune response in a subject administered the peptide)). The peptide or protein may have antigenic or immunogenic characteristics in the absence of the ISL, or, may have no antigenic or immunogenic properties in the absence of the ISL but when the ISL is introduced into the protein or peptide the protein or peptide displays antigenic or immunogenic properties. The invention is not limited by the type of peptide. Indeed, a peptide containing an ISL of the invention may be any peptide described herein. In some embodiments, the peptide or protein is derived from a tumor or cancer protein. In some embodiment, a peptide or protein (e.g., recombinantly produced peptide or protein) containing an ISL of the invention is generated using a backbone cyclization (BC) strategy and/or method (See, Example 5). Thus, in some embodiments, the cyclic peptide is a conformationally intact peptidomimetic ISL. The invention is not limited by the length of a peptide, protein, polysaccharide, oligosaccharide, carbohydrate, and/or carbohydrate-containing molecule sequence which harbours an ISL. In some embodiments, a recombinant peptide and/or protein is engineered to contain an ISL. The peptide or protein may be from any microbe such as a bacteria, virus, fungi, yeast or the like. In some embodiments, the protein or peptide is from *Staphylococcus aureus; Staphylococcus epidermidis; Enterococcus faecalis; Mycobacterium tuberculosis; Streptococcus* group B; *Streptoccocus pneumoniae; Helicobacter pylori; Neisseria gonorrhea; Streptococcus* group A; *Borrelia burgdorferi; Coccidiodes immitis; Histoplasma sapsulatum; Neisseria meningitidis* type B; *Shigella flexneri; Escherichia coli; Haemophilus influenzae,* bacteria of the strain or genus *Klebsiella, Mycoplasma, E. coli,* and/or *Mycobacterium.*

In some embodiments, the invention provides a method of inducing an immune response (e.g., innate and/or acquired immune response) in a subject comprising: administering to the subject a composition comprising an ISL (e.g., linear or cyclic peptide/ISL). In some embodiments, the composition comprises a peptide, polypeptide, or protein comprising an immunostimulatory ligand. In some embodiments, the immune response comprises expansion of Th17 cells. In some embodiments, the Th17 cells are pathogen-specific. In some embodiments, the immune response comprises inhibition of T regulatory cell differentiation or activity. In some embodiments, the immune response comprises enhanced nitric oxide signalling and/or enhanced production of IL-6. In some embodiments, the immune response is cancer and/or tumor specific (e.g., specific for a cancer epitope or a tumor epitope). In some embodiments, the subject suffers from cancer, is suspected of having cancer, or is at risk of developing cancer. In some embodiments, the subject suffers from an infectious disease, is suspected of having an infectious disease, or is at risk of contracting an infectious disease.

In other embodiments, an ISL of the invention comprising a linear or cyclic peptide and/or protein comprising a sequence selected from SEQ ID NOS. 1-6, 13 and 14 is used in the manufacture of a medicament (e.g., to act as an agonist or antagonist of share epitope-triggered signaling events (e.g., due to a particular conformation (e.g., α-helix conformation) of the peptide and/or protein) for the treatment and/or prevention of disease (e.g., autoimmune disease (e.g., rheumatoid arthritis)).

In some embodiments, ISL is an effective adjuvant during vaccination and/or booster immunization against pathogens and/or tumors. In some embodiments, ISL shifts the immune balance from tolerance toward a Th17-polarized response. In some embodiments, ISL is provided as an immune adjuvant during anti-infection or anti-tumor chemotherapy. In some embodiments, ISL is administered to a subject to treat or prevent infection by bacteria, protozoa and/or viruses. In some embodiments, ISL is administered to a subject to treat or prevent infection by bacteria, protozoa and/or viruses capable of escaping immune eradication by Treg-mediated immune dysregulation. In some embodiments, the present invention provides a simultaneous effect on Treg and Th17. In some embodiments, ISL does not trigger neutralizing antibodies or allergic reactions.

The invention also provides a method of inhibiting T cell tolerance in a subject comprising administering to the subject an effective dose of a composition comprising an isolated, recombinant immunostimulatory ligand (ISL), selected from the group consisting of SEQ ID NOS.: 1-6, 13 and 14 under conditions such that T cell tolerance is reduced in the subject. In some embodiments, the subject is selected from the group consisting of a subject suffering from cancer, suspected of having cancer, at risk of developing cancer, suffering from an infectious disease, suspected of having an infectious disease, or at risk of contracting an infectious disease.

In some embodiments, the invention provides a method of treating cancer in a subject comprising administering to the subject a composition comprising an ISL (e.g., to induce an innate or acquired (e.g., cancer specific) immune response in the subject). In some embodiments, ISL is administered to a subject therapeutically to treat known cancer within a subject. In some embodiments, ISL is administered to a subject prophylactically to prevent cancer developing in a subject (e.g. a subject at risk for cancer). In some embodiments, the present invention finds use (e.g. therapeutically or prophylactically) with any type of cancer (e.g. bladder, melanoma, breast, non-hodgkin lymphoma, colon, rectal, pancreatic, endometrial, prostate, kidney, skin (e.g. nonmelanoma), leukemia, thyroid, lung, etc.).

In some embodiments, the present invention provides a method of treating and/or preventing infection within a subject. In some embodiments, a subject is known or suspected of having an infection (e.g. bacterial, viral, etc.). In some embodiments, a subject is thought to be at risk for developing an infection (e.g. bacterial, viral, eukaryotic, etc.). In some embodiments, ISL is administered to a subject to heighten immune response when a subject is expected to become at risk for infection (e.g. during chemotherapy, travel, when immunocompromised by another disease).

In some embodiments, the present invention provides methods of administering ISL to a subject to treat or prevent a disease (e.g. cancer), infection, condition, etc. followed by testing the subject for the presence of the disease (e.g. cancer), infection, condition, etc. In some embodiments, the present invention provides methods of administering ISL to a subject to treat or prevent a disease (e.g. cancer), infection, condition, etc. followed by testing the subject for a change in the status of the disease (e.g. cancer), infection, condition, etc. In some embodiments, the present invention provides methods comprising testing a subject for the presence of a disease (e.g. cancer), infection, condition, etc. followed by administering ISL to a subject to treat or prevent the disease (e.g. cancer), infection, condition, etc. In some embodiments, the present invention provides a method comprising testing a subject for the presence of a disease (e.g. cancer), infection, condition, etc. followed by administering ISL to a subject to treat or prevent the disease (e.g. cancer), infection, condition, etc. followed by testing the subject for the presence of, or a change in the status of, the disease (e.g. cancer), infection, condition, etc.

BRIEF DESCRIPTION OF THE FIGURES

The specification may be better understood when read in conjunction with the accompanying drawings which are included by way of example and not by way of limitation.

DEFINITIONS

Figure 1:
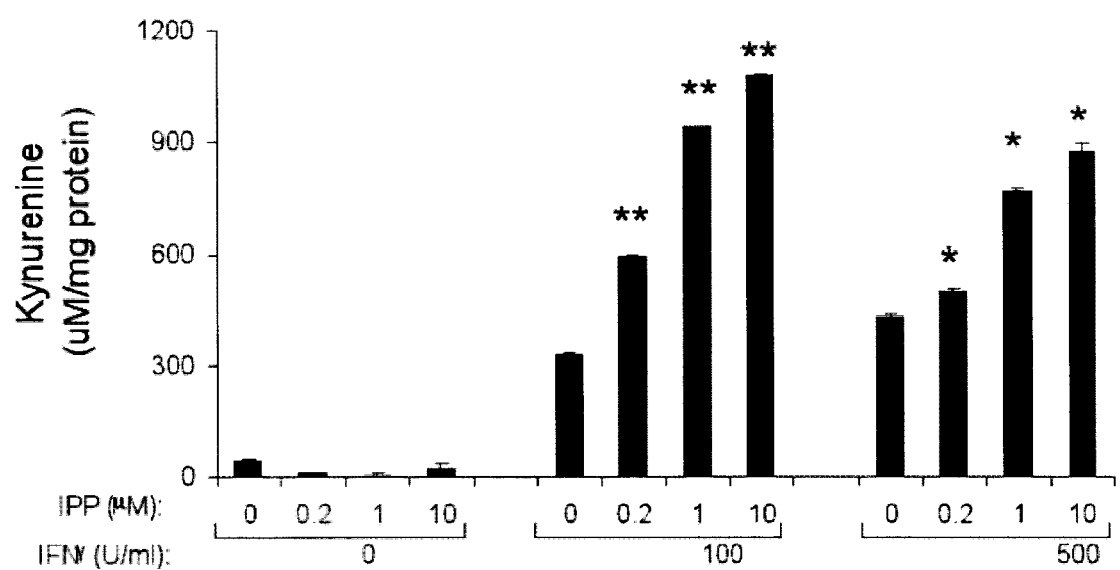
FIG. 1 shows a plot demonstrating synergism between IPP and IFN-γ. Human fibroblasts were preincubated overnight with various doses of IPP, followed by 48 h stimulation with various doses of rhIFN-γ. IDO activity was determined by quantifying kynurenine production.

To facilitate an understanding of the present invention, a number of terms and phrases are defined below:

As used herein, the term "microorganism" refers to any species or type of microorganism, including but not limited to, bacteria, viruses, archaea, fungi, protozoans, mycoplasma, prions, and parasitic organisms. The term microorganism encompasses both those organisms that are in and of themselves pathogenic to another organism (e.g., animals, including humans, and plants) and those organisms that produce agents that are pathogenic to another organism, while the organism itself is not directly pathogenic or infective to the other organism.

As used herein the term "pathogen," and grammatical equivalents, refers to an organism (e.g., biological agent), including microorganisms, that causes a disease state (e.g., infection, pathologic condition, disease, etc.) in another organism (e.g., animals and plants) by directly infecting the other organism, or by producing agents that causes disease in another organism (e.g., bacteria that produce pathogenic toxins and the like). "Pathogens" include, but are not limited to, viruses, bacteria, archaea, fungi, protozoans, mycoplasma, prions, and parasitic organisms.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc.

As used herein, the term "fungi" is used in reference to eukaryotic organisms such as molds and yeasts, including dimorphic fungi.

As used herein the terms "disease" and "pathologic condition" are used interchangeably, unless indicated otherwise herein, to describe a deviation from the condition regarded as normal or average for members of a species or group (e.g., humans), and which is detrimental to an affected individual under conditions that are not inimical to the majority of individuals of that species or group. Such a deviation can manifest as a state, signs, and/or symptoms (e.g., diarrhea, nausea, fever, pain, blisters, boils, rash, immune suppression, inflammation, etc.) that are associated with any impairment of the normal state of a subject or of any of its organs or tissues that interrupts or modifies the performance of normal functions. A disease or pathological condition may be caused by or result from contact with a microorganism (e.g., a pathogen or other infective agent (e.g., a virus or bacteria)), may be responsive to environmental factors (e.g., malnutrition, industrial hazards, and/or climate), may be responsive to an inherent defect of the organism (e.g., genetic anomalies) or to combinations of these and other factors.

The terms "host" or "subject," as used herein, refer to an individual to be treated by (e.g., administered) the compositions and methods of the present invention. Subjects include, but are not limited to, mammals (e.g., murines, simians, equines, bovines, porcines, canines, felines, and the like), and most preferably includes humans. In the context of the invention, the term "subject" generally refers to an individual who will be administered or who has been administered one or more compositions of the present invention (e.g., a composition for inducing an immune response (e.g., comprising ISL).

As used herein, the terms "a composition for inducing an immune response", "immunogenic composition" and grammatical equivalents refer to a composition that, once administered to a subject (e.g., once, twice, three times or more (e.g., separated by weeks, months or years)), stimulates, generates and/or elicits an immune response in the subject (e.g., resulting in total or partial immunity to a microorganism (e.g., pathogen) capable of causing disease). In preferred embodiments of the invention, the composition comprises ISL (e.g., purified (e.g., synthetic, recombinant, or otherwise isolated)) or derivatives or analogues thereof (e.g., cyclic mimetic ISL fragments). In further preferred embodiments, the composition comprising ISL comprises one or more other compounds or agents including, but not limited to, therapeutic agents, physiologically tolerable liquids, gels, carriers, diluents, adjuvants, excipients, salicylates, steroids, immunosuppressants, immunostimulants, antibodies, cytokines, antibiotics, binders, fillers, preservatives, stabilizing agents, emulsifiers, and/or buffers. An immune response may be an innate (e.g., a non-specific) immune response or a learned (e.g., acquired (e.g., cellular or humoral) immune response (e.g., that decreases the infectivity, morbidity, or onset of mortality in a subject (e.g., caused by exposure to a pathogenic microorganism), that prevents infectivity, pathology, morbidity, or onset of mortality in a subject (e.g., caused by exposure to a pathogenic microorganism), or that decreases tolerance (e.g., to a tumor antigen) in a subject). Thus, in some preferred embodiments, an immunogenic composition comprising ISL is administered to a subject to induce an immune response (e.g., as a vaccine (e.g., to prevent or attenuate a disease (e.g., by providing to the subject total or partial immunity against the disease or the total or partial attenuation (e.g., suppression) of a sign, symptom or condition of the disease))).

As used herein, the term "adjuvant" refers to any substance that can stimulate an immune response. Some adjuvants can cause activation of a cell of the immune system (e.g., an adjuvant can cause an immune cell to produce and secrete a cytokine).

As used herein, the terms "an amount effective to induce an immune response" and "effective amount" (e.g., of a composition for inducing an immune response), refers to the dosage level required (e.g., when administered to a subject) to stimulate, generate and/or elicit an immune response in the subject. An effective amount can be administered in one or more administrations (e.g., via the same or different route), applications or dosages and is not intended to be limited to a particular formulation or administration route.

As used herein, the term "under conditions such that said subject generates an immune response" refers to any condition that leads to a qualitative or quantitative induction, generation, and/or stimulation of an immune response (e.g., innate or acquired).

A used herein, the term "immune response" refers to any detectable response by the immune system of a subject. For example, immune responses include, but are not limited to, an alteration (e.g., increase) in Toll receptor activation, lymphokine (e.g., cytokine (e.g., Th1, Th2 or Th17 type cytokines) or chemokine) expression and/or secretion, macrophage activation, dendritic cell activation, T cell (e.g., CD4+ or CD8+ T cell) activation, NK cell activation, and/or B cell activation (e.g., antibody generation and/or secretion). Additional examples of immune responses include binding of an immunogen (e.g., antigen (e.g., immunogenic polypeptide)) to an MHC molecule and induction of a cytotoxic T lymphocyte ("CTL") response, induction of a B cell response (e.g., antibody production), and/or T-helper lymphocyte response, and/or a delayed type hypersensitivity (DTH) response (e.g., against the antigen from which an immunogenic polypeptide is derived), expansion (e.g., growth of a population of cells) of cells of the immune system (e.g., T cells, B cells (e.g., of any stage of development (e.g., plasma cells), and increased processing and presentation of antigen by antigen presenting cells. An immune response may be to immunogens that the subject's immune system recognizes as foreign (e.g., non-self antigens from microorganisms (e.g., pathogens), or self-antigens recognized as foreign). Thus, it is to be understood that, as used herein, "immune response" refers to any type of immune response, including, but not limited to, innate immune responses (e.g., activation of Toll receptor signaling cascade) cell-mediated immune responses (e.g., responses mediated by T cells (e.g., antigen-specific T cells) and non-specific cells of the immune system) and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to an antigen and/or immunogen (e.g., both the initial response to an immunogen (e.g., a pathogen) as well as acquired (e.g., memory) responses that are a result of an adaptive immune response).

As used herein, the term "immunity" refers to protection from disease (e.g., preventing or attenuating (e.g., suppression of) a sign, symptom or condition of the disease) upon exposure to a microorganism (e.g., pathogen) capable of causing the disease. Immunity can be innate (e.g., non-adaptive (e.g., non-acquired) immune responses that exist in the absence of a previous exposure to an antigen) and/or acquired (e.g., immune responses that are mediated by B and T cells following a previous exposure to antigen (e.g., that exhibit increased specificity and reactivity to the antigen)).

As used herein, the term "immunogen" refers to an agent (e.g., a microorganism (e.g., bacterium, virus or fungus) or portion thereof)) that is capable of eliciting an immune response in a subject. In preferred embodiments, immunogens elicit immunity against the immunogen (e.g., microorganism (e.g., pathogen) or portion thereof (e.g., an antigen)) when administered in combination with ISL of the present invention.

As used herein, the term "pathogen product" refers to any component or product derived from a pathogen including, but not limited to, polypeptides, peptides, proteins, nucleic acids, membrane fractions, and polysaccharides. Pathogen product include recombinant and synthetic agents.

As used herein, the term "enhanced immunity" refers to an increase in the level of adaptive and/or acquired immunity in a subject to a given immunogen and/or antigen (e.g., microorganism (e.g., pathogen)) following administration of a composition (e.g., composition for inducing an immune response of the present invention) relative to the level of adaptive and/or acquired immunity in a subject that has not been administered the composition (e.g., composition for inducing an immune response of the present invention).

As used herein, the term "cytokine" refers to immune system proteins that are biological response modifiers. They coordinate antibody and T-cell immune system interactions, and amplify immune reactivity. Cytokines include monokines synthesised by macrophages and lymphokines produced by activated T lymphocytes and natural killer cells. Monokines include interleukin (IL)-1, tumor necrosis factor (TNF), $\alpha$- and $\beta$-interferon (IFN), and colony-stimulating factors. Lymphokines include IL's, $\gamma$-IFN, granulocyte-macrophage colony-stimulating factor (GM-CSF), and lymphotoxin.

Endothelial cells and fibroblasts and selected other cell types may also synthesise cytokines. Examples of cytokines include IL-2, IL-4, IL-13, IL-17, GM-CSF, IFN-γ, Flt-31, SCF, TNF-α.

As used herein, the terms "host," "subject" and "patient" refer to any animal, including but not limited to, human and non-human animals (e.g. rodents, arthropods, insects (e.g., Diptera), fish (e.g., zebrafish), non-human primates, ovines, bovines, ruminants, lagomorphs, porcines, caprines, equines, canines, felines, ayes, etc.), that is studied, analyzed, tested, diagnosed or treated. As used herein, the terms "host," "subject" and "patient" are used interchangeably.

The term "isolated" when used in relation to a protein as in "isolated protein" refers to a protein or protein sequence (e.g., a polypeptide sequence) that is identified and separated from at least one contaminant protein with which it is ordinarily associated in its natural source. Isolated protein is present in a form or setting that is different from that in which it is found in nature. In contrast, non-isolated proteins and/or polypeptides are found in the state they exist in nature.

The term "recombinant" when made in reference to a protein or a polypeptide refers to a protein molecule which is expressed using a recombinant nucleic acid molecule. A recombinant nucleic acid molecule refers to a nucleic acid molecule which is comprised of segments of nucleic acid joined together by means of molecular biological techniques.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

As used herein, the term "effective amount" refers to the amount of a composition (e.g., comprising ISL and/or peptide or protein comprising ISL) sufficient to effect beneficial or desired results. An effective amount can be administered in one or more administrations, applications or dosages and is not intended to be limited to a particular formulation or administration route. As used herein, the term "a therapeutically effective amount" of a composition comprising ISL and/or peptide or protein comprising ISL is herein defined as the dosage level/amount required to achieve a therapeutically beneficial result in a subject (e.g., that induces an immune response in the subject).

As used herein, the terms "administration" and "administering" refer to the act of giving a drug, prodrug, or other agent, or therapeutic treatment (e.g., compositions of the present invention) to a subject (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, rectal, by injection (e.g., intravenously, subcutaneously, intratumorally, intraperitoneally, etc.) and the like.

As used herein, the term "autologous cells" refers to cells that are a subject's own cells.

As used herein, the term "allogeneic cells" refers cells which are genetically different, but of the same species.

DETAILED DESCRIPTION

The present invention provides compositions and methods for inducing an immune response in a subject. In particular, the present invention provides compositions comprising immunostimulatory ligands (ISL) and methods of inducing an immune response in a subject therewith. Compositions and methods of the present invention find use in, among other things, clinical (e.g. therapeutic and preventative) medicine.

Accordingly, the invention provides a composition (e.g., immunogenic composition) comprising one or more immunostimulatory ligands (herein referred to as "ISLs") alone or in the context of another molecule (e.g., a peptide, protein, polysaccharide, oligosaccharide, carbohydrate, and/or carbohydrate-containing molecule). As used herein, the terms "immunostimulatory ligand," "ISL," "immunostimulatory ligands" or "ISLs") refer to a peptide comprising an amino acid sequence comprising the motif Q/K-K/R-R-A-A (SEQ ID NO.: 1) (e.g., QKRAA (SEQ ID NO.:2), QRRAA (SEQ ID NO.:3), KKRAA (SEQ ID NO.:4) or KRRAA (SEQ ID NO.:5)) or Q/R-K/R-R-A-A (SEQ ID NO.:6) (e.g., RKRAA (SEQ ID NO.: 13) and RRRAA (SEQ ID NO.: 14)). The present invention is not limited by a particular formulation of a composition (e.g., immunogenic composition) comprising an ISL or by a specific type of ISL (See, e.g., Examples 1-5). In some embodiments, ISL and/or protein or peptide comprising an ISL is a soluble ISL and/or soluble protein or peptide comprising an ISL. In some embodiments, ISL and/or protein or peptide comprising an ISL is in the form of a human leukocyte antigen (HLA) tetramer. In some embodiments, ISL and/or protein or peptide comprising an ISL is in the form of a cell bound surface protein and/or peptide (e.g., a cell surface marker protein and/or peptide). In some embodiments, ISL and/or protein or peptide comprising an ISL is in the form of a cell surface antigen.

In some embodiments, the ISL is present in a biologically active protein or peptide (e.g., a protein or peptide displaying antigenic or immunogenic properties (e.g., capable of inducing an immune response in a subject administered the peptide)). The peptide or protein may have antigenic or immunogenic characteristics in the absence of the ISL, or, may have no antigenic or immunogenic properties in the absence of the ISL but when the ISL is introduced into the protein or peptide the protein or peptide displays antigenic or immunogenic properties. The invention is not limited by the type of peptide. Indeed, a peptide containing an ISL of the invention may be any peptide described herein. In some embodiment, a peptide or protein (e.g., recombinantly produced peptide or protein) containing an ISL of the invention is generated using a backbone cyclization (BC) strategy (See, Example 5). The invention is not limited by the method or procedure utilized to generate a cyclic ISL peptide and/or protein. Indeed, a variety of methods may be utilized including, but not limited to, a urea backbone cyclic protocol (See, e.g., Hurevich et al., Journal of Peptide Science 2010, 16, 178), an amide backbone-to-side chain cyclic peptides synthesis scheme (e.g., using microwave heating synthesis (See, e.g., Hayouka et al. 2011)), peptide stapling methods (See, e.g., Walensky et al., Science 2004, 305, 1466; Stewart et al., Nature Chemical Biology 2010, 6, 595) other known methods (See, e.g., Gilon et al. Biopolymers 1991, 31: 745-50), or a combination thereof. In a preferred embodiment, the ISL is a recombinant peptide and/or protein. In a further preferred embodiment, the ISL is a cyclic peptide or protein comprising a sequence selected from SEQ ID NOS. 1-6, 13 and 14.

The invention provides multiple examples of cyclic peptides that are metabolically stable, selective (e.g., due to peptide conformation), and/or that are bioavailable. In some embodiments, the cyclic peptides are in fast equilibrium among many conformations in solution with no single restricted conformation. In a preferred embodiment, the invention provides cyclic peptides, that retain the biological activity of their parent linear peptides, that also possess desirable pharmacological properties (See, e.g., Example 5). For example, the invention provides cyclic peptides that activate nitric oxide (NO) production in the low nM range. Although an understanding of the mechanism is not needed to practice the invention, and the invention is not limited to any particular mechanism of action, in some embodiments, a biologically active cyclic peptide of the invention possesses a stable α-helix conformation that contains the SE consensus motif. As described herein, in some embodiments, the activity of the cyclic peptide can be modified (e.g., the ability of the peptide to induce NO production and/or signaling events can be altered) based upon the conformation of the peptide generated (e.g., based upon the ring size generated using a cyclization method described herein). For example, in some embodiments, the invention provides methods of generating and characterizing cyclic peptides encompassing all types of peptides including linear peptides as well as peptides that possess secondary, tertiary and/or quaternary structures (e.g., that possess α-helix conformation and/or β-turn conformations). In some embodiments, peptides and/or proteins of the invention are utilized as agonists (e.g., to induce NO production and/or signaling events (e.g., utilizing a peptide and/or protein of the invention that possesses a desired conformation (e.g., a secondary or higher structure conformation important for biologic activity (e.g. for dimerization or coupling to target protein). In other embodiments, peptides and/or proteins of the invention are utilized as antagonists (e.g., to block immune system activity (e.g. NO production and/or signaling events (e.g., utilizing a peptide and/or protein of the invention that possesses a desired conformation (e.g., a conformation that impedes the activity of normal biologic activity (e.g. that blocks dimerization or coupling to target protein(s))))).

Thus, in some embodiments, the cyclic peptide is a conformationally intact peptidomimetic ISL. The invention is not limited by the length of a peptide, protein, polysaccharide, oligosaccharide, carbohydrate, and/or carbohydrate-containing molecule sequence which harbours an ISL. In some embodiments, a recombinant peptide and/or protein is engineered to contain an ISL. The peptide or protein may be from any microbe such as a bacteria, virus, fungi, yeast or the like. In some embodiments, the protein or peptide is from *Staphylococcus aureus; Staphylococcus epidermidis; Enterococcus faecalis; Mycobacterium tuberculosis; Streptococcus* group B; *Streptoccocus pneumoniae; Helicobacter pylori; Neisseria gonorrhea; Streptococcus* group A; *Borrelia burgdorferi; Coccidiodes immitis; Histoplasma sapsulatum; Neisseria meningitidis* type B; *Shigella flexneri; Escherichia coli; Haemophilus influenzae*, bacteria of the strain or genus *Klebsiella, Mycoplasma, E. coli*, and/or *Mycobacterium*.

In a preferred embodiment, the protein or peptide containing an ISL is from a pathogen (e.g., bacteria or virus) to which a Th17 type immune response is beneficial in the clearance of the pathogen from a host. For example, in some embodiments the protein or peptide is from a bacteria of the strain or genus *Klebsiella, Mycoplasma, E. coli*, and/or *Mycobacterium*. In another preferred embodiment, the protein or peptide containing an ISL is a tumor antigen or a cancer antigen. The invention is not limited to any particular tumor or cancer antigen. Indeed, an ISL may be utilized with any tumor or cancer antigen known in the art (e.g., to make the tumor or cancer antigen antigenic and/or immunogenic (e.g., in order to overcome immune evasion characteristics of the tumor and/or cancer)). In some embodiments, an immunogenic composition of the invention comprises an ISL in the context of a recombinant or isolated protein or peptide which comprises an amino acid sequence which has at least 85% identity, preferably at least 90% identity, more preferably at least 95% identity, most preferably at least 97-99% or exact identity, to that of a sequence found in its native state in a host organism (e.g., a cancer or tumor antigen and/or a protein or polypeptide of a microorganism). Peptides or proteins may be native or recombinant, full-length protein or optionally a mature protein in which any signal sequence has been removed. The protein may be isolated directly from a sample (e.g., a microorganism or tumor) or produced by recombinant DNA techniques. Immunogenic fragments of a protein or peptide containing an ISL may be incorporated into an immunogenic composition of the invention. The invention is not limited by the length of polypeptide or protein containing an ISL. For example, in some embodiments a protein or polypeptide containing ISL comprises at least 5 amino acids, 10 amino acids, preferably 20 amino acids, more preferably 30 amino acids, more preferably 40 amino acids or 50 amino acids, more preferably 100 or more amino acids, taken contiguously from the amino acid sequence of a protein. A protein or polypeptide containing ISL include proteins or polypeptides that when administered at an effective dose, (e.g., either alone or together with a pharmaceutically acceptable carrier and/or adjuvant), elicit a protective immune response against the host microorganism and/or tumor from which the protein and/or polypeptide is derived, and more preferably, such immune response is protective (e.g., prophylactically and/or therapeutically) against infection caused by the microorganism and/or disease caused by the tumor and/or cancer. In some embodiments, a protein or polypeptide containing ISL is immunologically reactive with antibodies generated against the microorganism and/or tumor or cancer or with antibodies generated by infection of a mammalian host with the microorganism. In some embodiments, a protein or polypeptide containing ISL contains one or more T cell epitopes.

In an embodiment, immunogenic compositions of the invention may contain fusion proteins of a protein or polypeptide containing ISL proteins. Such fusion proteins may be made recombinantly and may comprise one portion of at least 2, 3, 4, 5, 6 or more proteins or polypeptides (e.g., from a microorganism and/or tumor/cancer). Alternatively, a fusion protein may comprise multiple portions of at least 2, 3, 4, or 5 proteins/peptides. These may combine different proteins or fragments thereof in the same protein. Alternatively, the invention also includes individual fusion proteins of proteins or fragments thereof, as a fusion protein with heterologous sequences such as a provider of T-cell epitopes or purification tags, for example: β-galactosidase, glutathione-S-transferase, green fluorescent proteins (GFP), epitope tags such as FLAG, myc tag, poly histidine, or viral surface proteins such as influenza virus haemagglutinin, or bacterial proteins such as tetanus toxoid, diphtheria toxoid, and/or CRM197.

The invention is not limited by a particular formulation of a composition (e.g., immunogenic composition) comprising an ISL or by a specific type of ISL. In some embodiments, a protein or peptide comprises an amino acid sequence comprising the motif Q/K-K/R-R-A-A (SEQ ID NO.: 1). In some embodiments, an ISL comprises the sequence QKRAA (SEQ ID NO.:2). In some embodiments, an ISL comprises the sequence QRRAA (SEQ ID NO.:3). In some embodiments, an ISL comprises the sequence KKRAA (SEQ ID NO.:4). In some embodiments, an ISL comprises the sequence KRRAA (SEQ ID NO.:5). In some embodiments, an ISL comprises the sequence Q/R-K/R-R-A-A (SEQ ID NO.:6) (e.g., RKRAA (SEQ ID NO.: 13) and RRRAA (SEQ ID NO.: 14)). In some embodiments, a protein or peptide comprises a cyclic peptide (e.g., generated using a backbone cyclization (BC) strategy) comprising the sequence Q/K-K/R-R-A-A (SEQ ID NO.: 1) (e.g., QKRAA (SEQ ID NO.:2), QRRAA (SEQ ID NO.:3), KKRAA (SEQ ID NO.:4) or KRRAA (SEQ ID NO.:5)) or Q/R-K/R-R-A-A (SEQ ID NO.:6) (e.g., RKRAA (SEQ ID NO.: 13) and RRRAA (SEQ ID NO.: 14)).

In some embodiments, the invention provides one or more ISLs and methods of inducing an immune response (e.g., innate and/or adaptive immune responses) in a subject therewith. In some embodiments, administration of a composition comprising ISL and/or a peptide or protein containing an ISL of the invention generates an innate immune response (e.g., activates Toll-like receptor signaling and/or activation of NF-kB) in a subject.

Although an understanding of a mechanism of action is not necessary to practice the invention, and the invention is not limited to any particular mechanism of action, in some embodiments, compositions (e.g. comprising an ISL) inhibit indoleamine 2,3 dioxygenase (IDO) and/or stimulate production of IL-6. IL-6 is a regulatory T cell (Treg)-inhibitory cytokine with Th17-polarizing activity. Thus, in some embodiments, the invention provides compositions (e.g. comprising an ISL) and methods of using the same to inhibit Treg-inducing signals and/or to stimulate Th17-cell differentiation (e.g., ISL is utilized to potentiate Th17 differentiating (e.g. activating) signals in a subject via administering ISL and/or a peptide or protein containing an ISL to the subject (See, e.g., Examples 1-4)). The invention also provides a composition comprising ISL and/or protein or peptide comprising an ISL and methods of using the same to inhibit T cell tolerance in a subject (e.g., to inhibit tolerance to a tumor and/or cancer present in a subject (e.g., via administering a composition comprising ISL and/or protein or peptide comprising an ISL to a subject with cancer and/or a tumor). In some embodiments, administration of a composition comprising ISL and/or a peptide or protein containing an ISL of the invention to a subject inhibits T regulatory cell activity and/or differentiation in the subject.

A preferred embodiment of the invention is a method of preventing or treating cancer and/or tumor growth or spread comprising the step of administering an immunogenic composition or vaccine of the invention to a patient in need thereof. In one embodiment, the patient is awaiting elective surgery. Another embodiment of the invention is a use of the immunogenic composition of the invention in the manufacture of a vaccine for treatment or prevention of cancer and/or tumor metastasis (e.g., post-surgical treatment).

A composition (e.g., immunogenic composition) comprising one or more ISLs and/or a composition (e.g., immunogenic composition) comprising a protein or peptide comprising an ISL of the invention may comprise one or more different agents in addition to the one or more ISLs and/or protein or peptide comprising an ISL. These agents or cofactors include, but are not limited to, adjuvants, surfactants, additives, buffers, solubilizers, chelators, oils, salts, therapeutic agents, drugs, bioactive agents, antibacterials, and antimicrobial agents (e.g., antibiotics, antivirals, etc.). In some embodiments, a composition comprising one or more ISLs and/or protein or peptide comprising an ISL of the invention comprises an agent and/or co-factor that enhance the ability of the one or more ISLs and/or protein or peptide comprising an ISL to induce an immune response (e.g., an adjuvant). In some preferred embodiments, the presence of one or more co-factors or agents reduces the amount of ISL and/or protein or peptide comprising an ISL required for induction of an immune response (e.g., a protective immune response (e.g., protective immunization)). In some embodiments, the presence of one or more co-factors or agents can be used to skew the immune response towards a cellular (e.g., T cell mediated) or humoral (e.g., antibody mediated) immune response. The present invention is not limited by the type of co-factor or agent used in a therapeutic agent of the present invention. In some embodiments, the co-factor or agent is a drug or therapeutic used for cancer treatment and/or therapy known in the art. In a preferred embodiment, a therapeutically effective amount of a composition comprising ISL and/or peptide or protein comprising an ISL is administered to a subject.

Adjuvants are described in general in Vaccine Design—the Subunit and Adjuvant Approach, edited by Powell and Newman, Plenum Press, New York, 1995. The present invention is not limited by the type of adjuvant utilized (e.g., for use in a composition (e.g., pharmaceutical composition) comprising ISL and/or protein or peptide comprising an ISL). For example, in some embodiments, suitable adjuvants include an aluminium salt such as aluminium hydroxide gel (alum) or aluminium phosphate. In some embodiments, an adjuvant may be a salt of calcium, iron or zinc, or may be an insoluble suspension of acylated tyrosine, or acylated sugars, cationically or anionically derivatised polysaccharides, or polyphosphazenes.

In some embodiments, it is preferred that a composition comprising ISL and/or protein or peptide comprising an ISL of the present invention comprises one or more adjuvants that induce a Th1-type response. However, in other embodiments, it will be preferred that a composition comprising a NE and immunogen of the present invention comprises one or more adjuvants that induce a Th2-type response. In another preferred embodiment, a composition comprising ISL and/or protein or peptide comprising an ISL of the present invention comprises one or more adjuvants that induce a Th17-type response In general, an immune response is generated to an antigen through the interaction of the antigen with the cells of the immune system. Immune responses may be broadly categorized into two categories: humoral and cell mediated immune responses (e.g., traditionally characterized by antibody and cellular effector mechanisms of protection, respectively). These categories of response have been termed Th1-type responses (cell-mediated response), and Th2-type immune responses (humoral response).

Stimulation of an immune response can result from a direct or indirect response of a cell or component of the immune system to an intervention (e.g., exposure to an immunogen). Immune responses can be measured in many ways including activation, proliferation or differentiation of cells of the immune system (e.g., B cells, T cells, dendritic cells, APCs, macrophages, NK cells, NKT cells etc.); up-regulated or down-regulated expression of markers and cytokines; stimulation of IgA, IgM, or IgG titer; splenomegaly (including increased spleen cellularity); hyperplasia and mixed cellular infiltrates in various organs. Other responses, cells, and components of the immune system that can be assessed with respect to immune stimulation are known in the art.

Although an understanding of the mechanism is not necessary to practice the present invention and the present invention is not limited to any particular mechanism of action, in some embodiments, compositions and methods of the present invention induce expression and secretion of cytokines (e.g., by macrophages, dendritic cells and/or CD4+ T cells). Modulation of expression of a particular cytokine can occur locally or systemically. It is known that cytokine profiles can determine T cell regulatory and effector functions in immune responses. In some embodiments, Th1-type cytokines can be induced, and thus, the immunostimulatory compositions of the present invention can promote a Th1 type antigen-specific immune response including cytotoxic T-cells. However in other embodiments, Th2-type cytokines can be induced thereby promoting a Th2 type antigen-specific immune response. In a preferred embodiment, Th17-type cytokines are induced, and thus, the immunostimulatory compositions of the present invention promotes a Th17 type antigen-specific immune response including inhibition of T regulatory cell activity.

Cytokines play a role in directing the T cell response. Helper (CD4+) T cells orchestrate the immune response of mammals through production of soluble factors that act on other immune system cells, including B and other T cells. Most mature CD4+ T helper cells express one of two cytokine profiles: Th1 or Th2. Th1-type CD4+ T cells secrete IL-2, IL-3, IFN-γ, GM-CSF and high levels of TNF-α. Th2 cells express IL-3, IL-4, IL-5, IL-6, IL-9, IL-10, IL-13, GM-CSF and low levels of TNF-α. Th1 type cytokines promote both cell-mediated immunity, and humoral immunity that is characterized by immunoglobulin class switching to IgG2a in mice and IgG1 in humans. Th1 responses may also be associated with delayed-type hypersensitivity and autoimmune disease. Th2 type cytokines induce primarily humoral immunity and induce class switching to IgG1 and IgE. The antibody isotypes associated with Th1 responses generally have neutralizing and opsonizing capabilities whereas those associated with Th2 responses are associated more with allergic responses.

Several factors have been shown to influence skewing of an immune response towards either a Th1 or Th2 type response. The best characterized regulators are cytokines. IL-12 and IFN-γ are positive Th1 and negative Th2 regulators. IL-12 promotes IFN-γ production, and IFN-γ provides positive feedback for IL-12. IL-4 and IL-10 appear important for the establishment of the Th2 cytokine profile and to down-regulate Th1 cytokine production.

Thus, in some preferred embodiments, the present invention provides a method of stimulating a Th1-type immune response in a subject comprising administering to a subject a composition comprising ISL and/or protein or peptide comprising an ISL. However, in other preferred embodiments, the present invention provides a method of stimulating a Th2-type immune response in a subject comprising administering to a subject a composition comprising a ISL and/or protein or peptide comprising an ISL. In further preferred embodiments, adjuvants can be used (e.g., can be co-administered with a composition of the present invention) to skew an immune response toward either a Th1 or Th2 type immune response. For example, adjuvants that induce Th2 or weak Th1 responses include, but are not limited to, alum, saponins, and SB-As4. Adjuvants that induce Th1 responses include but are not limited to MPL, MDP, ISCOMS, IL-12, IFN-γ, and SB-AS2.

Several other types of Th1-type immunogens can be used (e.g., as an adjuvant) in compositions and methods of the present invention. These include, but are not limited to, the following. In some embodiments, monophosphoryl lipid A (e.g., in particular 3-de-O-acylated monophosphoryl lipid A (3D-MPL)), is used. 3D-MPL is a well known adjuvant manufactured by Ribi Immunochem, Montana. Chemically it is often supplied as a mixture of 3-de-O-acylated monophosphoryl lipid A with either 4, 5, or 6 acylated chains. In some embodiments, diphosphoryl lipid A, and 3-O-deacylated variants thereof are used. Each of these immunogens can be purified and prepared by methods described in GB 2122204B, hereby incorporated by reference in its entirety. Other purified and synthetic lipopolysaccharides have been described (See, e.g., U.S. Pat. No. 6,005,099 and EP 0 729 473; Hilgers et al., 1986, Int. Arch. Allergy. Immunol., 79(4): 392-6; Hilgers et al., 1987, Immunology, 60(1):141-6; and EP 0 549 074, each of which is hereby incorporated by reference in its entirety). In some embodiments, 3D-MPL is used in the form of a particulate formulation (e.g., having a small particle size less than 0.2 μm in diameter, described in EP 0 689 454, hereby incorporated by reference in its entirety).

In some embodiments, saponins are used as an immunogen (e.g., Th1-type adjuvant) in a composition of the present invention. Saponins are well known adjuvants (See, e.g., Lacaille-Dubois and Wagner (1996) Phytomedicine vol 2 pp 363-386). Examples of saponins include Quil A (derived from the bark of the South American tree Quillaja Saponaria Molina), and fractions thereof (See, e.g., U.S. Pat. No. 5,057,540; Kensil, Crit. Rev Ther Drug Carrier Syst, 1996, 12 (1-2):1-55; and EP 0 362 279, each of which is hereby incorporated by reference in its entirety). Also contemplated to be useful in the present invention are the haemolytic saponins QS7, QS17, and QS21 (HPLC purified fractions of Quil A; See, e.g., Kensil et al. (1991). J. Immunology 146, 431-437, U.S. Pat. No. 5,057,540; WO 96/33739; WO 96/11711 and EP 0 362 279, each of which is hereby incorporated by reference in its entirety). Also contemplated to be useful are combinations of QS21 and polysorbate or cyclodextrin (See, e.g., WO 99/10008, hereby incorporated by reference in its entirety.

In some embodiments, an immunogenic oligonucleotide containing unmethylated CpG dinucleotides ("CpG") is used as an adjuvant in the present invention. CpG is an abbreviation for cytosine-guanosine dinucleotide motifs present in DNA. CpG is known in the art as being an adjuvant when administered by both systemic and mucosal routes (See, e.g., WO 96/02555, EP 468520, Davis et al., J. Immunol, 1998, 160(2):870-876; McCluskie and Davis, J. Immunol., 1998, 161(9):4463-6; and U.S. Pat. App. No. 20050238660, each of which is hereby incorporated by reference in its entirety). For example, in some embodiments, the immunostimulatory sequence is Purine-Purine-C-G-pyrimidine-pyrimidine; wherein the CG motif is not methylated.

Although an understanding of the mechanism is not necessary to practice the present invention and the present invention is not limited to any particular mechanism of action, in some embodiments, the presence of one or more CpG oligonucleotides activate various immune subsets including natural killer cells (which produce IFN-γ) and macrophages. In some embodiments, CpG oligonucleotides are formulated into a composition of the present invention for inducing an immune response. In some embodiments, a free solution of CpG is co-administered together with an antigen (e.g., present within a NE solution (See, e.g., WO 96/02555; hereby incorporated by reference). In some embodiments, a CpG oligonucleotide is covalently conjugated to an antigen (See, e.g., WO 98/16247, hereby incorporated by reference), or formulated with a carrier such as aluminium hydroxide (See, e.g., Brazolot-Millan et al., Proc. Natl. Acad Sci., USA, 1998, 95(26), 15553-8 (e.g., ISL and/or protein or peptide comprising an ISL).

In some embodiments, adjuvants such as Complete Freunds Adjuvant and Incomplete Freunds Adjuvant, cytokines (e.g., interleukins (e.g., IL-2, IFN-γ, IL-4, IL-6, IL-17, IL-23, etc.), macrophage colony stimulating factor, tumor necrosis factor, etc.), detoxified mutants of a bacterial ADP-ribosylating toxin such as a cholera toxin (CT), a pertussis toxin (PT), or an E. Coli heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (See, e.g., WO93/13202 and WO92/19265, each of which is hereby incorporated by reference), and other immunogenic substances (e.g., that enhance the effectiveness of a composition of the present invention) are used with a composition comprising ISL and/or protein or peptide comprising an ISL of the present invention.

Additional examples of adjuvants that find use in the present invention include poly(di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and Leishmania elongation factor (a purified Leishmania protein; Corixa Corporation, Seattle, Wash.).

Adjuvants may be added to a composition comprising ISL and/or protein or peptide comprising an ISL, or, the adjuvant may be formulated with carriers, for example liposomes, or metallic salts (e.g., aluminium salts (e.g., aluminium hydroxide)) prior to combining with or co-administration with a composition comprising ISL and/or protein or peptide comprising an ISL.

In some embodiments, a composition comprising ISL and/or protein or peptide comprising an ISL comprises a single adjuvant. In other embodiments, a composition comprising ISL and/or protein or peptide comprising an ISL comprises two or more adjuvants (See, e.g., WO 94/00153; WO 95/17210; WO 96/33739; WO 98/56414; WO 99/12565; WO 99/11241; and WO 94/00153, each of which is hereby incorporated by reference in its entirety). In some embodiments, a composition comprising ISL and/or protein or peptide comprising an ISL of the present invention comprises one or more mucoadhesives (See, e.g., U.S. Pat. App. No. 20050281843, hereby incorporated by reference in its entirety). The present invention is not limited by the type of mucoadhesive utilized. Indeed, a variety of mucoadhesives are contemplated to be useful in the present invention including, but not limited to, cross-linked derivatives of poly(acrylic acid) (e.g., carbopol and polycarbophil), polyvinyl alcohol, polyvinyl pyrollidone, polysaccharides (e.g., alginate and chitosan), hydroxypropyl methylcellulose, lectins, fimbrial proteins, and carboxymethylcellulose. Although an understanding of the mechanism is not necessary to practice the present invention and the present invention is not limited to any particular mechanism of action, in some embodiments, use of a mucoadhesive (e.g., in a composition comprising ISL and/or protein or peptide comprising an ISL) enhances induction of an immune response in a subject (e.g., administered a composition of the present invention) due to an increase in duration and/or amount of exposure to an immunogen that a subject experiences when a mucoadhesive is used compared to the duration and/or amount of exposure to an immunogen in the absence of using the mucoadhesive.

In some embodiments, a composition of the present invention may comprise sterile aqueous preparations. Acceptable vehicles and solvents include, but are not limited to, water, Ringer's solution, phosphate buffered saline and isotonic sodium chloride solution. In addition, sterile, fixed oils are conventionally employed as a solvent or suspending medium. For this purpose any bland fixed mineral or non-mineral oil may be employed including synthetic mono-ordi-glycerides. In addition, fatty acids such as oleic acid find use in the preparation of injectables. Carrier formulations suitable for mucosal, subcutaneous, intramuscular, intraperitoneal, intravenous, or administration via other routes may be found in Remington's Pharmaceutical Sciences, Mack Publishing Company, Easton, Pa.

The invention provides compositions comprising ISL and/or protein or peptide comprising an ISL that possess a range of biologic activity (e.g., based upon the structure of the peptide and/or protein (e.g., linear, possessing secondary, tertiary and/or quaternary structure (e.g., α-helix and/or β-turn conformation that mimics a parent molecule or that blocks activity of a parent molecule))), as well as methods of generating and characterizing the same. Accordingly, in some embodiments, compositions and methods of the invention are utilized for the treatment and/or prevention of disease. The invention is not limited by the type of disease that may be treated and/or prevented utilizing a composition or method disclosed herein. In a preferred embodiment, the disease is an autoimmune disease. The invention is not limited by the type of autoimmune disease. Indeed, compositions and methods of the invention find use in a variety of autoimmune diseases including, but not limited to, rheumatoid arthritis, systemic lupus erythematosus (SLE), Cogan's syndrome, unclassified systemic autoimmune disease, Raynaud's syndrome, Wegener's granulomatosis, autoimmune uveoretinitis, autoimmune vasculitis, bullous pemphigus, myasthenia gravis, autoimmune thyroiditis or Hashimoto's disease, Sjogren's syndrome, granulomatous orchitis, autoimmune oophoritis, Crohn's disease, sarcoidosis, rheumatic carditis, ankylosing spondylitis, Grave's disease, or autoimmune thrombocytopenic purpura.

A composition comprising ISL and/or protein or peptide comprising an ISL (e.g., a cyclic peptide and/or protein generated using an ISL (e.g., cyclic or linear) of the invention) can be used therapeutically (e.g., to enhance an immune response (e.g., against a pathogen and/or a tumor or cancer) or to inhibit an immune response (e.g., using a non-biologically active peptide mimetic) or as a prophylactic (e.g., for immunization (e.g., to prevent signs or symptoms of disease)). A composition comprising ISL and/or protein or peptide comprising an ISL of the present invention can be administered to a subject via a number of different delivery routes and methods.

In some embodiments, compositions of the present invention are administered mucosally (e.g., using standard techniques; See, e.g., Remington: The Science and Practice of Pharmacy, Mack Publishing Company, Easton, Pa., 19th edition, 1995 (e.g., for mucosal delivery techniques, including intranasal, pulmonary, vaginal and rectal techniques), as well as European Publication No. 517,565 and Illum et al., J. Controlled Rel., 1994, 29:133-141 (e.g., for techniques of intranasal administration), each of which is hereby incorporated by reference in its entirety). Alternatively, the compositions of the present invention may be administered dermally or transdermally, using standard techniques (See, e.g., Remington: The Science arid Practice of Pharmacy, Mack Publishing Company, Easton, Pa., 19th edition, 1995). The present invention is not limited by the route of administration.

For example, the compositions of the present invention can be administered to a subject (e.g., mucosally (e.g., nasal mucosa, vaginal mucosa, etc.)) by multiple methods, including, but not limited to: being suspended in a solution and applied to a surface; being suspended in a solution and sprayed onto a surface using a spray applicator; being mixed with a mucoadhesive and applied (e.g., sprayed or wiped) onto a surface (e.g., mucosal surface); being placed on or impregnated onto a nasal and/or vaginal applicator and applied; being applied by a controlled-release mechanism; being applied as a liposome; or being applied on a polymer.

In some embodiments, a composition comprising ISL and/or protein or peptide comprising an ISL of the present invention may be used to protect or treat a subject susceptible to, or suffering from, disease by means of administering a composition of the present invention via a mucosal route (e.g., an oral/alimentary or nasal route). Alternative mucosal routes include intravaginal and intra-rectal routes. Methods of intranasal vaccination are well known in the art, including the administration of a droplet or spray form of the vaccine into the nasopharynx of a subject to be immunized. In some embodiments, a nebulized or aerosolized composition comprising ISL and/or protein or peptide comprising an ISL is provided. Enteric formulations such as gastro resistant capsules for oral administration, suppositories for rectal or vaginal administration also form part of this invention. Compositions of the present invention may also be administered via the oral route. Under these circumstances, a composition comprising ISL and/or protein or peptide comprising an ISL may comprise a pharmaceutically acceptable excipient and/or include alkaline buffers, or enteric capsules. Formulations for nasal delivery may include those with dextran or cyclodextran and saponin as an adjuvant.

Compositions of the present invention may also be administered via a vaginal route. In such cases, a composition comprising ISL and/or protein or peptide comprising an ISL may comprise pharmaceutically acceptable excipients and/or emulsifiers, polymers (e.g., CARBOPOL), and other known stabilizers of vaginal creams and suppositories. In some embodiments, compositions of the present invention are administered via a rectal route. In such cases, a composition comprising ISL and/or protein or peptide comprising an ISL may comprise excipients and/or waxes and polymers known in the art for forming rectal suppositories.

In some embodiments, the same route of administration (e.g., mucosal administration) is chosen for both a priming and boosting vaccination. In some embodiments, multiple routes of administration are utilized (e.g., at the same time, or, alternatively, sequentially) in order to stimulate an immune response (e.g., using a composition comprising ISL and/or protein or peptide comprising an ISL of the present invention).

For example, in some embodiments, a composition comprising ISL and/or protein or peptide comprising an ISL is administered to a mucosal surface of a subject in either a priming or boosting vaccination regime. Alternatively, in some embodiments, a composition comprising ISL and/or protein or peptide comprising an ISL is administered systemically in either a priming or boosting vaccination regime. In some embodiments, a composition comprising ISL and/or protein or peptide comprising an ISL is administered to a subject in a priming vaccination regimen via mucosal administration and a boosting regimen via systemic administration. In some embodiments, a composition comprising ISL and/or protein or peptide comprising an ISL is administered to a subject in a priming vaccination regimen via systemic administration and a boosting regimen via mucosal administration. Examples of systemic routes of administration include, but are not limited to, a parenteral, intramuscular, intradermal, transdermal, subcutaneous, intraperitoneal or intravenous administration. A composition comprising ISL and/or protein or peptide comprising an ISL may be used for both prophylactic and therapeutic purposes.

In some embodiments, compositions of the present invention are administered by pulmonary delivery. For example, a composition of the present invention can be delivered to the lungs of a subject (e.g., a human) via inhalation (e.g., thereby traversing across the lung epithelial lining to the blood stream (See, e.g., Adjei, et al. Pharmaceutical Research 1990; 7:565-569; Adjei, et al. Int. J. Pharmaceutics 1990; 63:135-144; Braquet, et al. J. Cardiovascular Pharmacology 1989 143-146; Hubbard, et al. (1989) Annals of Internal Medicine, Vol. III, pp. 206-212; Smith, et al. J. Clin. Invest. 1989; 84:1145-1146; Oswein, et al. "Aerosolization of Proteins", 1990; Proceedings of Symposium on Respiratory Drug Delivery II Keystone, Colo.; Debs, et al. J. Immunol. 1988; 140:3482-3488; and U.S. Pat. No. 5,284,656 to Platz, et al, each of which are hereby incorporated by reference in its entirety). A method and composition for pulmonary delivery of drugs for systemic effect is described in U.S. Pat. No. 5,451,569 to Wong, et al., hereby incorporated by reference; See also U.S. Pat. No. 6,651,655 to Licalsi et al., hereby incorporated by reference in its entirety)).

Further contemplated for use in the practice of this invention are a wide range of mechanical devices designed for pulmonary and/or nasal mucosal delivery of pharmaceutical agents including, but not limited to, nebulizers, metered dose inhalers, and powder inhalers, all of which are familiar to those skilled in the art. Some specific examples of commercially available devices suitable for the practice of this invention are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). All such devices require the use of formulations suitable for dispensing of the therapeutic agent. Typically, each formulation is specific to the type of device employed and may involve the use of an appropriate propellant material, in addition to the usual diluents, adjuvants, surfactants, carriers and/or other agents useful in therapy. Also, the use of liposomes, microcapsules or microspheres, inclusion complexes, or other types of carriers is contemplated.

Thus, in some embodiments, a composition comprising ISL and/or protein or peptide comprising an ISL of the present invention may be used to protect and/or treat a subject susceptible to, or suffering from, a disease by means of administering a compositions comprising ISL and/or protein or peptide comprising an ISL by mucosal, intramuscular, intraperitoneal, intradermal, transdermal, pulmonary, intravenous, subcutaneous or other route of administration described herein. Methods of systemic administration of an immunogenic composition comprising ISL and/or protein or peptide comprising an ISL may include conventional syringes and needles, or devices designed for ballistic delivery of solid vaccines (See, e.g., WO 99/27961, hereby incorporated by reference), or needleless pressure liquid jet device (See, e.g., U.S. Pat. No. 4,596,556; U.S. Pat. No. 5,993,412, each of which are hereby incorporated by reference), or transdermal patches (See, e.g., WO 97/48440; WO 98/28037, each of which are hereby incorporated by reference). The present invention may also be used to enhance the immunogenicity of antigens applied to the skin (transdermal or transcutaneous delivery, See, e.g., WO 98/20734; WO 98/28037, each of which are hereby incorporated by reference). Thus, in some embodiments, the present invention provides a delivery device for systemic administration, pre-filled with an immunogenic composition of the present invention.

The present invention is not limited by the type of subject administered (e.g., in order to stimulate an immune response (e.g., in order to generate protective immunity (e.g., mucosal and/or systemic immunity))) a composition of the present invention. Indeed, a wide variety of subjects are contemplated to be benefited from administration of a composition of the present invention. In preferred embodiments, the subject is a human. In another preferred embodiment, the subject is a subject displaying signs, symptoms or other characteristics of cancer (e.g., a subject diagnosed as having cancer). In some embodiments, human subjects are of any age (e.g., adults, children, infants, etc.) that have been or are likely to become exposed to a microorganism. In some embodiments, the general public is administered (e.g., vaccinated with) a composition of the present invention (e.g., to prevent the occurrence or spread of disease). For example, in some embodiments, compositions and methods of the present invention are utilized to vaccinate a group of people (e.g., a population of a region, city, state and/or country) for their own health (e.g., to prevent or treat disease) and/or to prevent or reduce the risk of disease spread from animals (e.g., birds, cattle, sheep, pigs, etc.) to humans. In some embodiments, the subjects are non-human mammals (e.g., pigs, cattle, goats, horses, sheep, or other livestock; or mice, rats, rabbits or other animal). In some embodiments, compositions and methods of the present invention are utilized in research settings (e.g., with research animals).

A composition of the present invention may be formulated for administration by any route, such as mucosal, oral, topical, parenteral or other route described herein. The compositions may be in any one or more different forms including, but not limited to, tablets, capsules, powders, granules, lozenges, foams, creams or liquid preparations.

Topical formulations of the present invention may be presented as, for instance, ointments, creams or lotions, foams, and aerosols, and may contain appropriate conventional additives such as preservatives, solvents (e.g., to assist penetration), and emollients in ointments and creams.

Topical formulations may also include agents that enhance penetration of the active ingredients through the skin. Exemplary agents include a binary combination of N-(hydroxyethyl)pyrrolidone and a cell-envelope disordering compound, a sugar ester in combination with a sulfoxide or phosphine oxide, and sucrose monooleate, decyl methyl sulfoxide, and alcohol.

Other exemplary materials that increase skin penetration include surfactants or wetting agents including, but not limited to, polyoxyethylene sorbitan mono-oleoate (Polysorbate 80); sorbitan mono-oleate (Span 80); p-isooctyl polyoxyethylene-phenol polymer (Triton WR-1330); polyoxyethylene sorbitan tri-oleate (Tween 85); dioctyl sodium sulfosuccinate; and sodium sarcosinate (Sarcosyl NL-97); and other pharmaceutically acceptable surfactants.

In certain embodiments of the invention, compositions may further comprise one or more alcohols, zinc-containing compounds, emollients, humectants, thickening and/or gelling agents, neutralizing agents, and surfactants. Water used in the formulations is preferably deionized water having a neutral pH. Additional additives in the topical formulations include, but are not limited to, silicone fluids, dyes, fragrances, pH adjusters, and vitamins.

Topical formulations may also contain compatible conventional carriers, such as cream or ointment bases and ethanol or oleyl alcohol for lotions. Such carriers may be present as from about 1% up to about 98% of the formulation. The ointment base can comprise one or more of petrolatum, mineral oil, ceresin, lanolin alcohol, panthenol, glycerin, bisabolol, cocoa butter and the like.

In some embodiments, pharmaceutical compositions of the present invention may be formulated and used as foams. Pharmaceutical foams include formulations such as, but not limited to, emulsions, microemulsions, creams, jellies and liposomes. While basically similar in nature these formulations vary in the components and the consistency of the final product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, preferably do not unduly interfere with the biological activities of the components of the compositions of the present invention. The formulations can be sterilized and, if desired, mixed with auxiliary agents (e.g., lubricants, preservatives, stabilizers, wetting agents, emulsifiers, salts for influencing osmotic pressure, buffers, colorings, flavorings and/or aromatic substances and the like) that do not deleteriously interact with the ISL and/or protein or peptide comprising an ISL of the formulation. In some embodiments, immunostimulatory compositions of the present invention are administered in the form of a pharmaceutically acceptable salt. When used the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric; nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include, but are not limited to, acetic acid and a salt (1-2% w/v); citric acid and a salt (1-3% w/v); boric acid and a salt (0.5-2.5% w/v); and phosphoric acid and a salt (0.8-2% w/v). Suitable preservatives may include benzalkonium chloride (0.003-0.03% w/v); chlorobutanol (0.3-0.9% w/v); parabens (0.01-0.25% w/v) and thimerosal (0.004-0.02% w/v). Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

In some embodiments, a composition comprising ISL and/or protein or peptide comprising an ISL is co-administered with one or more antibiotics. For example, one or more antibiotics may be administered with, before and/or after administration of a composition comprising ISL and/or protein or peptide comprising an ISL. The present invention is not limited by the type of antibiotic co-administered. Indeed, a variety of antibiotics may be co-administered including, but not limited to, β-lactam antibiotics, penicillins (such as natural penicillins, aminopenicillins, penicillinase-resistant penicillins, carboxy penicillins, ureido penicillins), cephalosporins (first generation, second generation, and third generation cephalosporins), and other β-lactams (such as imipenem, monobactams), β-lactamase inhibitors, vancomycin, aminoglycosides and spectinomycin, tetracyclines, chloramphenicol, erythromycin, lincomycin, clindamycin, rifampin, metronidazole, polymyxins, doxycycline, quinolones (e.g., ciprofloxacin), sulfonamides, trimethoprim, and quinolines.

A wide variety of antimicrobial agents are currently available for use in treating bacterial, fungal and viral infections.

For a comprehensive treatise on the general classes of such drugs and their mechanisms of action, the skilled artisan is referred to Goodman & Gilman's "The Pharmacological Basis of Therapeutics" Eds. Hardman et al., 9th Edition, Pub. McGraw Hill, chapters 43 through 50, 1996, (herein incorporated by reference in its entirety). Generally, these agents include agents that inhibit cell wall synthesis (e.g., penicillins, cephalosporins, cycloserine, vancomycin, bacitracin); and the imidazole antifungal agents (e.g., miconazole, ketoconazole and clotrimazole); agents that act directly to disrupt the cell membrane of the microorganism (e.g., detergents such as polmyxin and colistimethate and the antifungals nystatin and amphotericin B); agents that affect the ribosomal subunits to inhibit protein synthesis (e.g., chloramphenicol, the tetracyclines, erthromycin and clindamycin); agents that alter protein synthesis and lead to cell death (e.g., aminoglycosides); agents that affect nucleic acid metabolism (e.g., the rifamycins and the quinolones); the antimetabolites (e.g., trimethoprim and sulfonamides); and the nucleic acid analogues such as zidovudine, gangcyclovir, vidarabine, and acyclovir which act to inhibit viral enzymes essential for DNA synthesis. Various combinations of antimicrobials may be employed.

The present invention also includes methods involving co-administration of a composition comprising ISL and/or protein or peptide comprising an ISL with one or more additional active and/or immunostimulatory agents (e.g., a composition comprising ISL and/or protein or peptide comprising an ISL, an antibiotic, anti-oxidant, etc.). Indeed, it is a further aspect of this invention to provide methods for enhancing conventional immunostimulatory methods (e.g., immunization methods) and/or pharmaceutical compositions by co-administering a composition of the present invention. In co-administration procedures, the agents may be administered concurrently or sequentially. In one embodiment, the compositions described herein are administered prior to the other active agent(s). The pharmaceutical formulations and modes of administration may be any of those described herein. In addition, the two or more co-administered agents may each be administered using different modes (e.g., routes) or different formulations. The additional agents to be co-administered (e.g., antibiotics, adjuvants, etc.) can be any of the well-known agents in the art, including, but not limited to, those that are currently in clinical use.

Other delivery systems can include time-release, delayed release or sustained release delivery systems. Such systems can avoid repeated administrations of the compositions, increasing convenience to the subject and a physician. Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109, hereby incorporated by reference. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, each of which is hereby incorporated by reference and (b) diffusional systems in which an active component permeates at a controlled rate from a polymer such as described in U.S. Pat. Nos. 3,854,480, 5,133,974 and 5,407,686, each of which is hereby incorporated by reference. In addition, pump-based hardware delivery systems can be used, some of which are adapted for implantation.

In preferred embodiments, a composition comprising ISL and/or protein or peptide comprising an ISL of the present invention comprises a suitable amount of ISL and/or protein or peptide comprising an ISL to induce an immune response in a subject when administered to the subject. In preferred embodiments, the immune response is sufficient to provide the subject protection (e.g., immune protection) against a subsequent exposure to an immunogen (e.g., a pathogen) or the microorganism (e.g., bacteria or virus) from which the protein or peptide comprising an ISL was derived. The present invention is not limited by the amount of ISL and/or protein or peptide comprising an ISL used. In some preferred embodiments, the amount of ISL and/or protein or peptide comprising an ISL in a composition comprising a ISL and/or protein or peptide comprising an ISL (e.g., for use as an immunization dose) is selected as that amount which induces an immunoprotective response without significant, adverse side effects. The amount will vary depending upon which specific ISL and/or protein or peptide comprising an ISL or combination thereof is/are employed, and can vary from subject to subject, depending on a number of factors including, but not limited to, the species, age and general condition (e.g., health) of the subject, and the mode of administration. Procedures for determining the appropriate amount of ISL and/or protein or peptide comprising an ISL administered to a subject to elicit an immune response (e.g., a protective immune response (e.g., protective immunity)) in a subject are well known to those skilled in the art.

In some embodiments, it is expected that each dose (e.g., of a composition comprising ISL and/or protein or peptide comprising an ISL (e.g., administered to a subject to induce an immune response (e.g., a protective immune response (e.g., protective immunity))) comprises 0.05-5000 µg of each ISL and/or protein or peptide comprising an ISL (e.g., recombinant and/or purified peptide or protein), in some embodiments, each dose will comprise 1-500 µg, in some embodiments, each dose will comprise 350-750 µg, in some embodiments, each dose will comprise 50-200 µg, in some embodiments, each dose will comprise 25-75 µg of ISL and/or protein or peptide comprising an ISL (e.g., recombinant and/or purified peptide or protein). In some embodiments, each dose comprises an amount of the ISL and/or protein or peptide comprising an ISL sufficient to generate an immune response. An effective amount of the immunogen in a dose need not be quantified, as long as the amount of ISL and/or protein or peptide comprising an ISL generates an immune response in a subject when administered to the subject. An optimal amount for a particular administration (e.g., to induce an immune response (e.g., a protective immune response (e.g., protective immunity))) can be ascertained by one of skill in the art using standard studies involving observation of antibody titers and other responses in subjects.

In some embodiments, it is expected that each dose (e.g., of a composition comprising a ISL and/or protein or peptide comprising an ISL (e.g., administered to a subject to induce and immune response)) is from 0.001 to 15% or more (e.g., 0.001-10%, 0.5-5%, 1-3%, 2%, 6%, 10%, 15% or more) by weight ISL and/or protein or peptide comprising an ISL. In some embodiments, an initial or prime administration dose contains more ISL and/or protein or peptide comprising an ISL than a subsequent boost dose In some embodiments, a composition comprising ISL and/or protein or peptide comprising an ISL of the present invention is formulated in a concentrated dose that can be diluted prior to administration to a subject. For example, dilutions of a concentrated composition may be administered to a subject such that the subject receives any one or more of the specific dosages provided herein. In some embodiments, dilution of a concentrated composition may be made such that a subject is administered (e.g., in a single dose) a composition comprising 0.5-50% of the ISL and/or protein or peptide comprising an ISL present in the concentrated composition. In some preferred embodiments, a subject is administered in a single dose a composition comprising 1% of the ISL and/or protein or peptide comprising an ISL present in the concentrated composition. Concentrated compositions are contemplated to be useful in a setting in which large numbers of subjects may be administered a composition of the present invention (e.g., an immunization clinic, hospital, school, etc.). In some embodiments, a composition comprising ISL and/or protein or peptide comprising an ISL of the present invention (e.g., a concentrated composition) is stable at room temperature for more than 1 week, in some embodiments for more than 2 weeks, in some embodiments for more than 3 weeks, in some embodiments for more than 4 weeks, in some embodiments for more than 5 weeks, and in some embodiments for more than 6 weeks.

In some embodiments, following an initial administration of a composition of the present invention (e.g., an initial vaccination), a subject may receive one or more boost administrations (e.g., around 2 weeks, around 3 weeks, around 4 weeks, around 5 weeks, around 6 weeks, around 7 weeks, around 8 weeks, around 10 weeks, around 3 months, around 4 months, around 6 months, around 9 months, around 1 year, around 2 years, around 3 years, around 5 years, around 10 years) subsequent to a first, second, third, fourth, fifth, sixth, seventh, eights, ninth, tenth, and/or more than tenth administration. Although an understanding of the mechanism is not necessary to practice the present invention and the present invention is not limited to any particular mechanism of action, in some embodiments, reintroduction of ISL and/or protein or peptide comprising an ISL in a boost dose enables vigorous systemic immunity in a subject. The boost can be with the same formulation given for the primary immune response, or can be with a different formulation that contains a different ISL and/or protein or peptide comprising an ISL. The dosage regimen will also, at least in part, be determined by the need of the subject and be dependent on the judgment of a practitioner.

Dosage units may be proportionately increased or decreased based on several factors including, but not limited to, the weight, age, and health status of the subject. In addition, dosage units may be increased or decreased for subsequent administrations (e.g., boost administrations).

A composition comprising ISL and/or protein or peptide comprising an ISL of the present invention finds use where the nature of the infectious and/or disease causing agent (e.g., for which protective immunity is sought to be elicited) is known, as well as where the nature of the infectious and/or disease causing agent is unknown (e.g., in emerging disease (e.g., of pandemic proportion (e.g., influenza or other outbreaks of disease))).

It is contemplated that the compositions and methods of the present invention will find use in various settings, including research settings. For example, compositions and methods of the present invention also find use in studies of the immune system (e.g., characterization of adaptive immune responses (e.g., protective immune responses (e.g., mucosal or systemic immunity))). Uses of the compositions and methods provided by the present invention encompass human and non-human subjects and samples from those subjects, and also encompass research applications using these subjects. Compositions and methods of the present invention are also useful in studying and optimizing ISL and/or protein or peptide comprising an ISL, and other components and for screening for new components. Thus, it is not intended that the present invention be limited to any particular subject and/or application setting.

The compositions of the present invention are useful for preventing and/or treating a wide variety of diseases and infections caused by viruses, bacteria, parasites, and fungi, as well as for eliciting an immune response against a variety of antigens. Not only can the compositions be used prophylactically or therapeutically, as described above, the compositions can also be used in order to prepare antibodies, both polyclonal and monoclonal (e.g., for diagnostic purposes), as well as for immunopurification of an antigen of interest. If polyclonal antibodies are desired, a selected mammal, (e.g., mouse, rabbit, goat, horse, etc.) can be immunized with the compositions of the present invention. The animal is usually boosted 2-6 weeks later with one or more—administrations of the antigen. Polyclonal antisera can then be obtained from the immunized animal and used according to known procedures (See, e.g., Jurgens et al., J. Chrom. 1985, 348:363-370).

In some embodiments, the present invention provides a kit comprising a composition comprising ISL and/or protein or peptide comprising an ISL. In some embodiments, the kit further provides a device for administering the composition. The present invention is not limited by the type of device included in the kit. In some embodiments, all kit components are present within a single container (e.g., vial or tube). In some embodiments, each kit component is located in a single container (e.g., vial or tube). In some embodiments, one or more kit component are located in a single container (e.g., vial or tube) with other components of the same kit being located in a separate container (e.g., vial or tube). In some embodiments, a kit comprises a buffer. In some embodiments, the kit further comprises instructions for use.

EXAMPLES

The following examples are provided in order to demonstrate and further illustrate certain preferred embodiments and aspects of the present invention and are not to be construed as limiting the scope thereof.

Example 1

ISL Inhibits Treg Cells and Enhances Th17 Cells

Pro- and Anti-Oxidative Signaling Pathways

Studies have been conducted involving anti- and pro-oxidative signal transduction pathways (Wu et al. Mutat. Res. 546: 93-102, 2004; Ling et al. Muat. Res. 554: 33-43, 2004; US Patent Application No. 20050215529, filed: Sep. 29, 2005; Ling et al. Arthritis Rheum, 54, 3423-3432, 2006; Ling et al. Arthritis Res. Therapy. 9, R5, 2007; Holoshitz & Ling. Ann New York Acad Sci, 1110:73-83, 2007; Ling & Holoshitz. J. Immunol. 179:6359-6367, 2007; herein incorporated by reference in their entireties). Isopentenyl diphosphate (IPP), a product of several pathogens (Puan et al. Int Immunol. 2007 May; 19(5):657-73; herein incorporated by reference in its entirety), was found to be a very potent activator of antioxidative signaling pathway with an IC50 of $1.7 \times 10^{-11}$ M. Anti-oxidative signaling could be blocked by nitric oxide (NO).

Activation of IDO by IPP

Experiments were conducted during development of embodiments of the present invention to determine the effect of IPP on the activity of IDO, a key immune regulatory enzyme. IPP had a very strong synergistic effect with IFN-γ on IDO activation (ISLE FIG. 1). For example, at 10 μM, IPP more than doubled IDO activation in cells treated with 500 U/ml IFN-γ and more than tripled IDO activation in cells treated with 100 U/ml IFN-γ.

Figure 2:
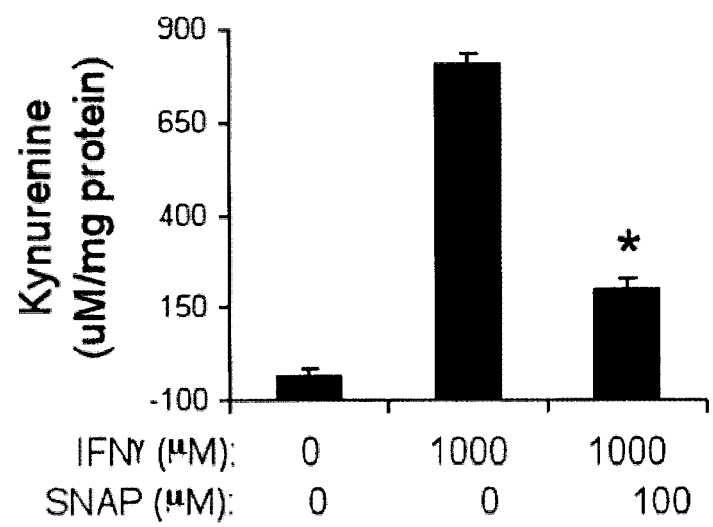
FIG. 2 shows a plot demonstrating NO inhibits IFN-γ-induced indoleamine 2,3-dioxygenase (IDO) activation. Human fibroblasts were preincubated overnight with or without 100 μM of the nitric oxide (NO) donor, S-nitroso-N-acetyl-1,1-penicillamine (SNAP), followed by stimulation with or without 1000 U/ml rhIFN-γ, and IDO activity was measured by quantifying kynurenine production.

In contrast to the anti-oxidative effect of IPP, NO has a pro-oxidative effect. NO has also been shown to inhibit IDO activation (Alberati-Giani et al. J. Immunol. 159, 419-426, 1997; Hucke et al. Infect Immun. 72, 2723-2730, 2004; herein incorporated by reference in their entireties). Consistent with published reports in other cell systems, the NO donor S-nitroso-Nacetylpenicillamine (SNAP) had an inhibitory effect on IFN-γ-induced activation of IDO in fibroblasts (ISLE FIG. 2). Thus, IPP is not only a highly potent antioxidant, it also operate synergistically with IFNγ to increase the activity of IDO, a key enzyme in immune tolerance.

Activation of NO Signaling in Dendric Cells (DC) by ISL.

Figure 3:
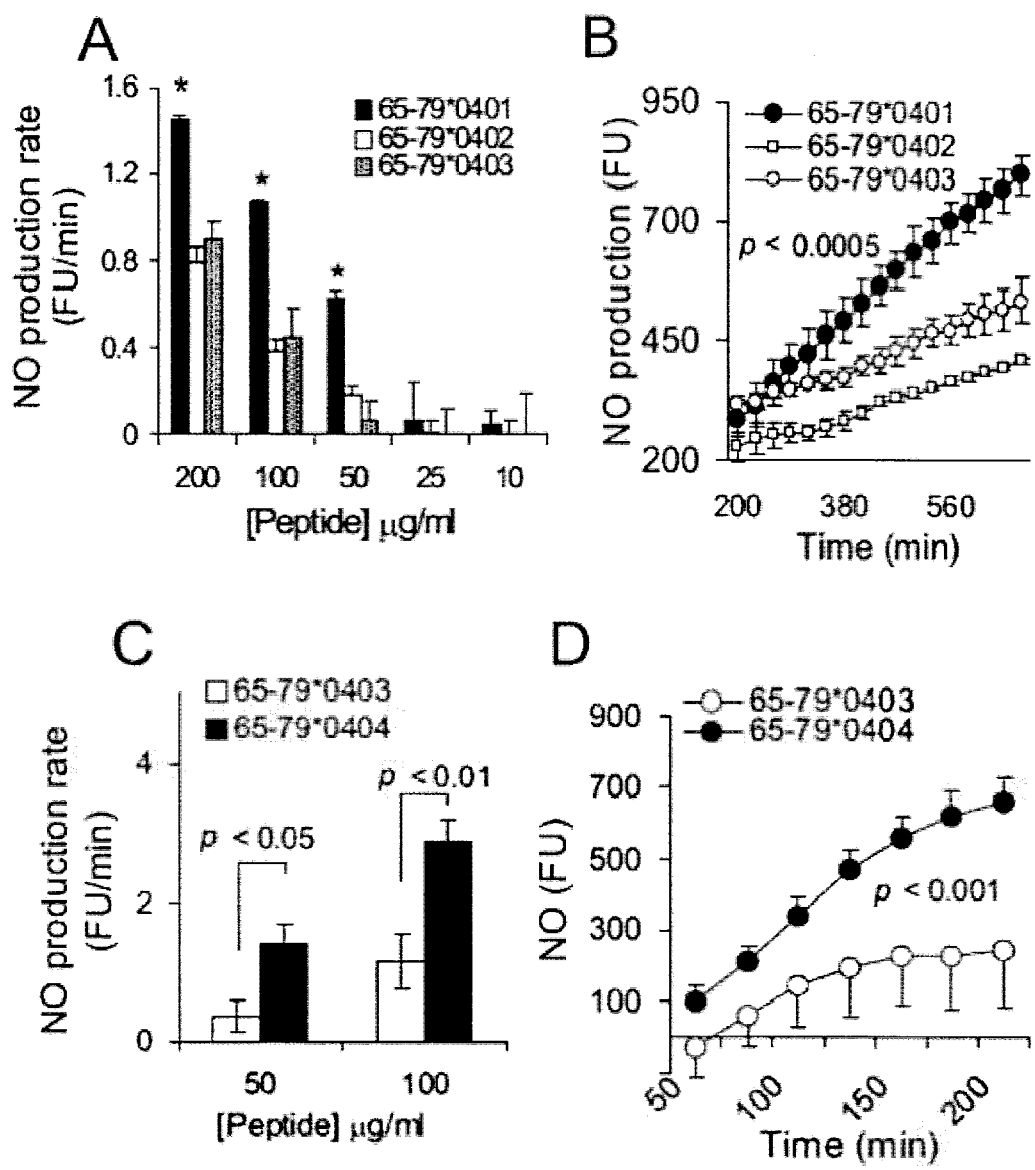
FIG. 3 shows that ISL activates nitric oxide (NO) signaling in dendritic cells (DCs). Bone marrow cells from Balb/c (A and B) or DBA/1 (C and D) mice were differentiated into DCs in culture with GM-CSF (10 μg/ml) and IL-4 (10 μg/ml). CD11c+ DCs were purified using magnetic beads with >95% purity. DCs were then incubated with SE-positive (65-79*0401 or 65-79*0404), or with SE-negative (65-79*0402 or 65-79*0403) 15mer peptides and NO production was measured as described below. The results are expressed as mean±SEM fluorescence units (FU), or FU per minute. *p<0.01 compared to all ligand controls.

There appears to be a functional role for the sequence motif Q/R-K/R-R-A-A in the HLA-DRβ chain. This motif is shared by over 90% of all patients with rheumatoid arthritis. Q/R-K/R-R-A-A was found to act as a ligand capable of triggering NO-mediated pro-oxidative signaling in many cell types via cell surface calreticulin (Ling et al. Arthritis Rheum, 54, 3423-3432, 2006; Ling et al. Arthritis Res. Therapy. 9, R5, 2007; Holoshitz & Ling. Ann New York Acad Sci, 1110:73-83, 2007; Ling & Holoshitz. J. Immunol. 179:6359-6367, 2007; herein incorporated by reference in their entireties). Table 1 summarize different ligands tested in the studies described herein, and their source sequence.

presence of 20 ng/ml GM-CSF. Then, DC were isolated by CD11c magnetic beads with >95% purity. DC cells were incubated over time with 100 μg/ml of ISL-positive or -negative 15mer peptides, and NO production was measured. The ISL-positive peptides 65-79*0401 triggered a much more robust NO production, compared to ISL-negative peptides 65-79*0402 and 65-79*0403 in Balb/c DC (ISLE FIG. 3A-B). Similar trends were seen in DC from C57BL/6 (ISLE FIG. 3C) and CBA/J mice. These data indicate that ISL can activate NO signaling in DC.

Inhibition of IDO by ISL.

IDO plays an important role in T cell regulation, and NO has been previously found to inhibit IDO activity (Alberati-Giani et al. J. Immunol. 159, 419-426, 1997; Hucke et al. Infect Immun. 72, 2723-2730, 2004; herein incorporated by reference in their entireties). Experiments were conducted during development of embodiments of the present invention to examine whether ISL affects IDO activity. First, the effect of ISL-positive and ISL-negative 15mer peptides on IFNγ-induced IDO activity in human fibroblasts was examined. Cells were incubated overnight with 100 μg/ml of ISL-positive or ISL-negative 15mer peptides, cultured for additional 48 h with IFNγ, and IDO activity was measured.

Figure 4:
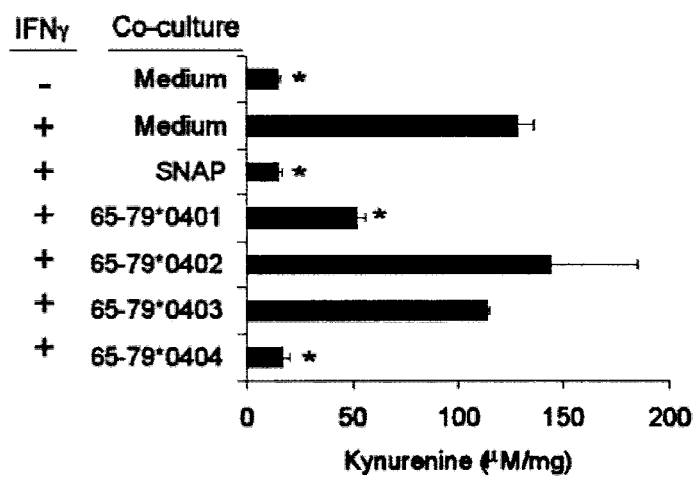
FIG. 4 shows Inhibition of IDO activity by ISL. (A) Human fibroblasts were incubated overnight with either medium, the NO donor, SNAP, or different 15mer peptides (100 μg/ml). Cells were subsequently cultured for 48 h with or without rhIFNγ (1000 U/ml) and cellular IDO activity was determined. (B) Murine L cells expressing either ISL-positive (L-0401, L-0404) or ISL-negative (L-0402, L-0402) DRβ chains on their surface through cDNA transfection were incubated for 48 h with rmIFNγ (1000 U/ml) and cellular IDO activity was determined. (C) CD11+ CD8+ DC were purified from DBA/1 spleens and incubated for 24 h with LPS to induce maturation. Stimulation with IFNγ and IDO activity determination were as above. (D) Immature CD11+ CD8+ DC were purified from DBA/1 spleens and pre-incubated for 1 h with or without HBc particles engineered to express the 65-79 region of DRβ chains, encoded by either ISL-positive (HBc*0401) or ISL-negative (HBc*0402) DRB1 alleles. DCs were subsequently stimulated with IFNγ and IDO activity was determined.
Figure 4:
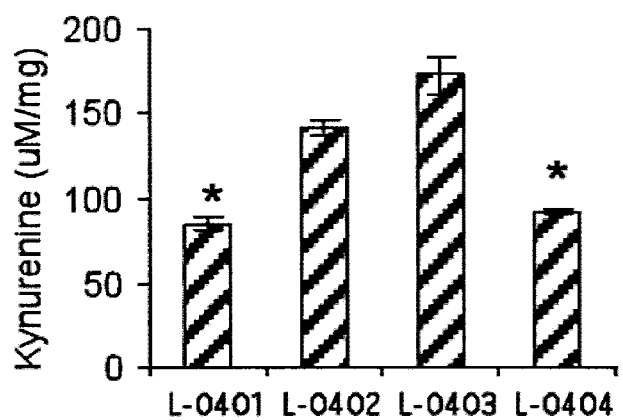
Figure 4:
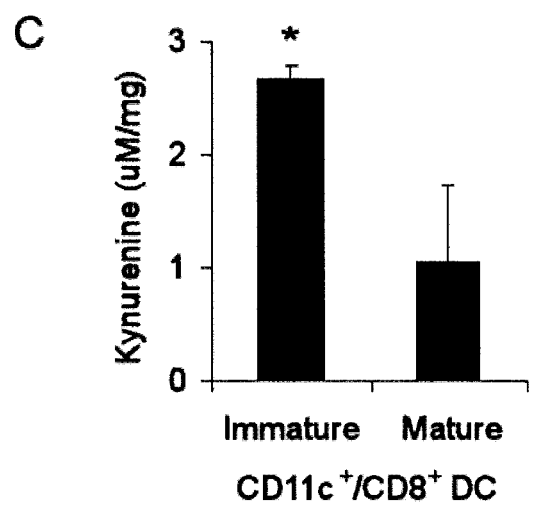
Figure 4:
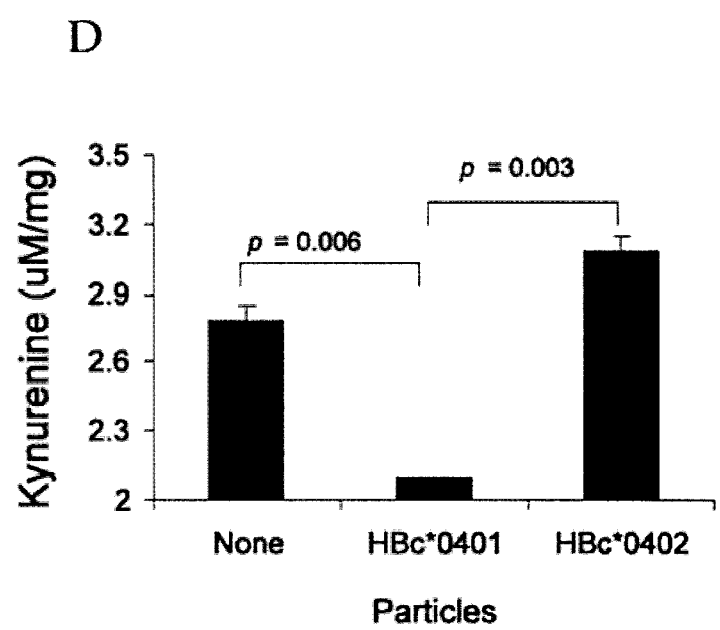

The ISL-positive peptides 65-79*0401 and 65-79*0404 effectively blocked conversion of tryptophan to kynurenine, while ISL-negative peptides 65-79*0402 and 65-79*0403 did not have such effect (ISLE FIG. 4A). Murine L cells expressing ISL-positive DRβ chains on their surface through cDNA transfection (lines L-0401 and L-0404, expressing the ISL-positive DRβ 0401 and DRβ 0404 molecules, respectively), produced significantly less kynurenine in response to IFNγ, when compared to transfectants expressing ISL-negative DRβ chains (lines L-0402 and L-0403, expressing ISL-negative molecules DRβ 0402 and DRβ 0403, respectively) (ISLE FIG. 4B). These results demonstrate ISL effectively inhibits the activity of the tolerogenic enzyme IDO in both human and murine cells.

TABLE 1

Ligands used in this study

| Name: | Origin and composition | Core sequence* | SEQ ID NO | ISL |
|---|---|---|---|---|
| 65-79*0401Region | 65-79 of DRβ chain encoded by DRB1*0401 | QKRAA | SEQ ID NO. 2 | + |
| 65-79*0402Region | 65-79 of DRβ chain encoded by DRB1*0402 | DERAA | SEQ ID NO. 11 | − |
| 65-79*0403Region | 65-79 of DRβ chain encoded by DRB1*0403 | QRRAE | SEQ ID NO. 12 | − |
| 65-79*0404Region | 65-79 of DRβ chain encoded by DRB1*0404 | QRRAA | SEQ ID NO. 3 | + |
| L-0401 | L cell transfectants expressing human DRB1*0401 | QKRAA | SEQ ID NO. 2 | + |
| L-0402 | L cell transfectants expressing human DRB1*0402 | DERAA | SEQ ID NO. 11 | − |
| L-0403 | L cell transfectants expressing human DRB1*0403 | QRRAE | SEQ ID NO. 12 | − |
| L-0404 | L cell transfectants expressing human DRB1*0404 | QRRAA | SEQ ID NO. 3 | + |
| HBc*0401 | Hepatitis B core particles expressing region 65-79 of DRβ chain encoded by DRB1*0401 | QKRAA | SEQ ID NO. 2 | + |
| HBc*0402 | Hepatitis B core parades expressing region 65-79 of DRβ chain encoded by DRB1*0402 | DERAA | SEQ ID NO. 11 | − |

*Sequence of the polymorphic residues 70-74 of the DRβ chain

DCs play a key role in immune regulation. Studies were conducted during development of embodiments of the present invention to examine whether the ISL can activate innate signaling in murine DC. Bone marrow cells were isolated from three mouse strains and cultured for 7 days in the IFNγ-induced IDO activity was found in DCs expressing the CD8α surface marker (CD8+ DC), but not in CD8α-negative DC (CD8− DC). Experiments were conducted to examine the effect of maturation on IDO activity. CD11c+ CD8+ DC were incubated for 24 h with or without LPS and IFNγ-induced IDO activity was determined. Activation of IDO in immature DC was significantly higher than in mature cells (ISLE FIG. 4C). To determine the effect of ISL on IDO activity in DC, immature CD11c+ CD8+ DC were purified from DBA/1 spleens and pre-exposed to ISL in the form of HBc particles engineered to express the 65-79 region of DRβ chains, encoded by the ISL-positive allele DRB1*0401 (particle HBc*0401). ISL-negative particles (HBc*0402), expressing the DRβ 65-79 region encoded by the ISL-negative DRB1*0402 allele were used as control (these 2 particles differ by only 2 amino acid residues in the 70-74 region of the insert). DCs were subsequently stimulated with IFNγ and IDO activity was determined. ISL-positive, but not ISL-negative particles inhibited IDO activity in DC (ISLE FIG. 4D).

ISL-Induced IL-6 Production.

Figure 5:
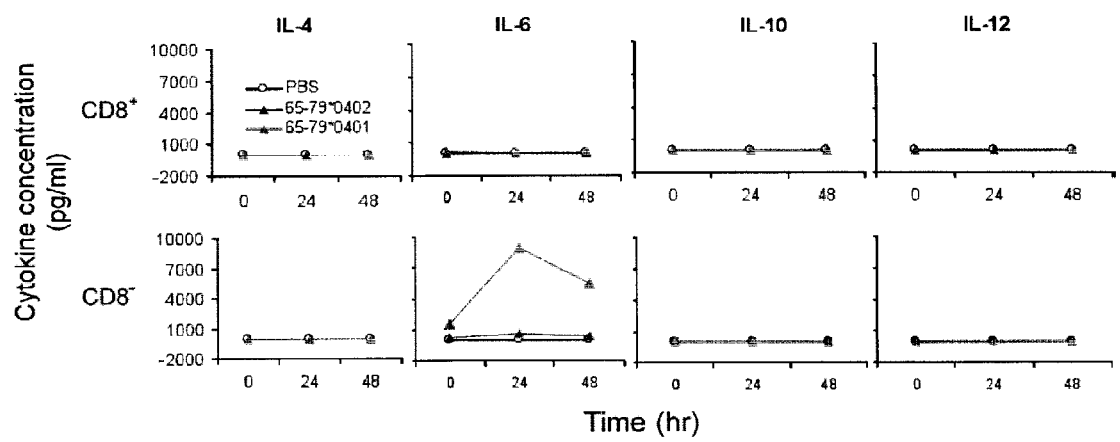
FIG. 5 shows ISL-stimulated cytokine production by DC. Splenic CD8+ and CD8− DC were isolated from DBA/1 mice as above and cultured in 96-well plates over time in the presence or absence of ISL-positive (65-79*0401) or ISL-negative (65-79*0402) peptides (50 μg/ml). At various time points thereafter, supernatants were collected and assayed for cytokine content, using the Luminex platform.

In addition to IDO-mediated T cell regulation, DC can also regulate immune responses by production of various cytokines that can activate or expand particular subsets of T cells, thereby polarizing the immune response. Experiments were conducted during development of embodiments of the present invention to determine whether ISL-mediated signaling in DC could induce particular cytokines. Supernatants of ISL-stimulated DC were examined using the Luminex platform. While CD8+ DC showed no production of any cytokines, in the CD8− subset, the ISL-positive peptide 65-79*0401 triggered a robust production of IL-6 (ISLE FIG. 5). The ISL-negative peptide 65-79*0402 did not trigger any increased production, similar to cultures incubated with PBS. Other cytokines (IL-4, IL-10 and IL-12) did not show any increased production, indicating the specificity of ISL effect.

Example 2

Compositions and Methods

Experiments were performed during development of embodiments of the present invention to elucidate the role of the ISL in the immune system. The effect of ISL on T cell polarization in mice was examined. In CD11c+ CD8+ DCs, the ISL inhibited the enzymatic activity of IDO, a key enzyme in immune tolerance and T cell regulation, while in CD11c+ CD8− DCs the ligand activated robust production of IL-6. When ISL-activated DCs were co-cultured with CD4+ T cells, the differentiation of Foxp3+ T regulatory (Treg) cells was suppressed, while Th17 cells were expanded. The polarizing effects were observed with ISL-positive synthetic peptides, but even more so, when the ISL was in its natural tri-dimensional conformation as part of HLA-DR tetrameric proteins. In vivo administration of the ISL resulted in higher abundance of Th17 cells in the draining lymph nodes and increased IL-17 production by splenocytes, demonstrating that the ISL acts as a potent immune-stimulatory ligand that can polarize T cell differentiation toward Th17 cells, a T cell subset that has been recently implicated in the pathogenesis of autoimmune diseases, including RA.

Mice and Reagents

All mice were from Jackson Laboratory. Experiments were carried out in 5-10 week-old male DBA/1, Balb/c, C57BL/6, or a DBA/1 mouse line carrying transgenic (Tg) collagen type II (CII)-specific TCR (D1Lac.Cg-Tg(TCRa,TCRb)24Efro/J); the latter mouse line is designated herein as "CII-TCR Tg mice." The animals were housed in the University of Michigan Unit for Laboratory Animal Medicine facility. All experiments were performed in accordance with protocols approved by University of Michigan Committee on Use and Care of Animals.

Monoclonal antibodies against mouse CD3 (clone 2C11), IL-4 (clone 11B11), IFNγ (clone R46A2), and IL-2 (clone S4B6) were purified from the supernatants of hybridomas obtained from the University of Michigan Hybridoma Core Facility. Purified anti-mouse CD28 (clone 37.51) and murine rIL-23 were purchased from e-Bioscience (San Diego, Calif.). Human rTGFβ and rIFNγ, as well as murine rIL-4, rIFNγ, rGM-CSF and rIL-6 were purchased from Peprotech (Rocky Hill, N.J.).

Peptides were synthesized and HPLC-purified to >90% by the University of Michigan Protein Structure Facility as previously described (9, 12). ISL-expressing 15mer peptides, designated as 65-79*0401 (aa sequence 65-KDLLEQKRAAVDTYC-79 SEQ ID NO.: 7), or 65-79*0404 (aa sequence 65-KDLLEQRRAAVDTYC-79 SEQ ID NO.: 8), corresponded to the third allelic hypervariable region (HVR3) of the DRβ chain encoded by of ISL-positive HLA-DRB1*0401 or HLA-DRB1*0404 alleles, respectively. Control 15mer peptides 65-79*0402 (65-KDILEDERAAVDTYC-79 SEQ ID NO.: 9) and 65-79*0403 (65-KDLLEQRRAEVDTYC-79 SEQ ID NO.: 10) corresponded to the HVR3 of the DRβ chain encoded by of ISL-negative HLA-DRB1*0402 or HLA-DRB1*0403 alleles, respectively. The CII259-273 peptide, which corresponds to residues 259-273 of chicken CII.

Chimeric hepatitis B core (HBc) particles engineered to express the HVR3 of the HLA-DRβ chain were prepared at the Latvian Biomedical Research and Study Center, (Riga, Latvia) (Holoshitz & Ling. 2007 Ann N Y Acad Sci 1110:73-83; herein incorporated by reference in its entirety). HBc particles expressing a ISL-positive HVR3, encoded by HLA-DRB1*0401 (designated here as HBc*0401) or a ISL-negative HVR3, encoded by HLA-DRB1*0402 (designated here as HBc*0402) were used in experiments conducted herein. ISL-positive HLA-DR tetramers DRB1*0401/DRA1*0101 (designated here as T-DRB1*0401), ISL-negative DRB1*1501/DRA1*0101 (T-DRB1*1501), and ISL-negative DRB1*0301/DRA1*0101 (T-DRB1*0301), all containing identical class II-associated invariant chain peptide (CLIP) in the peptide-binding groove, were generated by the National Institutes of Health Tetramer Core Facility as previously described (Day et al. 2003. J Clin Invest 112:831-842; herein incorporated by reference in its entirety. Unless stated otherwise, all chemicals were from Sigma-Aldrich (St. Louis, Mo.).

Isolation and Culture of Cells

Murine L cell transfectants expressing human HLA-DRα/β heterodimers (Olson et al. Hum Immunol 41:193-200; herein incorporated by reference in its entirety) and human fibroblast line M1 (Holoshitz & Ling. 2007 Ann N Y Acad Sci 1110:73-83; herein incorporated by reference in its entirety) were maintained as we previously described. For generation of CD11c+ DCs, mouse bone barrow cells were plated in culture flasks (2×106 cells/ml per T150, Costar, Corning, N.Y.) in RPMI 1640 medium containing 2 mM L-glutamine, 10% FBS, 1% Penicillin-Streptomycin, 10 mM HEPES buffer solution, 10 mM Sodium Pyruvate, 50 mM 2-mercaptoethanol, GM-CSF (10 ng/ml) and IL-4 (10 ng/ml). On day 3, half of the medium was removed and fresh medium containing GM-CSF (10 ng/ml) and IL-4 (10 ng/ml) were added. After 5-7 days, DCs were purified using positive selection columns with CD11c microbeads (Miltenyi Biotec Inc, CA, USA) as previously described (Grohmann et al. 1998 Immunity 9:315-323; herein incorporated by reference in its entirety). For preparation of CD11c+ CD8+ and CD11c+ CD8− DCs, freshly isolated splenic DCs were subjected to positive selection with CD11c and CD8α microbeads. Purified DC subsets were then cultured in RPMI 1640 medium containing 2 mM L-glutamine, 10% FBS, 1% Penicillin-Streptomycin, 10 mM HEPES buffer solution, 10 mM Sodium Pyruvate and 50 mM 2-mercaptoethanol. CD4+ T cells were isolated from the spleen, using a negative selection immunomagnetic isolation kit (EasySep®, Stem Cell technology, Vancouver, Canada) according to the manufacturer's instructions. To purify CD4+ CD25− CD62L+ CD44− naïve T cells, CD4+ T cells were incubated with FITC anti-mouse CD4 and a mixture of PE-labeled anti-CD25, APC-labeled anti-CD62L and Pe-Cy7-labeled anti-CD44 antibodies (all from Biolegend, San Diego, Calif.). CD4+ CD25− CD62L+ CD44− naïve T cells were sorted using a FACSDiva™ instrument (Becton Dickinson, Franklin Lakes, N.J.) with a purity >98%.

Measurement of NO Production, IDO Activity and Cytokine Secretion

To determine the rate of NO production, cells were loaded with 20 µM of the fluorescent NO probe 4,5-diaminofluorescein diacetate (DAF-2DA) and the fluorescence level was recorded every 5 minutes over a period of 500 minutes using a Fusion αHT system (PerkinElmer Life Sciences) at an excitation wavelength of 488 nm and emission wavelength of 515 nm. To determine IDO enzymatic activity, the generation of its product, kynurenine was measured (Takikawa et al. 1988. J Biol Chem 263:2041-2048; herein incorporated by reference in its entirety). Cytokine concentrations were measured in cell culture supernatants using a Luminex platform (Millipore Corporation, Danvers, Mass.). In some experiments, cytokines were determined using ELISA (Quantikine®, R&D Systems, Minneapolis, Minn.) following the manufacture's instruction.

Determination of Surface CRT Expression on DCs

Splenic cells from DBA/1 mice were isolated followed by purification of DC subtypes using positive selection columns with CD11c and CD8α microbeads. Purified cells were stained for flow cytometry analysis using PE anti-mouse CD8 (clone 53-6.7, BD Pharmigen, San Jose, Calif.), FITC anti-rabbit CRT (ABR—Affinity Bioreagents, Rockford, Ill.) and isotype controls (Biolegend, San Diego, Calif.).

Treg Differentiation

DBA/1 bone marrow-derived CD11c+ DCs were placed in 24-well plates (BD Biosciences, San Jose, Calif.) at a density of 2.5×105 cells per well and cultured overnight with or without 50 µg/ml of peptidic (65-79*0401 or 65-79*0402), or 2 µg/ml of tetrameric (T-DR1*0401, T-DR1*0301, or T-DR1*1501) ligands at 37° C. On the following day, 5.0× 105 CD4+ T cells or CD4+ CD25− CD62L+ CD44− naïve T cells, isolated as described above, were added to each well in addition to anti-CD3 antibodies (5 µg/ml) and rhTGFβ (2.5 ng/ml).

After 5 days in culture, cells were harvested and stained for flow cytometric analysis using FITC anti-mouse CD4 (clone XMG1.2), PE anti-mouse CD25 (clone PC61) and isotype controls (Biolegend, San Diego, Calif.). Next, cells were permeabilized and fixed using a Cytofix/Cytoperm kit (BD Biosciences, San Jose, Calif.) as recommended by the manufacturer. After permeabilization, cells were stained using an APC-conjugated anti-mouse Foxp3 antibody (clone FLK-16S from e-Bioscience, San Diego, Calif.) and analyzed by FACScalibur flow cytometer using the CELLQuest™ software (Becton Dickinson, Franklin Lakes, N.J.).

Th17 Differentiation

Bone marrow-derived CD11c+ DCs (2.5×105 cells per well) were cultured overnight in 24-well plates with or without ISL ligands or controls as above. Then, 5×105 CD4+ T cells or CD4+ CD25− CD62L+ CD44− naïve T cells were added at the ratio of 2:1 in the presence of Th17-polarizing cytokine/antibodies cocktail containing: anti-IL4 (2 µg/ml), anti-IFNγ (2 µg/ml), anti-IL2 (3 µg/ml), rhTGFβ (5 ng/ml), rmIL-6 (20 ng/ml), rmIL-23 (10 ng/ml), anti-CD3 (5 µg/ml) and anti-CD28 (1 µg/ml) as previously described (32).

After 6 days, cells were stimulated with PMA (5 ng/ml) and ionomycin (500 ng/ml) for the last 6 hrs of culture. Brefeldin A (10 µg/ml) was added to the culture for the last 5 hrs. Cells were then harvested and stained for surface marker using PercP anti-mouse CD4 or isotype control (Biolegend, San Diego, Calif.) followed by fixation and permeabilization using a Cytofix/Cytoperm™ kit. Intracellular staining was performed using PE-conjugated anti-mouse IL-17A mAb (clone TC11-18H 10.1 from Biolegend, San Diego, Calif.). Mean florescence intensity and percentages of stained cells were determined by flow cytometry.

Proliferation Assays

Cells were labeled with 1 µM of CFISL (Molecular Probes™, Invitrogen Corporation, Carlsbad, Calif.), stained with CD4-PercP, CD25-Pe, and Foxp3-APC or IL-17A-APC antibodies (Biolegend, San Diego, Calif.) and proliferation was determined by measuring the percentages of CFISL-labeled cycling CD4+ T, CD4+ CD25+ Foxp3+ Treg or CD4+ IL17A+ Th17 cells, using a FACS analysis.

Determination of the ISL Polarizing Effect In Vivo

Mice were injected subcutaneously in the footpad with 100 µg of chicken collagen type II (CII) (Chondrex, Inc, Redmond, Wash.) emulsified in CFA (4 mg/ml). The inoculums contained 10 µg of either ISL-positive 65-79*0401 or ISL-negative 65-79*0402 ligands in PBS, or an equal volume of PBS alone. Animals were sacrificed 7 days after immunization. For Th17 quantification studies, inguinal and popliteal lymph nodes were collected and single cell suspensions were prepared. Unfractionated lymph node cells were cultured with PMA, Ionomycin and Brefeldin A for 6 hours as above. Cells were stained with FITC anti-mouse CD4 or isotype controls, followed by fixation and permeabilization using a Cytofix-Cytoperm™ kit. After permeabilization, intracellular staining was performed using PE-conjugated anti-mouse IL17A and APC-conjugated anti-mouse IFN-γ and cells were analyzed by flow cytometry as above. To measure IL-17 production, splenocytes from mice immunized as above were stimulated in vitro with 5 µg of CII259-273 peptide. At different time points thereafter, supernatants were collected and assayed for IL-17 by ELISA as above.

Example 3

Induction of Immune Response by ISL

The ISL Inhibits IDO Activity

The ISL activates NO signaling in different cell lineages from several species (Holoshitz & Ling. 2007 Ann N Y Acad Sci 1110:73-83; Ling et al. 2006 Arthritis Rheum 54:3423-3432; Ling et al. 2007 Arthritis Res Ther 9:R5; Ling et al. 2007 J Immunol 179:6359-6367; herein incorporated by reference in their entireties). The ISL activated robust NO production in CD11c+ DCs from several mouse strains in a strictly allele-specific manner. Thus, similar to its effect in many other cell lineages, the ISL activates NO signaling in mouse DCs as well.

Given the known inhibitory effect of NO on IDO activity (Alberati-Giani et al. 1997 J Immunol 159:419-426; herein incorporated by reference in its entirety), experiments were conducted during development of embodiments of the present invention to determine the effect IDO enzymatic activity. In addition to a small subset of DCs (Fallarino et al.

Figure 6:
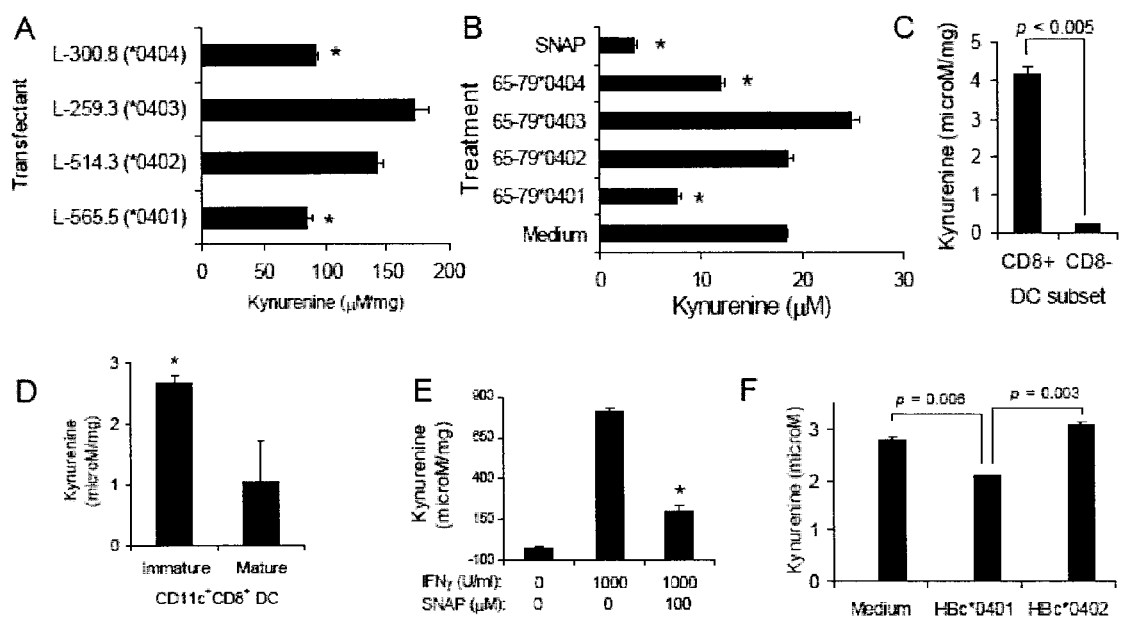
FIG. 6 shows inhibition of IDO activity by the ISL. (A) Murine L cells expressing either ISL-positive (L-565.5, or L-300.8) or ISL-negative (L-514.3, or L-259.3) functional HLA-DR molecules on their surface through cDNA transfection were incubated for 48 hrs with rhIFNγ (1000 U/ml) and cellular IDO activity was determined. (B) M1 fibroblasts were incubated overnight with medium, NO donor SNAP, or 100 μg/ml of ISL ligands (65-79*0401, 65-79*0404), or with ISL-negative controls (65-79*0402, or 65-79*0403). Cells were cultured for 48 hrs with rhIFNγ and cellular IDO activity was determined. (C) The CD11c+ CD8+ and CD11c+ CD8− DCs subsets were purified from DBA/1 spleens and their IDO activity in response to IFNγ was determined. (D) CD11c+ CD8+ DCs were purified from DBA/1 spleens, maturated or not with LPS, and their IDO activity in response to IFNγ was determined. (E) DBA/1 splenic CD11c+ CD8+ DCs were activated with or without IFNγ, in the presence of absence of the NO donor SNAP. IDO activity was determined at 48 h as above. (F) DBA/1 splenic CD11c+ CD8+ DCs were pre-incubated for 1 hr with or without HBc particles engineered to express the 65-79 region of DRβ chains, encoded by either ISL-positive (HBc*0401) or ISL-negative (HBc*0402) HLA-DRB1 alleles. DCs were subsequently stimulated with IFNγ and IDO activity was determined as above.

2002. Int Immunol 14:65-68; herein incorporated by reference in its entirety), IDO is expressed in several other cell lineages, including fibroblasts. Given the much greater abundance of fibroblasts over IDO-producing DCs, the effect of the ISL on IDO activity in murine fibroblast L-cells transfectants expressing functionally and structurally intact HLA-DRα/β heterodimeric molecules on their surface through cDNA transfection was determined. Transfectants expressing ISL-positive HLA-DR molecules on their surface (lines L-565.5 and L-300.8, expressing the ISL-positive DRβ 0401 or DRβ 0404 molecules, respectively) produced significantly less kynurenine in response to IFNγ, compared to transfectants expressing ISL-negative HLA-DR molecules (lines L-514.3 and L-259.3 expressing ISL-negative DRβ 0402 or DRβ 0403 molecules, respectively) (ISLE FIG. 6). An identical pattern was observed when M1 fibroblasts were stimulated with ISL peptidic ligands 65-79*0401 or 65-79*0404. The ISL ligands strongly inhibited IFNγ-induced IDO activity (ISLE FIG. 6B). ISL-negative controls 65-79*0402 and 65-79*0403 did not inhibit IDO activity. Consistent with previous studies (Alberati-Giani et al. 1997 J Immunol 159: 419-426; Thomas et al. 1994. J Biol Chem 269:14457-14464; herein incorporated by reference in their entireties) the NO-donor S-nitroso-N-acetylpenicillamine (SNAP) inhibited IDO activity too. Thus, these results demonstrate that the ISL, whether physiologically expressed on the cell surface (e.g., in the form of HLA-DR), or added as a cell-free ligand, effectively and specifically inhibits the activity of the tolerogenic enzyme IDO in human and murine cells.

IFNγ-induced IDO activity in DBA/1 mice was observed in CD11c+ CD8+ DCs, but not in CD11c+ CD8− DCs (ISLE FIG. 6C), similar to published reports in other strains (Fallarino et al. 2002. Int Immunol 14:65-68; herein incorporated by reference in its entirety). To examine the effect of maturation on IDO activity in DBA/1 mice, CD11c+ CD8+ DCs were incubated for 24 hrs with or without LPS (1 µg/ml) and IFNγ-induced IDO activity was determined. Activation of IDO in immature DCs was significantly more potent than in mature cells (ISLE FIG. 6D). Similar to other mouse strains, IDO activation in DBA/1 mice was inhibited by NO by demonstrating that IFNγ-induced IDO activity in DBA/1 immature CD11c+ CD8+ DCs is potently inhibited by the NO-donor SNAP (ISLE FIG. 6E). To determine the effect of the ISL on IDO activity in DCs, DBA/1 immature CD11c+ CD8+ DCs were pre-incubated with HBc particles engineered to express the HVR3 (residues 65-79) encoded by the ISL-positive allele DRB1*0401 (designated HBc*0401), or the HVR3 encoded by the ISL-negative allele DRB1*0402 (HBc*0402). Cells were then stimulated with IFNγ and IDO activity was determined as above. ISL-positive HBc*0401 but not ISL-negative HBc*0402 particles significantly inhibited IDO activity in DCs (ISLE FIG. 6F). Thus, experiments conducted during development of embodiments of the present invention indicate that the ISL ligand inhibits IDO activity in CD11c+ CD8+ DCs.

Cytokine Production by ISL-Stimulated DCs

In addition to IDO-mediated T cell regulation, DCs can affect immune responses by producing cytokines capable of activating or expanding particular subsets of T cells, thereby polarizing the immune response. For example, in mice, the combination of IL-6 and TGFβ facilitates differentiation of Th17 cells, while IL-23 is involved in the expansion of this subset (Ivanov et al. 2007 Semin Immunol 19:409-417; herein incorporated by reference in its entirety). In order to determine whether ISL-activated signaling in DCs induces cytokine production, supernatants of ISL-stimulated DCs were examined. The ISL ligand 65-79*0401 activated a robust production of IL-6 in CD11c+ CD8− DCs, but not in the CD11c+ CD8+ subset (ISLE FIG. 7). IL-6 levels peaked at a relatively early time point (24 h) and later declined. This pattern is likely a result of short half life of the peptidic ligand due to rapid degradation in tissue culture conditions. The ISL-negative control 65-79*0402 did not trigger any cytokine production. Other cytokines (IL-4, IL-10, IL-12, IL-1β, TGFβ) did not show any increased production, attesting to the specificity of the ISL effect (ISLE FIG. 7). Thus, while in CD8+ DCs the ISL inhibited IDO activity (ISLE FIG. 6)) its IL-6 production effect was restricted to the CD8− DCs subset (ISLE FIG. 7).

Figure 7:
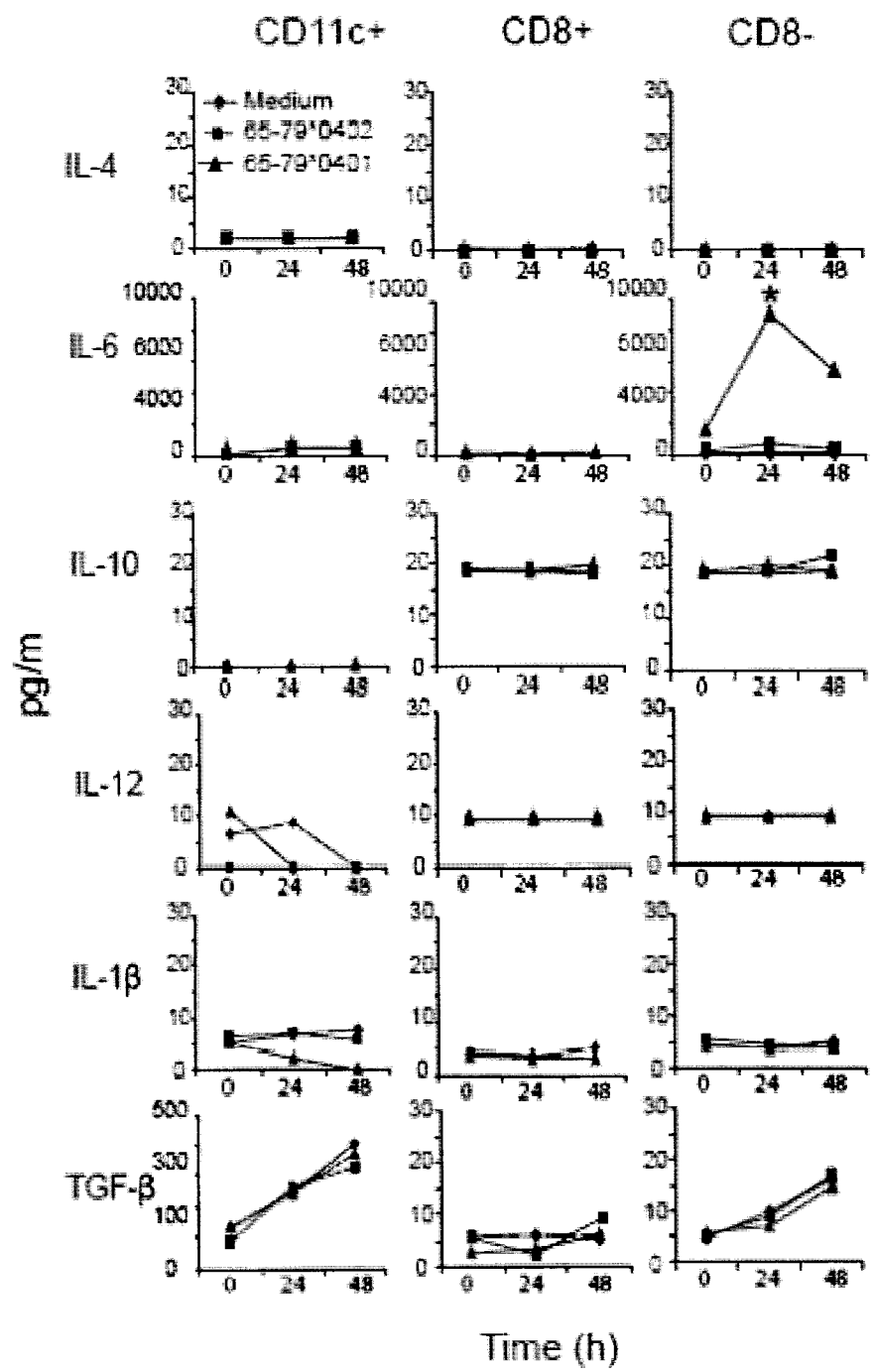
FIG. 7 shows The ISL activates IL-6 production in CD8− DCs. DBA/1 splenic unfractionated CD11c+ DCs (CD11c+), or their purified CD11c+ CD8+ DCs (CD8+) or CD11c+ CD8− DCs (CD8−) subsets were cultured with the ISL 65-79*0401 or ISL-negative control 65-79*0402 or medium. Supernatants were collected at different time points and assayed for cytokine content using a Luminex platform.

ISL-activated IL-6 production was observed CD11c+ CD8− DCs only when they were separated from the CD11c+ CD8+ subset, but not when unfractionated CD11c+ DCs were assayed (ISLE FIG. 7). Although CD 11c+ CD8+ DCs are a small subset (~5-15% of splenic CD11c+ cells), once activated by the ISL, they could exert potent inhibitory effect on the activation of CD11c+ CD8− DCs, consistent with previously reported DCs suppressive effects (Ardavin et al. 2004 Immunity 20:17-23; herein incorporated by reference in its entirety); although the present invention is not limited to any particular mechanism of action and an understanding of the mechanism of action is not necessary to practice the present invention. Recent studies have indeed shown that IDO produced by a small subset of DCs can dominantly suppress production of IL-6 in other DCs (Sharma, et al. 2009 Blood 113:6102-6111; Baban et al. 2009 J Immunol 183:2475-2483; herein incorporated by reference in their entireties).

Figure 8:
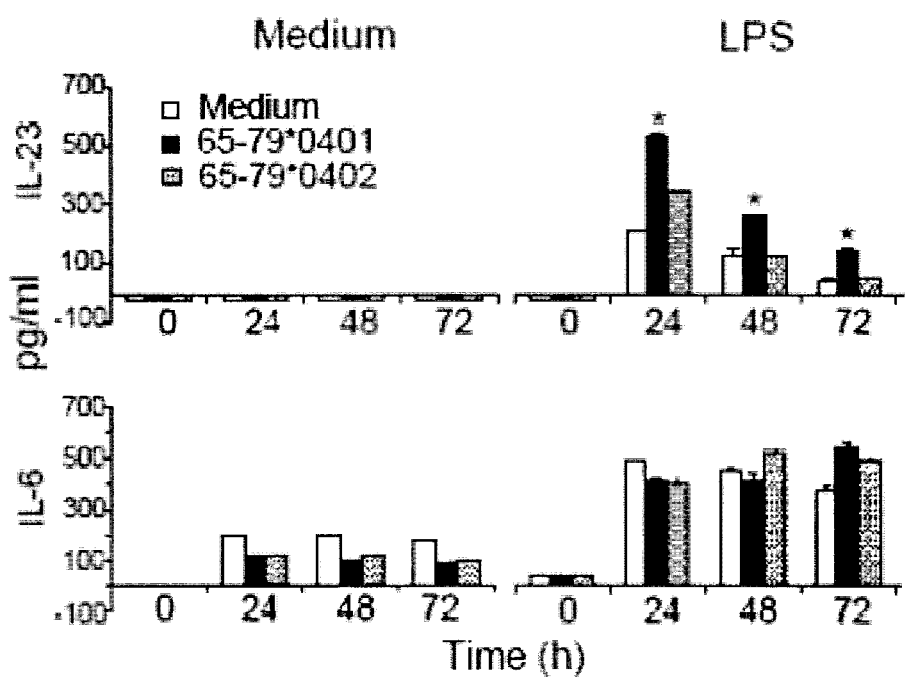
FIG. 8 shows the ISL augments IL-23 production in LPS-stimulated CD11c+ DCs. DBA/1 bone marrow-derived CD11c+ DCs were cultured with or without 100 ng/ml LPS in the presence or absence of ISL-positive or ISL-negative 15mer peptides (50 μg/ml). Supernatants were collected at different time points and assayed for IL-23 and IL-6 content by ELISA.

IL-23 levels in DCs did not increase following stimulation with the ISL ligand (ISLE FIG. 8). However, in the presence of LPS (100 ng/ml), the ISL had a prolonged synergistic effect in CD11c+ DCs. The ISL had no effect when applied alone, but in the presence of LPS it had a synergistic effect, which lasted for up to 72 hours after stimulation, long after LPS effect had subsided (ISLE FIG. 8). The effect was specific for IL-23, since no synergism was found in the production of another LPS-inducible cytokine, IL-6 (ISLE FIG. 8, bottom).

Inhibition of Treg Differentiation by the ISL

Figure 9:
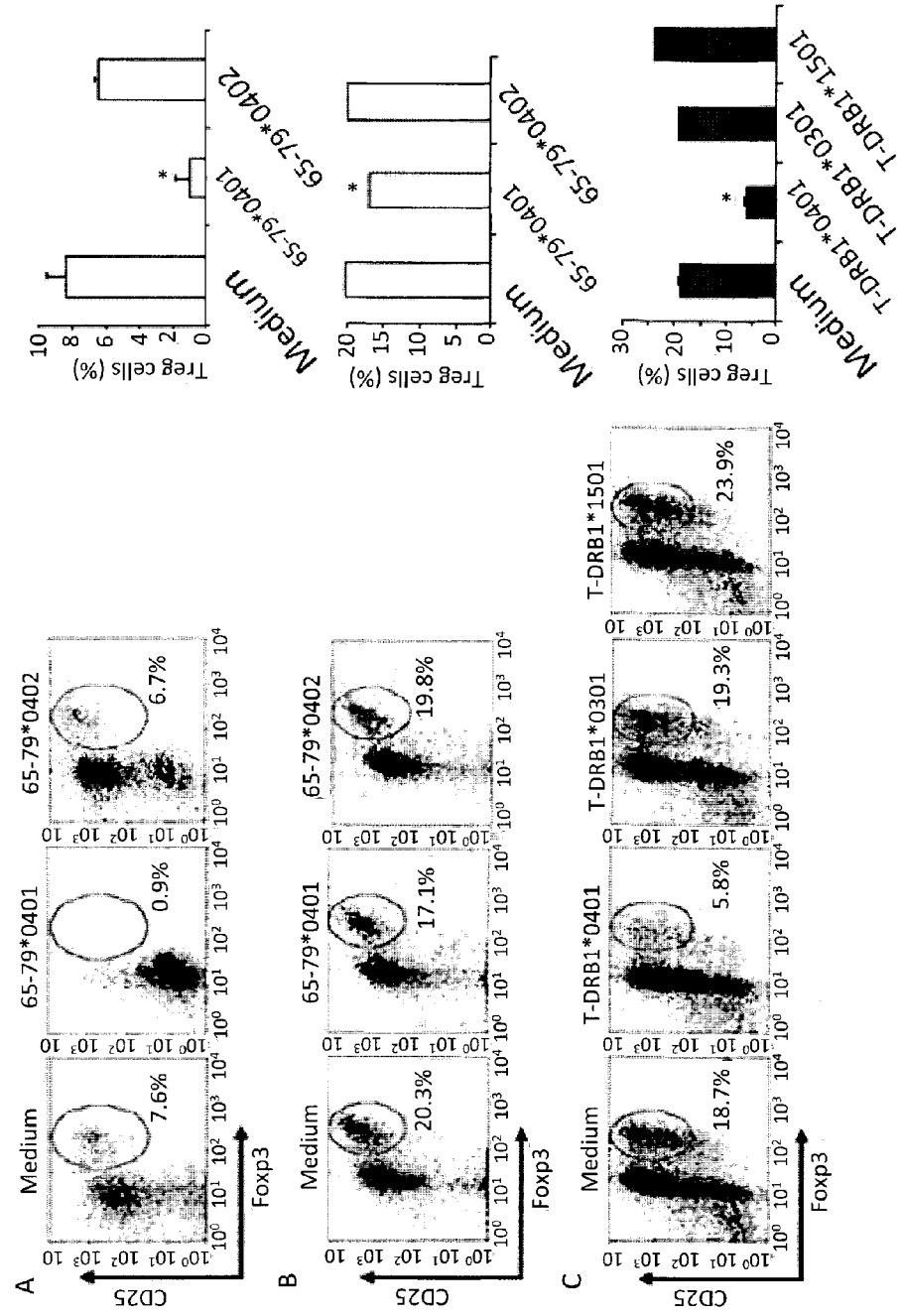
FIG. 9 shows ISL inhibits Treg generation. (A) DBA/1 bone marrow-derived CD11c+ DCs were cultured overnight with 50 μg/ml ISL ligand 65-79*0401 or ISL-negative control 65-79*0402, or medium. Syngeneic splenic CD4+ T cells were then added to the culture, and incubated with anti-CD3 and TGF-β for 5 days. On the left, flow cytometry dot plots showing percentages of CD25+ Foxp3+ cells obtained from gated CD4+ T cells in each treatment. Each plot is representative of three experiments. On the right, bar graphs present results as mean percentage±SD of replicate samples. (B) Cultures were performed as in (A), with the exception that CD4+ CD25− CD62L+ CD44− naïve T cells, instead of CD4+ T cells were added to the CD11c+ DCs. (C) DBA/1 bone marrow-derived CD11c+ DCs were incubated overnight with 2 μg/ml tetramers (ISL-positive T-DRB1*0401, versus ISL-negative T-DRB1*0301, or T-DRB1*1501). Syngeneic CD4+ CD25− CD62L+ CD44− naïve T cells, anti-CD3 and TGF-β were then added to the culture and incubated for 5 days and analyzed as above.

IDO inhibition and/or increased IL-6 levels inhibit Treg cells (Sharma et al. 2007 J Clin Invest 117:2570-2582; Korn et al. 2007 Nature 448:484-487; herein incorporated by reference in their entireties). The ISL inhibited IDO activity in CD11c+ CD8+ DCs and increased IL-6 production in CD11c+ CD8− DCs. Experiments were conducted during development of embodiments of the present invention to determine whether the ISL interferes with Treg differentiation or expansion. Accordingly, DBA/1 CD11c+ DCs were first incubated overnight with the ISL ligand 65-79*0401, or ISL-negative control 65-79*0402, or with medium. DCs were then co-cultured with purified syngeneic CD4+ T cells (ISLE FIG. 9A) or CD4+ CD25− CD62L+ CD44− naïve T cells (ISLE FIG. 9B) in the presence of TGF-β (2.5 ng/ml) and anti-CD3 antibodies (5.0 µg/ml). After 5 days, CD4+ CD25+ Foxp3+ Treg abundance was determined by flow cytometry. The ISL ligand 65-79*0401 significantly inhibited Treg expansion and differentiation, respectively (ISLE FIG. 9). The inhibitory effect of 65-79*040 on Treg differentiation was statistically significant, yet modest. Peptidic ISL ligands have been observed to exert weaker signaling effects due to their flexible conformation in solution (Holoshitz & Ling. 2007 Ann NY Acad Sci 1110:73-83; Ling et al. 2006. Arthritis Rheum 54:3423-3432; Ling et al. 2007 J Immunol 179: 6359-6367; herein incorporated by reference in their entireties). Treg differentiation experiments were performed using ISL-positive HLA-DR tetramer (designated T-DRB1*0401), or control, ISL-negative HLA-DR tetramers (T-DRB1*1501 or T-DRB1*0301) instead of soluble peptides. The HLA-DR molecule in tetramers is folded in its natural tri-dimensional conformation and therefore better preserves the physiologic function of the protein. The ISL-positive tetramer T-DRB1*0401 indeed had a specific and much more potent inhibitory effect on Treg differentiation (ISLE FIG. 9C).

ISL-Activated DCs Facilitate Th17 Differentiation

Figure 10:
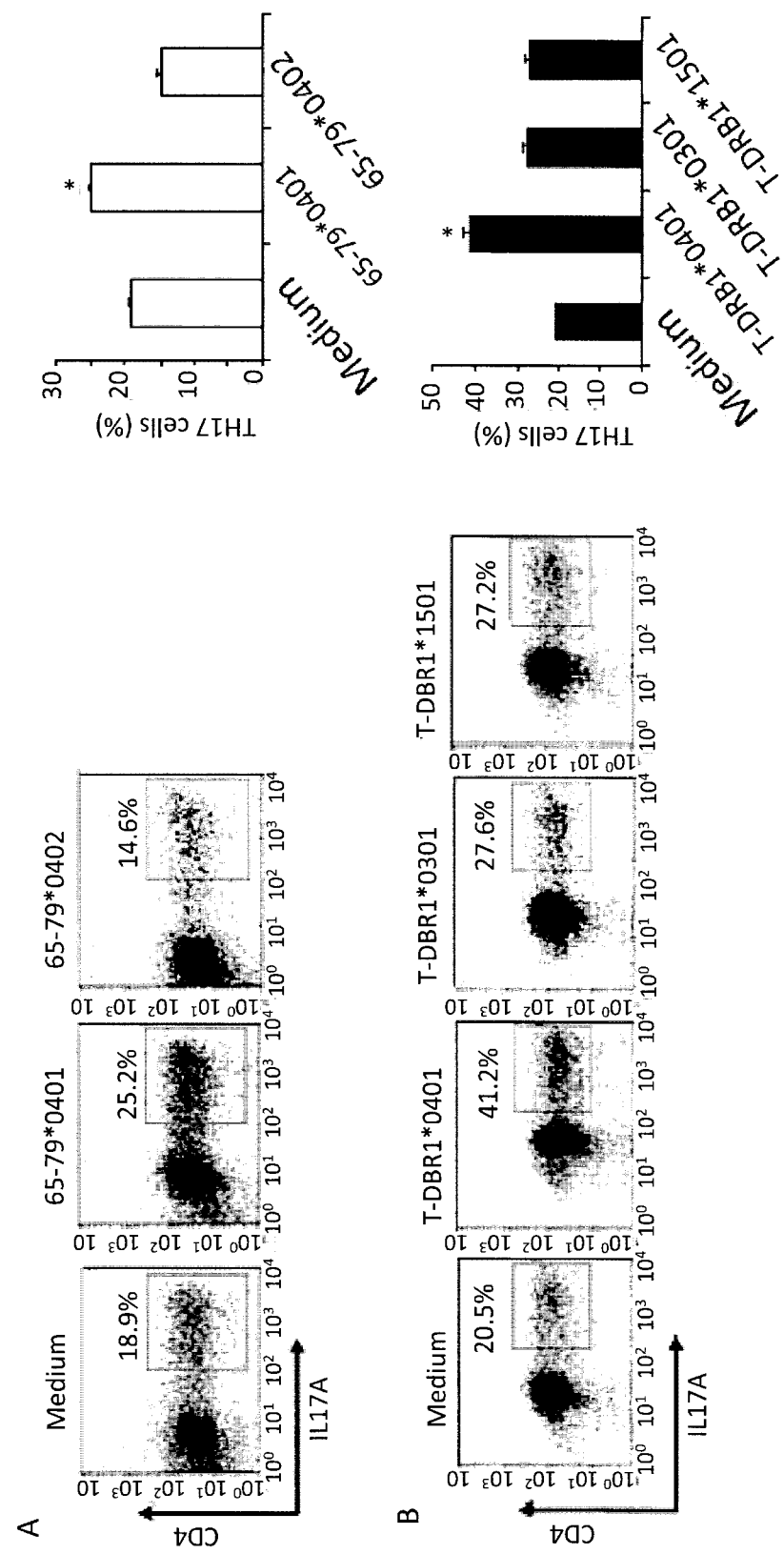
FIG. 10 shows ISL facilitates Th17 differentiation. DBA/1 bone marrow-derived CD11c+ DCs were cultured overnight in the presence or absence of (A) ISL 65-79*0401 or ISL-negative control 65-79*0402, or (B) ISL-positive T-DRB1*0401 tetramers, versus ISL-negative T-DRB1*0301, or T-DRB1*1501 tetramers. Syngeneic splenic CD4+ CD25− CD62L+ CD44− naïve T cells plus a Th17-differentiation cytokine/antibody cocktail were then added to the culture and incubated for 6 days. Intracellular IL17A was determined by flow cytometry. On the left: a representative experiment, one of three repetitions, showing percentages of CD4+ IL17A+ cells as dot plots. On the right: bar graphs show results presented as mean percentage±SD of replicate samples.

In the CD11c+ CD8− DC subset, the ISL ligand 65-79*0401 triggered a robust production of IL-6, an obligatory cytokine for Th17 differentiation. IL-23 production by LPS-treated DCs was also augmented by 65-79*0401. Experiments were conducted during development of embodiments of the present invention to determine whether the ISL ligand can facilitate Th17 differentiation or activation. CD11c+ DCs were stimulated overnight with either peptidic or tetrameric ligands. CD4+ CD25− CD62L+ CD44− naïve T cells were added and cultured in the presence of a Th17-polarizing cocktail of cytokines and antibodies. After 6 days, cells were collected and analyzed by flow cytometry. The ISL ligand 65-79*0401 induced a significant increase in the differentiation of CD4+ IL17A+ T cells (ISLE FIG. 10A). A more robust ISL-induced Th17 polarization effect was observed when DCs were stimulated with ISL-positive HLA-DR tetramers (ISLE FIG. 10B).

Figure 11:
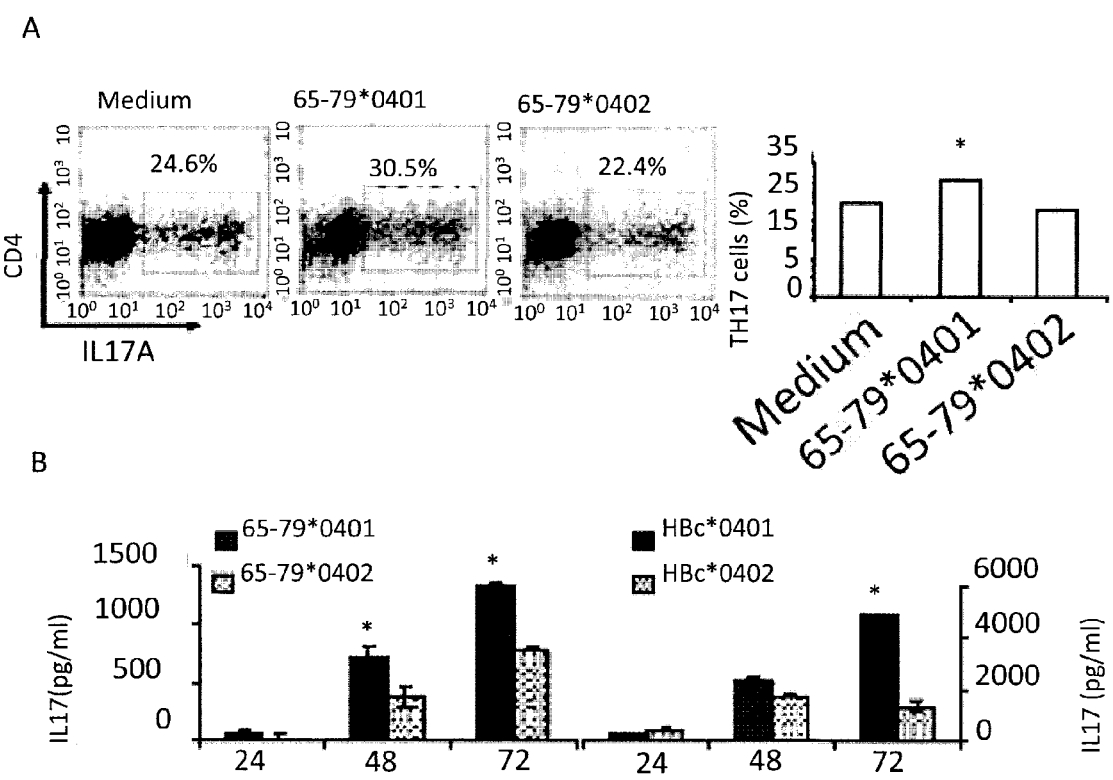
FIG. 11 shows activation of IL-17 production in CD4+ T cells by ISL. (A) DBA/1 bone marrow-derived CD11c+ DCs were cultured overnight with different peptidic ligands as above. Syngeneic splenic CD4+ T cells plus a Th17-polarizing cocktail were added to the culture and incubated for 6 days. IL-17A-positive cells were quantified by flow cytometry. On the left: dot plots showing percentage of CD4+ IL17A+ T cells. On the right: bar graphs (mean±SD) of replicate samples (B) To measure IL-17 secretion, DBA/1 bone marrow-derived CD11c+ DCs were treated overnight with peptidic or particular ligands or medium and then co-cultured with CD4+ T cells as above. Supernatants were assayed for IL-17 content by ELISA.

To determine whether ISL-activated DCs can increase IL-17 production in CD4+ T cells, CD11c+ DCs were incubated overnight with ISL ligands or control reagents. Cells were then co-cultured with total CD4+ T cells. ISL-activated DCs induced higher intracellular (ISLE FIG. 11A) and extracellular (ISLE FIG. 11B) IL-17 expression in co-cultured CD4+ T cells, compared to cells cultured with DCs pre-incubated with a control reagents or medium. The effect was seen both with a soluble ISL peptidic ligand, as well as with conformationally preserved ligand in the form of an HBc particle (ISLE FIG. 11B).

The ISL affects the proliferation of Th17 and Tregs in a reciprocal manner. Enhanced expansion through increased proliferative activity of Th17 cells and decreased proliferative activity of Tregs was observed in both TCR-independent and TCR-mediated T cell activation conditions.

Figure 12:
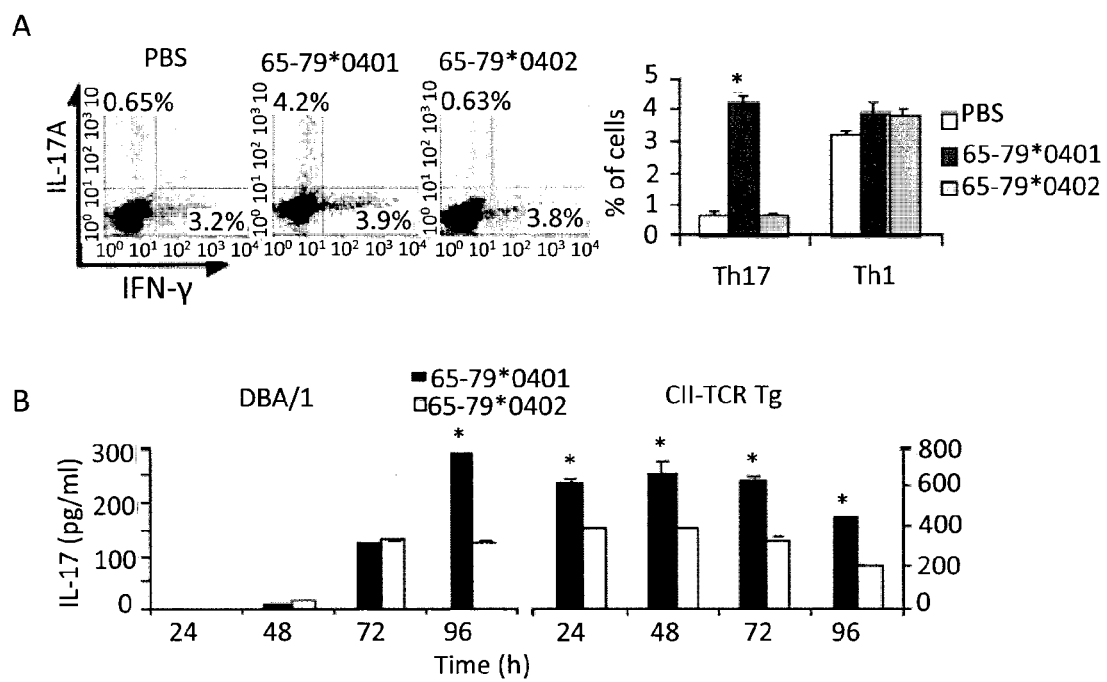
FIG. 12 shows ISL facilitates Th17 polarization in vivo. (A) DBA/1 mice were immunized with CII in CFA in the presence of PBS, 65-79*0401 or 65-79*0402. On day 7, cells from draining lymph nodes were isolated, cultured for 6 hours with PMA, Ionomycin and Brefeldin A and then stained with anti-mouse CD4, IL17A and IFN-γ as above. On the left: Representative dot plots showing percentages of IL17A+ and IFN-γ+ cells obtained from gated CD4+ cells. On the right, bar graphs showing results as mean±SD of duplicate experiments. (B) DBA/1 and CII-TCR Tg mice were immunized as in (A). On day 7, splenic cells were isolated and cultured with the synthetic peptide $CII_{260-267}$ (5 μg/ml). Supernatants were collected every 24 hours and assayed for IL-17 levels by ELISA.
Figure 13:
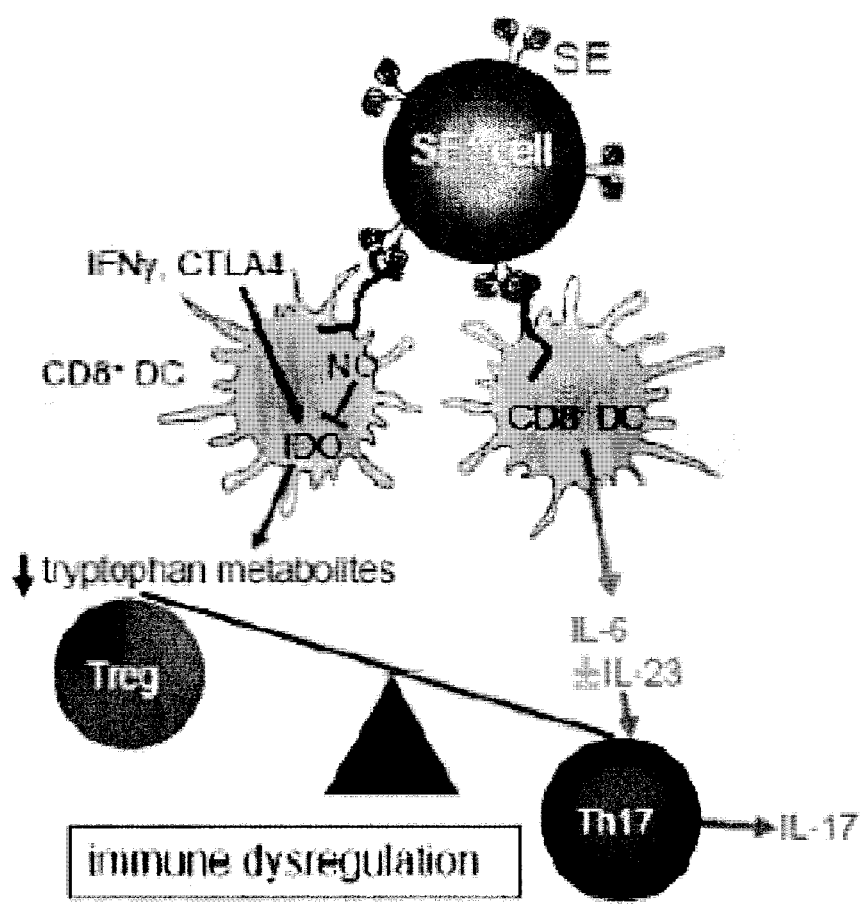
FIG. 13 shows ISL function in autoimmunity; although the present invention is not limited to any particular mechanism of action and an understanding of the mechanism of action is not necessary to practice the present invention.

Experiments were conducted during development of embodiments of the present invention to characterize the ISL polarizing effect in vivo (ISLE FIG. 12). Draining lymph nodes of control DBA/1 mice immunized with CII had a 0.65% abundance of Th17 cells, consistent with published data showing frequencies of less than 1% of Th17 in draining lymph nodes (Iwanami et al. 2009 Arthritis Res Ther 11:R167; Notley et al. 2008. J Exp Med 205:2491-2497; herein incorporated by reference in their entireties). Co-administration of the ISL-negative 65-79*0402 had no effect on Th17 abundance. However, co-administration of the ISL ligand 65-79*0401 dramatically increased the frequency of these cells (ISLE FIG. 12A). The ISL-induced expansion was specific for Th17 cells since there was no change in the frequency of Th1 (IFNγ-positive) cells (ISLE FIG. 12A). Additionally, splenocytes from DBA/1 mice immunized with CII in the presence of the ISL ligand 65-79*0401 showed significantly more robust CII-stimulated IL-17 production, compared to splenocytes obtained from mice co-immunized with the ISL-negative control 65-79*0402 (ISLE FIG. 12B). Experiments conducted during development of embodiments of the present invention demonstrate that the ISL facilitates Th17 polarization both in vitro and in vivo.

Example 4

Expansion of Pathogen-Specific Th17 Cells by ISL

In order to examine the utility of ISLs described herein, experiments were performed to determine whether the ISLs could expand anti-pathogen-specific Th17 cells. To this end mice were immunized with chicken collagen type II (CII)+*M tuberculosis* H37Ra in the form of Complete Freund's Adjuvant (CFA) in the presence of ISL (peptide 65-79*0401), or a control peptide (65-79*0402). The draining lymph nodes were harvested and single cell suspensions were generated.

Six to 10 weeks old DBA/1 mouse carrying transgenic collagen type II-specific TCR (D1Lac.Cg-Tg(TCRa,TCRb) 24Efro/J) were immunized with chicken collagen type II (CII) in Complete Freund's Adjuvant (CFA) containing *Mycobacterium tuberculosis* H37Ra. 50 µl of an emulsion containing 100 µg of CII in 25 µl of 0.05 M acetic acid and 25 µl of CFA was injected intradermally at the base of the tail. At days 0, 7, 14 and 21, mice were injected intraperitoneally with 100 µg of ISL (peptide 65-79*0401), or control peptide (65-79*0402) in 50 µl of PBS. On day 42 lymph-nodes were isolated, single-cell suspensions were made, and Th17 cells were quantified by flow cytometry (See FIG. 14A and discussion below). Lymph-node cells (1×10⁶ cells/ml) were re-stimulated in vitro in 96 well plates with 100 µg/ml of denaturated CII, 10 µg/ml of *Mycobacterium bovis* purified protein derivative (PPD) of mycobacteria, or PBS (NIL). After 6 days, cells were harvested, stained and analyzed by flow cytometry (See FIG. 14B and discussion below). All samples were acquired on a FACScalibur, and data were analyzed with CellQuest Pro software (BD biosciences). An appropriate isotype-matched control antibody was used in all FACS analysis. Bar graphs show results as the percentage (mean±SEM). *p<0.03, compared to PBS and 65-79*0402.

Figure 14:
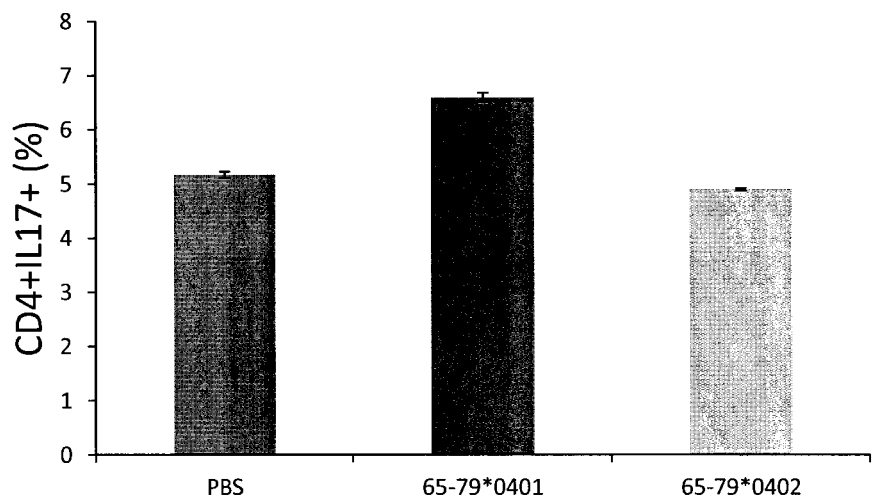
FIG. 14 shows that ISL facilitates polarization of bacterial antigen-specific Th17 cells.
Figure 14:
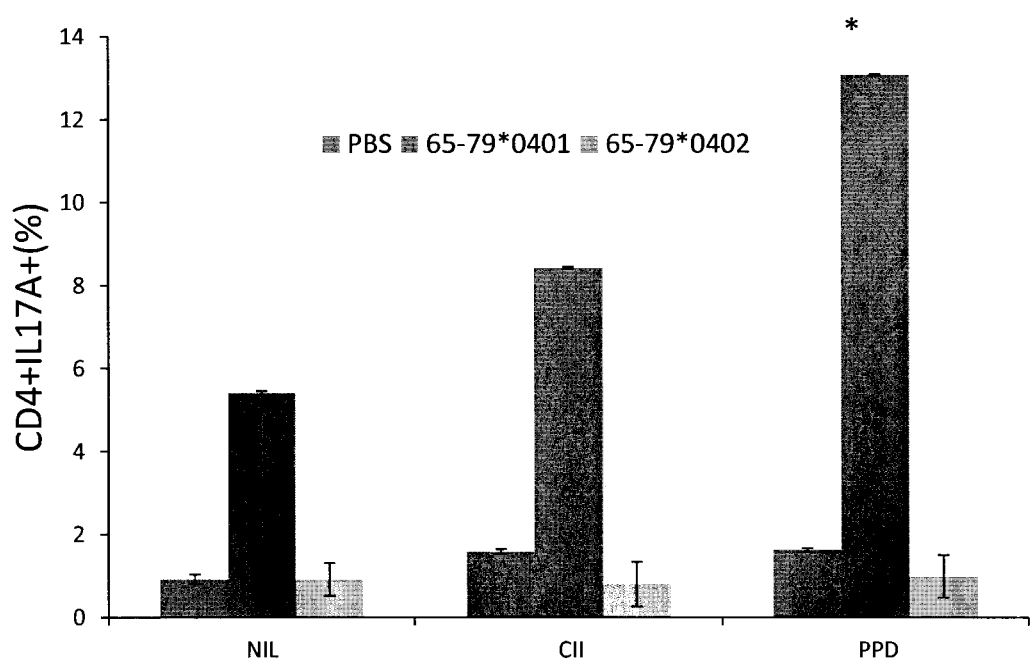

Flow cytometry analysis revealed a significant increase of total antigen non-stimulated Th17 cells in draining lymph nodes (See FIG. 14). In order to determine the impact of ISL on antigen-specific Th17 cells, lymph node cells were re-stimulated for 6 days in the presence of a purified derivative protein (PPD) of *M. tuberculosis*, CII, or PBS. In mice administered ISL, antigen-specific re-stimulation resulted in major expansion of Th17 cells (See FIG. 14B). Specifically, without any antigen stimulation the percentage of Th17 cells after 6 days in culture was 5.4±0.4%; while cultures stimulated with CII produced 8.4±0.5% Th17 cells. Cultures re-stimulated with the bacterial antigen PPD gave a robust expansion of anti-PPD-specific Th17 cells (13.1±0.5%). Thus, in some embodiments, the invention provides that ISL facilitates anti-bacterial immune responses (e.g., polarization of bacterial antigen-specific Th17 cells).

Example 5

Bioactive Cyclic Peptide Ligands

Experiments were conducted during development of embodiments of the invention to generate conformationally intact peptidomimetic ISL reagents. The utility of cyclic peptides was examined with an interest in determining whether the cyclization of the peptides improved chemical stability and/or extended the biological half-life compared to their linear counterparts. In order to avoid usage of essential side chains, and/or amino and carboxyl ends, a backbone cyclization (BC) strategy can be utilized to impose a conformational constraint on peptides where nitrogen atoms in the backbone are covalently connected by an intramolecular bridge to form a ring. An advantage of backbone cyclization is that cyclization is achieved mainly by using backbone atoms and not side chains that are important for biological activity.

Materials and Methods.

Abbreviations used herein are as follows: AGBU, Alloc glycine building units; Alloc, allyloxycarbonyl; BTC, bis(trichloromethyl)carbonate; CD, Circular dichroism; DCM, dichloromethane; DIPEA, diisopropylethylamine; Fmoc, 9-fluorenylmethyloxycarbonyl; HATU, (2-(7-Aza-1H-benzotriazole-1-yl)-1,1,3,3-tetramethyluronium hexafluorophosphate); HBTU, (2-(1H-benzotriazole-1-yl)-1,1,3,3-tetramethyluronium hexafluorophosphate); HLA, human leukocyte antigen; MBHA, methylbenzhydrylamine; NMP, 1-methyl-2-pyrrolidinone; NO, nitric oxide; RA, Rheumatoid arthritis; RP-HPLC, reverse phase high pressure liquid chromatography; SAR, structure activity relationship; SE, shared epitope; SPPS, solid phase peptide synthesis; TDW, tri-distilled water; TFA, trifluoroacetic acid.

All starting materials were purchased from commercial sources and were used without further purification. Exact mass spectra were recorded on an AGILENT TECHNOLOGIES 6520B ACCURATE MASS Q-TOF LC/MS. MALDI-TOF spectra were recorded on a PERSEPTIVE BIOSYSTEMS MALDI-TOF MS, using α-cyano-4-hydroxycinnamic acid as the matrix. All analytical HPLC were recorded at 220 nm at a flow of 1 ml/min on a RP-18 column (5 μm 250×4.6 mm, 110 Å), eluents A (0.05% TFA in TDW) and B (0.05% TFA in ACN) were used in a linear gradient (95% A→5% A in 35 min). Preparative HPLC were recorded at 220 nm on a RP-18 column (10μ 250×10 mm, 110 Å), Eluents A (0.05% TFA in TDW) and B (0.05% TFA in ACN) were used in a linear gradient (95% A→75% A in 30 min) at a flow of 5 ml/min.

Peptide design. All the peptides were synthesized using standard Fmoc SPPS procedures (See, e.g., Chan and White, *Fmoc Solid Phase Peptide Synthesis*; Oxford: Oxford University Press, 2000) on Rink amide MBHA resin as the solid support. The urea backbone cyclic peptides, designated c(HSn-4), were synthesized according to the procedures described by Hurevich et al. (See, e.g., Hurevich et al., *Journal of Peptide Science* 2010, 16, 178) using various AGBU, where n stands for the number of atoms in the N-alkyl chain on the glycine at position 2. The sequences of the linear 15 mer peptides are as follows:

65-79*0401:
(SEQ ID NO. 7)
H-Lys-Asp-Leu-Leu-Glu-Gln-Lys-Arg-Ala-Ala-Val-Asp-Thr-Tyr-Cys-NH2

65-79*0402:
(SEQ ID NO. 9)
H-Lys-Asp-Ile-Leu-Glu-Asp-Glu-Arg-Ala-Ala-Val-Asp-Thr-Tyr-Cys-NH2

65-79*0404:
(SEQ ID NO. 8)
H-Lys-Asp-Leu-Leu-Glu-Gln-Arg-Arg-Ala-Ala-Val-Asp-Thr-Tyr-Cys-NH2

General methods for SPPS. Swelling: The resin was swelled for at least 2 h in DCM. Fmoc removal: The resin was treated with a solution of 20% piperidine in NMP (2×20 min) and then washed with NMP (5×2 min). HBTU coupling: Fmoc protected amino acids (1.5 equiv) were dissolved in NMP. DIPEA (1.5 equiv) and HBTU (1.5 equiv) were added and the mixture was pre-activated by mixing for 1 min, added to the resin, and shaken for 1 h. The resin was washed with NMP (3×2 min). HATU coupling: Fmoc protected amino acids (1.5 equiv) were dissolved in NMP, DIPEA (1.5 equiv) and HATU (1.5 equiv) were added and the mixture was pre-activated by mixing for 1 min, added to the resin, and shaken for 2 h. The resin was washed with NMP (3×2 min). Alloc removal: The resin was washed with DCM (2×2 min) and dried under vacuum. A solution of PhSiH$_3$ (10 equiv) in DCM was added under a stream of argon and Pd(PPh$_3$)$_4$(0) (0.5 equiv) was added. The reaction was stirred in the dark for 1 h and then washed with 0.5% DIPEA in NMP (3×5 min), 0.5% sodium diethyldithiocarbamate trihydrate in NMP (5×2 min), NMP (2×2 min) and DCM (2×2 min). Urea cyclization: A solution of BTC (0.33 equiv) in DCM was added to the resin and stirred. After 2 h, DIPEA (2 equiv) was added and the reaction was stirred overnight at room temperature. The resin was washed with DCM (2×2 min). Cleavage: The resin was washed with DCM (2×2 min) and dried under vacuum. A solution of 2.5% TDW and 2.5% triisopropylsilane in TFA was added and the reaction proceeded for 3 h at room temperature. The solution was separated by filtration and the resin was rinsed with neat TFA. The TFA mixture was treated with a cooled solution of ether:hexane 1:1 and the peptides were precipitated by centrifugation. The crude peptides were dissolved in ACN:TDW 1:1 solution and lyophilized.

Nitric Oxide Assay. Human fibroblast M1 cells were plated at a density of $1 \times 10^5$ cells per well in 96-well plates the day prior to the Nitric Oxide assay. To determine the rate of NO production in fibroblast, cells were first loaded with 20 μM of the fluorescent NO probe 4,5-diaminofluorescein diacetate (DAF-2DA), incubated in the dark at 37° C. for 1 hour and washed in 100 μL of DMEM/phenol red-free medium. The fluorescence level was recorded every 5 minutes over a period of 500 minutes, using a Fusion αHT system (PerkinElmer Life Sciences) at an excitation wavelength of 488 nm and emission wavelength of 515 nm. The NO production rate is expressed as the mean±SEM fluorescence units per minute.

CD Measurements. Samples of each peptide were prepared by dissolving a lyophilized peptide in TDW. Far-UV CD spectra were collected over 190-260 nm at room temperature using a J-810 spectropolarimeter (Jasco) in a 0.1 cm quartz cuvette for far-UV CD spectroscopy.

Trypsin/chymotrypsin stability assay. The trypsin stability assay was conducted as previously described (See, e.g., Pakkala et al., Journal of Peptide Science 2007, 13, 348; Tal-Gan et al., Bioorganic & Medicinal Chemistry 2010, 18, 2976. 400 μL of each peptide (1 mM) dissolved in 200 mM NH$_4$HCO$_3$ buffer solution (pH 8) were mixed with 1 μL of trypsin and chymotrypsin (porcine pancreas, Biological Industries Israel, Beit Haemek LTD) solution (2.5 mg/1 ml). The peptides were incubated at 37° C., 30 samples were taken every 30 min and mixed with 30 μL of 2% TFA and 30% ACN in water. Samples were analyzed by HPLC and by MALDI-TOF MS.

Figure 15:
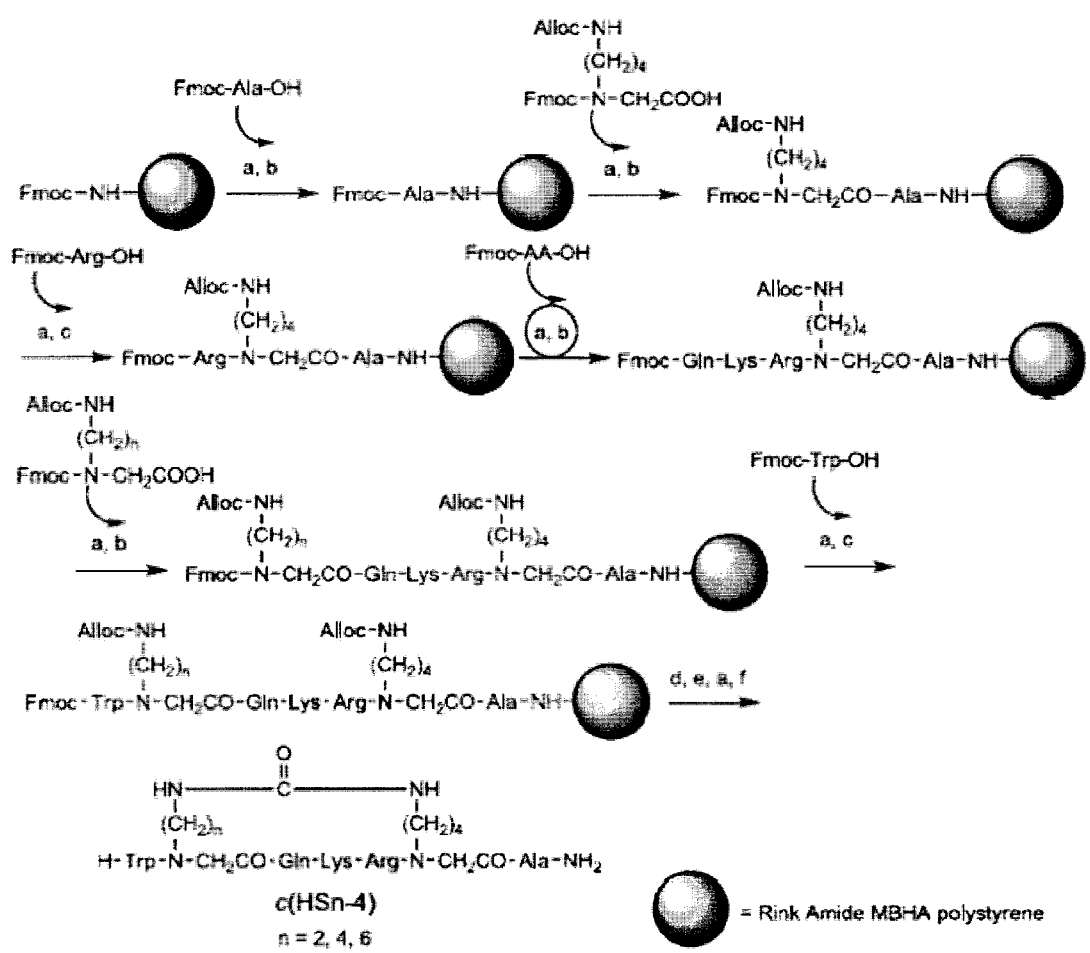
FIG. 15 shows a synthesis scheme of c(HSn-4) compounds. Conditions: a) 20% piperidine, DMF; b) HBTU, DIPEA; c) HATU, DIPEA; d) Pd(PPh3)4(0), $PhSiH_3$; e) BTC, DIPEA; f) TFA, TIPS, TDW.

Peptide design and synthesis. Helix mimetic cyclic analogs usually have bridges at positions i, i+4 or i, i+7 (See, e.g., Moellering et al., Nature 2009, 462, 182; Walensky et al., Science 2004, 305, 1466). The consensus SE motif Gln-Lys-X-X-Ala (SEQ ID NO. 15) was incorporated into an i, i+4 backbone cyclic scaffold. A Trp residue was added to the amino terminus to aid in determining the concentrations of the cyclic analogs using UV spectroscopy (See, e.g., Gill and von Hippel, Anal Biochem 1989, 182, 319). The synthesis and general structure of the backbone cyclic peptides are described in FIG. 15.

The characterization of the cyclic peptides is summarized in Table 2, below.

TABLE 2

Characterization of peptides generated utilizing backbone cyclization.

Figure 16:
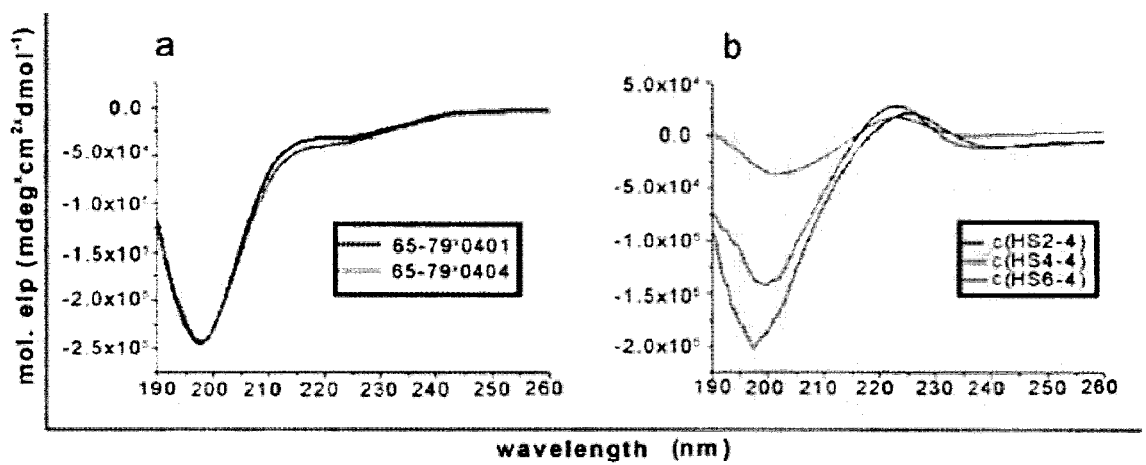
FIG. 16 shows CD spectra of cyclic and 15-mer linear peptides. a) Random coil CD spectra were observed for the two linear 15-mer peptides. b) Type III β-turn CD spectra were observed for the three cyclic analogs.

| Peptide Name | n | Bridge Size | Ring Size | Calcd MH+ | Observed MH+ (HRMS) | Purity HPLC (%) | $T_R$ HPLC* (min) |
|---|---|---|---|---|---|---|---|
| c(HS2-4) | 2 | 9 | 22 | 941.5428 | 941.5446 | >95 | 18.65 |
| c(HS4-4) | 4 | 11 | 24 | 969.5741 | 969.5744 | >95 | 18.68 |
| c(HS6-4) | 6 | 13 | 26 | 997.6054 | 997.6062 | >95 | 18.83 |

β-turn conformation observed for the cyclic analogs using CD. The conformational changes induced by cyclization and the variety of ring sizes were studied by CD of the cyclic peptides and two positive control 15-mers (65-79*0401, H-Lys-Asp-Leu-Leu-Glu-Gln-Lys-Arg-Ala-Ala-Val-Asp-Thr-Tyr-Cys-NH$_2$ (SEQ ID NO. 7), and 65-79*0404, H-Lys-Asp-Leu-Leu-Glu-Gln-Arg-Arg-Ala-Ala-Val-Asp-Thr-Tyr-Cys-NH$_2$ (SEQ ID NO. 8)). The two linear 15-mer peptides had no defined structure and the CD spectra resembled a random coil (See FIG. 16a). CD spectra of the three cyclic analogs indicated a putative Type III β-turn conformation (See FIG. 16b; see also Crisma et al., Int J Pept Protein Res 1984, 23, 411; Johnson, Annu Rev Biophys Biophys Chem 1988, 17, 145). Thus, in some embodiments, the cyclic, bioactive pharmacophors of the peptide acquire an active conformation (e.g., helix conformation) upon binding to their binding site. Although an understanding of a mechanism is not necessary to practice the invention, and the invention is not limited to any particular mechanism, in some embodiments, the cyclic (e.g., short) peptides display enhanced activity compared to the linear (e.g., longer) peptides due to a restricted conformation of the cyclic peptides (e.g., a more biologically active confirmation).

Figure 17A:
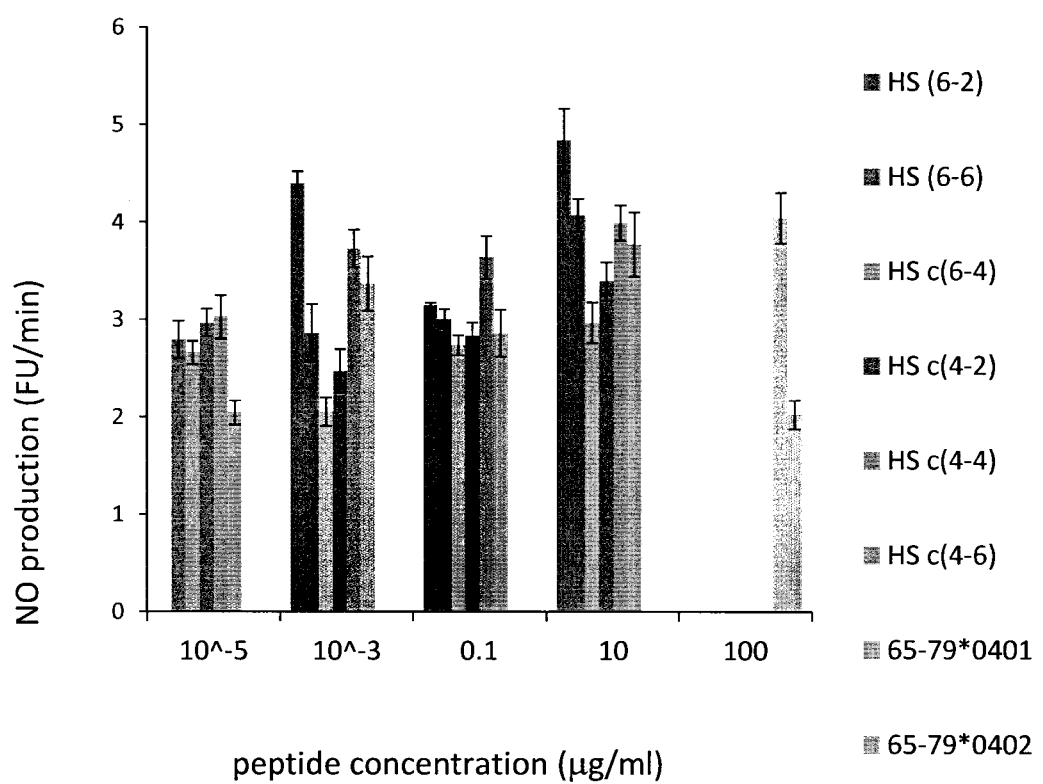
FIGS. 17A and 17B show dose-response experiments of NO production rate induced by cyclic analogs. Human M1 fibroblasts were incubated with different concentrations of the listed cyclic peptides, or with 50 μM of positive (65-79*0401) or negative (65-79*0402) control peptides. NO production rates were determined using the fluorescent probe 4,5-diaminofluorescein diacetate (DAF-2DA) (See Ling et al., Arthritis Res Ther 2007, 9, R5; Ling et al., J. J Immunol 2007, 179, 6359; Ling et al., Arthritis Rheum 2006, 54, 3423).
Figure 17B:
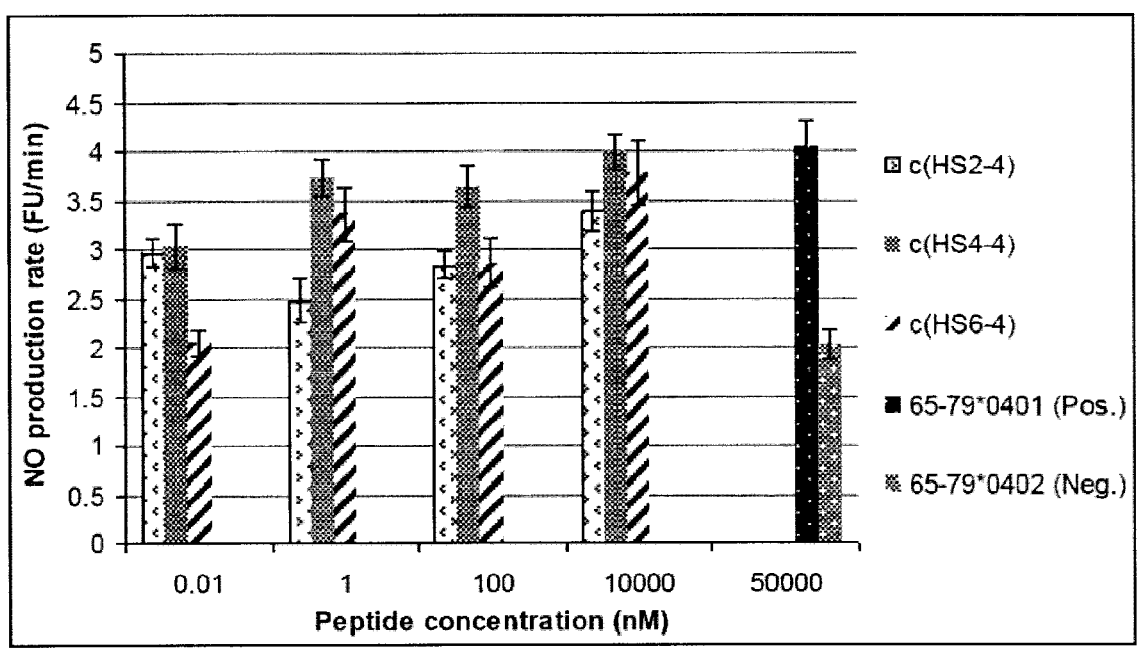

NO production induced by the cyclic analogs. The ability of the cyclic analogs to activate NO production in fibroblasts was examined. The 15-mer peptides 65-79*0401 (H-Lys-Asp-Leu-Leu-Glu-Gln-Lys-Arg-Ala-Ala-Val-Asp-Thr-Tyr-Cys-NH$_2$) (SEQ ID NO. 7) and 65-79*0402 (H-Lys-Asp-Ile-Leu-Glu-Asp-Glu-Arg-Ala-Ala-Val-Asp-Thr-Tyr-Cys-NH$_2$) (SEQ ID NO. 9) were used as positive and negative controls, respectively. An optimal concentration for the positive control, 65-79*0401, was previously determined to be 50 μM (See, e.g., Ling et al., Arthritis Res Ther 2007, 9, R5; Ling et al., J. J Immunol 2007, 179, 6359; Ling et al., Arthritis Rheum 2006, 54, 3423). FIGS. 17A and 17B show that cyclic analogs activated NO production significantly above the negative control levels. Furthermore, as shown in FIG. 17B, c(HS6-4) maintained elevated NO production levels at concentrations five times lower than the positive control. Both c(HS4-4) (SEQ ID NO: 2), and c(HS6-2) (SEQ ID NO. 3) were observed to be potent analogs.

Both of these cyclic peptides maintained high NO production levels even in concentrations 50,000 times lower than 65-79*0401, and activated NO production even in the low nM concentrations. Accordingly, in some embodiments, the invention provides that subtle changes in the conformation of bioactive SE pharmacophors alter the biological activity of the peptides.

Thus, the invention provides a variety peptides encompassing a broad range of activity (e.g., biological activity (e.g., ability to activate shared epitope (SE) type signaling events). In some embodiments, the invention provides cyclic peptides (e.g., selected from SEQ ID NOS. 1-6, 13 and 14) for use as agonists of SE triggered signaling (e.g., to induce nitric oxide (NO) production and/or NO signaling cascades (e.g., to induce an immune response)). In a preferred embodiment, the invention provides QKRAA (SEQ ID NO.:2) or QKRAA (SEQ ID NO.:3) as potent agonists of biological signalling cascades (e.g., to induce nitric oxide (NO) production and/or NO signaling cascades and/or to induce an immune response (e.g., increase T helper 17 (Th17) cell expansion, increase production of IL-17 and/or IL-6, or to inhibit T regulatory cell activity and/or expansion (e.g., to block or decrease T cell tolerance))). In other embodiments, one or more peptides described herein are used as antagonists of SE triggered signaling.

Figure 18:
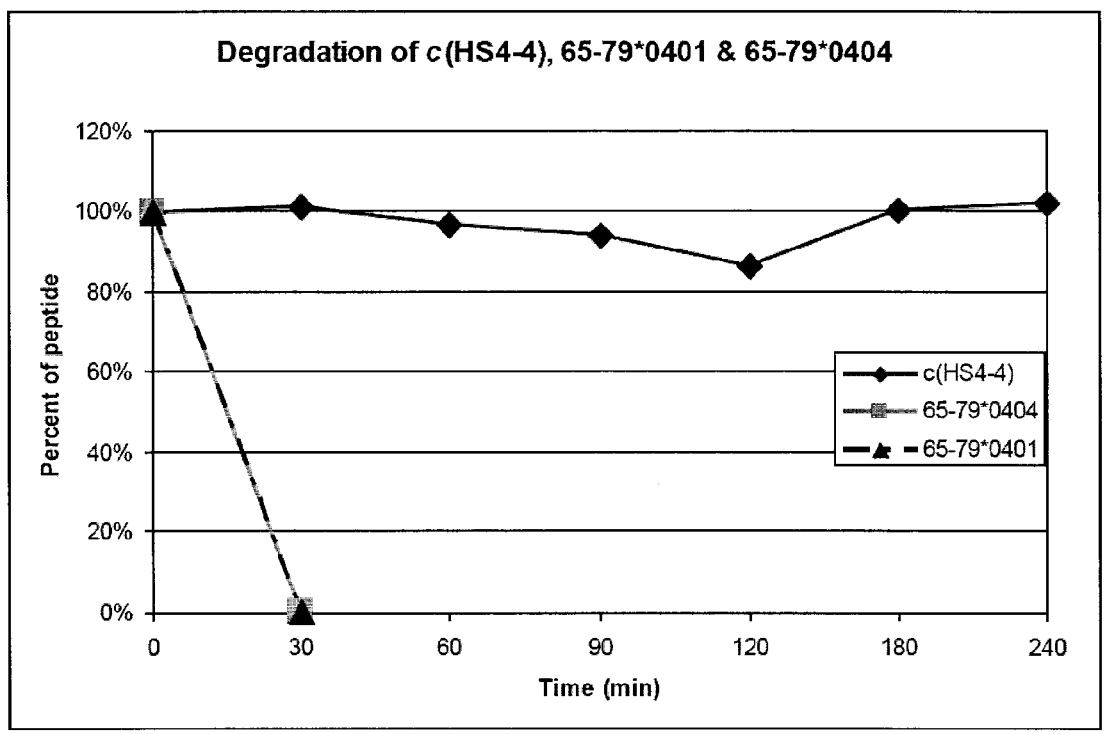
FIG. 18 shows a comparison of the degradation rates of c(HS4-4), 65-79*0401 and 65-79*0404 towards trypsin and chymotrypsin enzymatic cleavage.

Stability towards enzymatic degradation. In order to assess the stability of one of the potent cyclic analogs, c(HS4-4) (SEQ ID NO:2), towards enzymatic degradation as compared to the linear 15-mers, 65-79*0401 and 65-79*0404, a trypsin/chymotrypsin stability assay was conducted. HPLC analysis was used to determine the percent of degradation (See FIG. 18), whereas MS analysis was used to identify the specific cleavage sites (See Table 3). The cyclic analog, c(HS4-4) was completely stable towards trypsin/chymotrypsin degradation even after 4 hours of incubation with the proteases whereas the linear analogs, 65-79*0401 and 65-79*0404 were degraded completely after 30 minutes (See FIG. 18).

| Name | Deduced sequence of fragment | Observed MHT |
|---|---|---|
| c(HS4-4) | [structure: H—Trp—N(—(CH$_2$)$_4$—NH—C(=O)—NH—(CH$_2$)$_4$—N—CH$_2$CO—Ala—NH$_2$)—CH$_2$CO—Gln-Lys-Arg—] | 969.53 |
| 65-79*0401 | K-D-L-L-E-Q-K-R-A-A-V-D-T-Y-C | 1752.98 |
| Fragment 1 | K-D-L-L-E-Q-K-R-A-A-V-D-T-Y | 1649.93 |
| Fragment 2 | C | ## |
| Fragment 3 | K-D-L-L-E-Q-K-R | 1029.64 |
| Fragment 4 | A-A-V-D-T-Y | 638.51 |
| Fragment 5 | K-D-L-L-E-Q-K | 872.53 |
| Fragment 6 | R-A-A-V-D-T-Y | 795.43 |
| 65-79*0404 | K-D-L-L-E-Q-R-R-A-A-V-D-T-Y-C | 1778.84 |
| Fragment 1 | K-D-L-L-E-Q-R-R-A-A-V-D-T-Y | 1676.84 |
| Fragment 2 | C | ## |
| Fragment 3 | K-D-L-L-E-Q-R-R | 1057.23 |

-continued

| Name | Deduced sequence of fragment | Observed MHT |
|---|---|---|
| Fragment 4 | A-A-V-D-T-Y | 638.59 |
| Fragment 5 | K-D-L-L-E-Q-R | 901.71 |
| Fragment 6 | R-A-A-V-D-T-Y | 795.40 |

Fragments were identified by MS ## Complementary fragment Table 3. Fragmentation of c(HS4-4), 65-79*0401 and 65-79*0404 after degradation by trypsin/chymotrypsin#

The specific cleavage sites were determined using MS analysis to extract further information about the degradation of the peptides. Several cleavage sites were identified from the analyzed fragments of the linear 15-mer peptides, 65-79*0401 and 65-79*0404, containing the SE motif (residues 70-74) (See Table 3). These cleavage sites were between Tyr78 and Cys79 (chymotrypsin), Arg72 and Ala73 (trypsin), and Arg71/Lys71 and Arg72 (trypsin). As two of the identified cleavage sites (after residue 71 and 72) are found within the SE segment and are conserved in the cyclic analog, the 15-mer peptides serve as good controls for comparison. Regarding the cyclic peptide, c(HS4-4), in accordance with the HPLC results, no fragments were observed in the MS analysis, indicating that the restricted conformation induced by cyclization was not recognized by trypsin and chymotrypsin. The fact that cleavage was not observed at either of the cleavage sites within the conserved SE segment (after residue 71 and 72) in the cyclic analog indicates that the use of backbone cyclization confers enzymatic stability to the peptides.

All publications and patents mentioned in the present application and/or listed below are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

The invention claimed is:

1. A method of inducing an immune response in a subject comprising administering to the subject an effective dose of a composition comprising an isolated cyclic peptide comprising an amino acid sequence selected from the group consisting of SEQ ID NOS.:1-6, 13 and 14 under conditions such that an immune response is generated in the subject.

2. The method of claim 1, wherein the immune response comprises expansion of Th17 cells.

3. The method of claim 2, wherein the Th17 cells are pathogen-specific.

4. The method of claim 1, wherein the immune response comprises inhibition of T regulatory cell differentiation or activity.

5. The method of claim 1, wherein the immune response comprises enhanced nitric oxide signalling.

6. The method of claim 1, wherein the immune response comprises enhanced production of IL-6.

7. A method of inhibiting T cell tolerance in a subject comprising administering to the subject an effective dose of a composition comprising an isolated cyclic peptide comprising an amino acid sequence selected from the group consisting of SEQ ID NOS.: 1-6, 13 and 14 under conditions such that T cell tolerance is reduced in the subject.

8. The method of claim 1, wherein the cyclic peptide is:

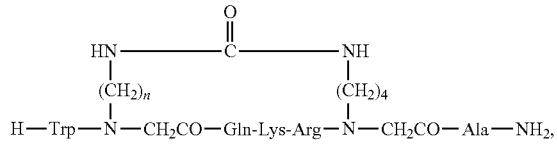

wherein n is selected from the group consisting of 2, 4 and 6.

9. The method of claim 1, wherein the cyclic peptide is generated using a method selected from the group consisting of a urea backbone cyclic protocol, an amide backbone-to-side chain cyclic peptide synthesis scheme, a peptide stapling protocol, and a combination thereof.

10. The method of claim 7, wherein the cyclic peptide is:

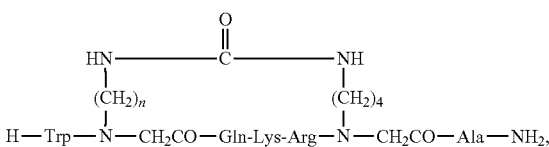

wherein n is selected from the group consisting of 2, 4 and 6.

11. The method of claim 7, wherein the cyclic peptide is generated using a method selected from the group consisting of a urea backbone cyclic protocol, an amide backbone-to-side chain cyclic peptide synthesis scheme, a peptide stapling protocol, and a combination thereof.

* * * * *